US010287317B2

(12) United States Patent
Muehlemann et al.

(10) Patent No.: US 10,287,317 B2
(45) Date of Patent: May 14, 2019

(54) PROPROTEIN CONVERTASE SUBTILISIN KEXIN TYPE 9 (PCSK9) ALLOSTERIC BINDING LIGANDS TO MODULATE SERUM LOW DENSITY LIPOPROTEIN (LDL) LEVELS

(71) Applicant: SRX Cardio, LLC, Pittsford, NY (US)

(72) Inventors: Michael M. Muehlemann, Liverpool, NY (US); Thomas E. Barta, Carrboro, NC (US); Kyle D. Monroe, Pittsford, NY (US); Jonathan William Bourne, Fairport, NY (US); Margaret Thompson Reece, Fayetteville, NY (US); Vesa Nevalainen, Weymouth, MA (US); Eric T. Baldwin, Upper Holland, PA (US)

(73) Assignee: SRX Cardio, LLC, Pittsford, NY (US)

( * ) Notice: Subject to any disclaimer, the term of this patent is extended or adjusted under 35 U.S.C. 154(b) by 0 days.

(21) Appl. No.: 14/825,700

(22) Filed: Aug. 13, 2015

(65) Prior Publication Data

US 2016/0083425 A1  Mar. 24, 2016

Related U.S. Application Data

(63) Continuation-in-part of application No. PCT/US2014/016640, filed on Feb. 15, 2014.

(60) Provisional application No. 62/037,478, filed on Aug. 14, 2014, provisional application No. 62/037,500, filed on Aug. 14, 2014, provisional application No. 61/836,381, filed on Jun. 18, 2013, provisional application No. 61/765,423, filed on Feb. 15, 2013.

(51) Int. Cl.

| C07K 7/06 | (2006.01) |
|---|---|
| C07K 5/097 | (2006.01) |
| C07K 5/087 | (2006.01) |
| C07K 5/103 | (2006.01) |
| C07K 5/09 | (2006.01) |
| C07K 5/107 | (2006.01) |
| C07K 5/065 | (2006.01) |
| C07K 5/078 | (2006.01) |

(52) U.S. Cl.
CPC ............ *C07K 7/06* (2013.01); *C07K 5/06078* (2013.01); *C07K 5/06156* (2013.01); *C07K 5/0812* (2013.01); *C07K 5/0817* (2013.01); *C07K 5/0821* (2013.01); *C07K 5/101* (2013.01); *C07K 5/1016* (2013.01)

(58) Field of Classification Search
CPC ....................................................... C07K 7/06
See application file for complete search history.

(56) References Cited

U.S. PATENT DOCUMENTS

| 2009/0275504 | A1* | 11/2009 | Mayne .................... | C07K 16/40 514/20.9 |
|---|---|---|---|---|
| 2010/0233177 | A1* | 9/2010 | Yowe ...................... | C07K 16/40 424/139.1 |
| 2011/0003315 | A1* | 1/2011 | Seidah ................... | C07K 16/40 435/7.21 |
| 2011/0117011 | A1* | 5/2011 | Jackson ................ | C12N 9/6454 424/1.11 |
| 2011/0142849 | A1* | 6/2011 | Rue ........................ | C07K 16/40 424/158.1 |
| 2012/0020975 | A1* | 1/2012 | Jackson ................ | A61K 31/22 424/139.1 |
| 2012/0082680 | A1* | 4/2012 | Sitlani ................... | C07K 16/40 424/158.1 |
| 2012/0213797 | A1* | 8/2012 | Jackson ................ | A61K 31/22 424/158.1 |
| 2012/0214181 | A1* | 8/2012 | Beyer ..................... | C12Q 1/37 435/7.92 |
| 2012/0231005 | A1* | 9/2012 | Luo ........................ | C07K 16/40 424/139.1 |
| 2012/0237945 | A1* | 9/2012 | Seidah ................... | C07K 16/40 435/7.1 |

FOREIGN PATENT DOCUMENTS

CN           102206249        10/2011

OTHER PUBLICATIONS

Palmer-Smith et al., 2010, Regulatory Effects of Peptides from the Pro and Catalytic Domains of Proprotein Convertase Subtilisin/Kexin 9 (PCSK9) on Low-Density Lipoprotein Receptor (LDL-R), Current Medicinal Chemistry, 17: 2168-2182.*
Zhang et al., 2014, identification of a Small Peptide That Inhibits PCSK9 Protein Binding to the Low Density Lipoprotein Receptor, The Journal of Biological Chemistry, 289(2): 942-955.*
Schroeder et al., 2014, Design and Synthesis of Truncated EGF-A Peptides that Restore LDL-R Recycling in the Presence of PCSK9 In Vitro, Chemistry & Biology, 21: 284-294.*
McNutt et al., 2009, Antagonism of Secreted PCSK9 Increases Low Density Lipoprotein Receptor Expression in HepG2 Cells, The Journal of Biological Chemistry, 284(16): 10561-10570.*
Bottomley et al., 2009, Structural and Biochemical Characterization of the Wild Type PCSK9-EGF(AB) Complex and Natural Familial Hypercholesterolemia Mutants, The Journal of Biological Chemistry, 284(2): 1313-1323.*

(Continued)

*Primary Examiner* — Amber D Steele
(74) *Attorney, Agent, or Firm* — Medlen & Carroll, LLP

(57) ABSTRACT

This invention is related to the field of hypercholesterolemia. In particular, the invention provides compositions and methods to modulate circulating levels of low density lipoproteins by altering the conformation of the protein PCSK9 using synthetic ligands and/or synthetic ligand derivative sequences of 3-8 amino acids ranging between 350-2,000 Da. Altering the conformation of PCSK9 affects the interaction between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands which can raise LDL levels.

28 Claims, 10 Drawing Sheets

Specification includes a Sequence Listing.

(56) References Cited

OTHER PUBLICATIONS

Shan et al., 2008, PCSK9 binds to multiple receptors and can be functionally inhibited by an EGF-A peptide, Biochemical and Biophysical Research Communications, 375: 69-73.*

Csermely et al., 2010, Induced fit, conformational selection and independent dynamic segments: an extended view of binding events, Trends in Biochemical Sciences, 35: 539-546.*

Abifadel, et al., "Mutations in PCSK9 Cause Autosomal Dominant Hypercholesterolemia." *Nat Genet*, 34(2):154-156 (2003).

Albericio and Carpino, "Coupling Reagents and Activation." *Methods Enzymol*, 289:104-126 (1997).

Benjannet, et al., "Effects of the Prosegment and pH on the Activity of PCSK9: Evidence for Additional Processing Events." *J Biol Chem*, 285(52):40965-40978 (2010).

Bhatnagar, et al., "Hypercholesterolaemia and Its Management." *BMJ*, 337 (2008).

Biggerstaff and Wooten, "Understanding Lipoproteins as Transporters of Cholesterol and Other Lipids." *Adv Physiol Educ*, 28(1-4):105-106 (2004).

Carmena, et al., "Atherogenic Lipoprotein Particles in Atherosclerosis." *Circulation*, 109(23 Suppl 1):III2-7 (2004).

DeVay, et al., "Characterization of Proprotein Convertase Subtilisin/Kexin Type 9 (PCSK9) Trafficking Reveals a Novel Lysosomal Targeting Mechanism Via Amyloid Precursor-Like Protein 2 (Aplp2)." *J Biol Chem*, 288(15):10805-10818 (2013).

Durrington, "Dyslipidaemia." *Lancet*, 362(9385):717-731 (2003).

Finn, et al., "Concept of Vulnerable/Unstable Plaque." *Arterioscler Thromb Vasc Biol*, 30(7):1282-1292 (2010).

Frank-Kamenetsky, et al., "Therapeutic RNAi Targeting PCSK9 Acutely Lowers Plasma Cholesterol in Rodents and LDL Cholesterol in Nonhuman Primates." *Proc Natl Acari Sci USA*, 105(33):11915-11920 (2008).

Goldstein, et al., "Receptor-Mediated Endocytosis: Concepts Emerging from the LDL Receptor System." *Annu Rev Cell Biol*, 1:1-39 (1985).

Graham, et al., "Antisense Inhibition of Proprotein Convertase Subtilisin/Kexin Type 9 Reduces Serum LDL in Hyperlipidemic Mice." *J Lipid Res*, 48(4):763-767 (2007).

Grundy, et al., "Primary Prevention of Coronary Heart Disease: Guidance from Framingham: A Statement for Healthcare Professionals from the AHA Task Force on Risk Reduction. American Heart Association." *Circulation*, 97(18):1876-1887 (1998).

Gupta, et al., "A Locked Nucleic Acid Antisense Oligonucleotide (LNA) Silences PCSK9 and Enhances LDLR Expression in Vitro and in Vivo." *PLoS One*, 5(5):e10682 (2010).

Hobbs, et al., "The LDL Receptor Locus in Familial Hypercholesterolemia: Mutational Analysis of a Membrane Protein." *Annu Rev Genet*, 24:133-170 A (1990).

Hobbs, et al., "The LDL Receptor Locus in Familial Hypercholesterolemia: Mutational Analysis of a Membrane Protein." *Anna Rev Genet*, 24:133-170 B (1990).

Innerarity, et al., "Familial Defective Apolipoprotein B-100: A Mutation of Apolipoprotein B That Causes Hypercholesterolemia." *J Lipid Res*, 31(8):1337-1349 (1990).

Jacobs, et al., "Report of the Conference on Low Blood Cholesterol: Mortality Associations." *Circulation*, 86(3):1046-1060 (1992).

Kontush and Chapman, "Antiatherogenic Small, Dense HDL—Guardian Angel of the Arterial Wall?". *Nat Clin Pract Cardiovasc Med*, 3(3):144-153 (2006).

Lambert, et al., "The Pcsk9 Decade." *J Lipid Res*, 53(12):2515-2524 (2012).

Lewington, et al., "Blood Cholesterol and Vascular Mortality by Age, Sex, and Blood Pressure: A Meta-Analysis of Individual Data from 61 Prospective Studies with 55,000 Vascular Deaths." *Lancet*, 370(9602):1829-1839 (2007).

Lindholm, et al., "PCSK9 LNA Antisense Oligonucleotides Induce Sustained Reduction of LDL Cholesterol in Nonhuman Primates," *Mol Ther*, 20(2):376-381 (2012).

Lopez, "Inhibition of PCSK9 as a Novel Strategy for the Treatment of Hypercholesterolemia." *Drug News Perspect*, 21(6):323-330 (2008).

Mayer, et al., "Annexin A2 Is a C-Terminal PCSK9-Binding Protein That Regulates Endogenous Low Density Lipoprotein Receptor Levels." *J Biol Chem*, 283(46):31791-31801 (2008).

Merrifield, "Solid Phase Peptide Synthesis. I. The Synthesis of a Tetrapeptide." *Journal of the American Chemical Society*, 85(14):2149-2154 (1963).

Saboo, Bristol-Myers Squibb Selects Isis Drug Targeting PCSK9 as Development Candidate for Prevention and Treatment of Cardiovascular Disease, *FierceBiotech: The BioTech Industry's Daily Monitor*. Retrieved from Source URL: http://www.fiercebiotech.com/press-releases/bristol-myers-squibb-selects-isis-drug-targeting-pcsk9-development-candidate-preventi. (Apr. 8, 2008).

Seidah, et al., "The Secretory Proprotein Convertase Neural Apoptosis-Regulated Convertase 1 (Narc-1): Liver Regeneration and Neuronal Differentiation." *Proc Natl Acad Sci USA*, 100(3):928-933 (2003).

Shan, et al., "PCSK9 Binds to Multiple Receptors and Can Be Functionally Inhibited by an EGF-a Peptide." *Biochem Biophys Res Commun*, 375(1):69-73 (2008).

Steinberg and Witztum "Inhibition of PCSK9: A Powerful Weapon for Achieving Ideal LDL Cholesterol Levels." *Proc Natl Acad Sci USA*, 106(24):9546-9547 (2009).

Suarez, "Relations of Trait Depression and Anxiety to Low Lipid and Lipoprotein Concentrations in Healthy Young Adult Women," *Psychosom Med*, 61(3):273-279 (1999).

Taylor, et al., "Statins for the Primary Prevention of Cardiovascular Disease." *Cochrane Database Syst Rev*(1):CD004816 A (2011).

Taylor, et al., "Statins for the Primary Prevention of Cardiovascular Disease." *Cochrane Database Syst Rev*(1):CD004816 B (2011).

Zhang, et al., "Identification of a Small Peptide That Inhibits PCSK9 Protein Binding to the Low Density Lipoprotein Receptor." *J Biol Chem*, 289(2):942-955 (2014).

Chen, et al., "SEC24A Deficiency Lowers Plasma Cholesterol through Reduced PCSK9 Secretion." *Elife*, 2:e00444 (2013).

Ferri, "Proprotein Convertase Subtilisin/Kexin Type 9: From the Discovery to the Development of New Therapies for Cardiovascular Diseases." *Scientifica (Cairo)*, 2012:927352 (2012).

Kosenko, et al., "Low Density Lipoprotein Binds to Proprotein Convertase Subtilisin/Kexin Type-9 PCSK9) in Human Plasma and Inhibits PCSK9-Mediated Low Density Lipoprotein Receptor Degradation." *J Biol Chem*, 288(12):8279-8288 (2013).

Saavedra, et al., "The M2 Module of the Cys-His-Rich Domain (CHRD) of PCSK9 Protein Is Needed for the Extracellular Low-Density Lipoprotein Receptor (LDLR) Degradation Pathway." *J Biol Chem*, 287(52):43492-43501 (2012).

Seidah, et al., "Annexin A2 Is a Natural Extrahepatic Inhibitor of the PCSK9-Induced LDL Receptor Degradation." *PLoS One*, 7(7):e41865 (2012).

Genebank XP_00111697 Genebank Protein 297290708. (2010).

Genebank CCE67184. (2012).

Genebank AFL41830.1. (2014).

Benjannet, et al., "The Proprotein Convertase (Pc) PCSK9 Is Inactivated by Furin and/or Pc5/6a: Functional Consequences of Natural Mutations and Post-Translational Modifications." *J Biol Chem*, 281(41):30561-30572 (2006).

Cohen, et al., "Low LDL Cholesterol in Individuals of African Descent Resulting from Frequent Nonsense Mutations in Pcsk9." *Nat Genet*, 37(2):161-165 (2005a).

Cohen, et al., "Low LDL Cholesterol in Individuals of African Descent Resulting from Frequent Nonsense Mutations in PCSK9." *Nat Genet*, 37(3):328 Corrigendum (2005b).

Davignon, et al., "The Influence of PCSK9 Polymorphisms on Serum Low-Density Lipoprotein Cholesterol and Risk of Atherosclerosis." *Curr Atheroscler Rep*, 12(5):308-315 (2010).

Kwon, et al., "Molecular Basis for Ldl Receptor Recognition by PCSK9." *Proc Natl Acad Sci USA*, 105(6):1820-1825 (2008).

Maxwell and Breslow, "Adenoviral-Mediated Expression of PCSK99 in Mice Results in a Low-Density Lipoprotein Receptor Knockout Phenotype." *Proc Natl Acad Sci USA*, 101(18):7100-7105 (2004).

(56) References Cited

OTHER PUBLICATIONS

Poirier, et al., "Dissection of the Endogenous Cellular Pathways of PCSK9-Induced Low Density Lipoprotein Receptor Degradation: Evidence for an Intracellular Route." *J Biol Chem*, 284(42):28856-28864 (2009).

Stein, et al., "Effect of a Monoclonal Antibody to PCSK99, Regn727/Sar236553, to Reduce Low-Density Lipoprotein Cholesterol in Patients with Heterozygous Familial Hypercholesterolaemia on Stable Statin Dose with or without Ezetimibe Therapy: A Phase 2 Randomised Controlled Trial." *Lancet*, 380(9836):29-36 (2012).

Zhang, et al., "Annexin B1 from Taenia Solium Metacestodes Is a Newly Characterized Member of the Annexin Family." *Biol Chem*, 388(6):601-610 (2007).

\* cited by examiner

PROPROTEIN CONVERTASE SUBTILISIN KEXIN TYPE 9 (PCSK9) ALLOSTERIC BINDING LIGANDS TO MODULATE SERUM LOW DENSITY LIPOPROTEIN (LDL) LEVELS

RELATED APPLICATIONS

This application is a continuation-in-part having priority to U.S. Provisional Application No. 62/037,478 (filed: Aug. 14, 2014), and U.S. Provisional Application No. 62/037,500 (filed: Aug. 14, 2014), and Patent Cooperation Treaty Application Number PCT/US14/16640 (filed: Feb. 15, 2014), having priority to U.S. Provisional Application No. 61/836, 381 (filed: Jun. 18, 2013) and U.S. Provisional Application No. 61/765,423 (filed: Feb. 15, 2013), all herein incorporated by reference.

FIELD OF INVENTION

This invention is related to the field of hypercholesterolemia. In particular, the invention provides compositions and methods to modulate circulating levels of low density lipoproteins by altering the conformation of the protein PCSK9 using a synthetic ligand and/or a synthetic ligand derivative having sequences of 3-8 amino acids ranging between 350-2,000 Da. Altering the conformation of PCSK9 affects the interaction between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands which can raise LDL levels.

BACKGROUND

Elevated plasma levels of low density lipoprotein cholesterol (LDL-C) represent the greatest risk factor for the development of coronary heart disease. Clearance of LDL-C from the plasma occurs primarily by the liver through the action of LDL receptors (LDLRs), which are cell surface glycoproteins that bind to apolipoproteinB 100 (apoB100) on LDL particles with high affinity and mediate their endocytic uptake. Goldstein et al., *Annu. Rev. Cell Biol.* 1:1-39 (1985). Autosomal dominant hypercholesterolemia (ADH) is associated with mutations that reduce plasma LDL clearance that are found in genes encoding the LDLR (familial hypercholesterolemia (FH)) or apoB100 (familial defective apoB100). Hobbs et al., *Annu. Rev. Genet.* 24, 133-170 (1990); and Innerarity et al., *J. Lipid Res.* 31:1337-1349 (1990), respectively.

The low density lipoprotein (LDL) receptor (LDLR) mediates efficient endocytosis of VLDL, VLDL remnants, and LDL. As part of the endocytic process, the LDLR releases lipoproteins into hepatic endosomes.

One approach to modulating LDL-cholesterol levels would be to identify peptides which bind to PCSK9 and alter the kinetics of the interaction between PCSK9 and the LDLR such that the rate of lipoprotein clearance by LDLR endocytosis is increased or decreased, as desired.

SUMMARY OF THE INVENTION

This invention is related to the field of hypercholesterolemia. In particular, the invention provides compositions and methods to modulate circulating levels of low density lipoproteins by altering the conformation of the protein PCSK9 using a synthetic ligand and/or a synthetic ligand derivative having sequences of 3-8 amino acids ranging between 350-2,000 Da. Altering the conformation of PCSK9 affects the interaction between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands which can raise LDL levels.

In one embodiment, the present invention contemplates a method, comprising: a) providing; i) a PCSK9 protein, wherein said protein comprises a binding site that induces allosteric modulation and a low density lipoprotein receptor binding site; ii) a ligand capable of binding said binding site; iii) a plurality of hepatocyte cells comprising a low density lipoprotein receptor and low density lipoproteins; b) binding said synthetic ligand to said binding site, wherein said synthetic ligand induces a conformation shift of said protein; and c) modulating the affinity of said low density lipoprotein receptor binding site for said low density lipoprotein receptor by said conformational shift. In one embodiment, the binding site comprises $His^{417}$, $Lys^{421}$, $Pro^{446}$, $Trp^{453}$, $Gln^{454}$, $Glu^{628}$, $Gly^{629}$, $Asn^{652}$, and $Thr^{653}$ of the PCSK9 protein (SEQ ID NO: 1). In one embodiment, the synthetic ligand is an allosteric inhibitor ligand wherein said modulating decreases the affinity of said low density lipoprotein receptor binding site for said low density lipoprotein receptor such that internalization of said low density lipoprotein by said plurality of hepatocytes is increased. In one embodiment, the synthetic ligand is an allosteric enhancer ligand said modulating increases the affinity of said low density lipoprotein receptor binding site for said low density lipoprotein receptor such that internalization of said low density lipoprotein by said plurality of hepatocytes is decreased. In one embodiment, the conformational shift of said protein is selected from the group consisting of an induced fit shift and a biomechanical shift. In one embodiment, the synthetic ligand is a synthetic peptide selected from the group consisting of VYVRFW [SEQ ID NO: 2], VLELYW [SEQ ID NO: 3] and ISDLSY [SEQ ID NO: 4]. In one embodiment, the allosteric inhibitor is a peptide is selected from the group consisting of SRX55 [SEQ ID NO: 2], SRX56 [SEQ ID NO: 5], SRX60 [SEQ ID NO: 6], SRX61 [SEQ ID NO: 7], SRX62 [SEQ ID NO: 8], SRX63 [SEQ ID NO: 9], SRX64 [SEQ ID NO: 10], SRX65 [SEQ ID NO: 3], SRX66 [SEQ ID NO: 11], SRX77 [SEQ ID NO: 163], SRX78 [SEQ ID NO: 164], SRX79 [SEQ ID NO: 165], SRX80 [SEQ ID NO: 166], SRX 81 [SEQ ID NO: 167], and SRX82 [SEQ ID NO: 168]. In one embodiment, the allosteric enhancer is a peptide is selected from the group consisting of SRX64 [SEQ ID NO: 10], SRX67 [SEQ ID NO: 12], SRX68 [SEQ ID NO: 13], SRX69 [SEQ ID NO: 14], SRX72 [SEQ ID NO: 17] and SRX73 [SEQ ID NO: 18] In one embodiment, the synthetic peptide comprises between approximately 3-8 amino acids. In one embodiment, the synthetic peptide comprises between approximately 3-8 amino acids, wherein one or more amino acids is a D-amino acid. In one embodiment, the synthetic peptide is six amino acids. In one embodiment, the synthetic peptide is six amino acids, where one or more of said six amino acids is a D-amino acid. In one embodiment the synthetic peptide is five amino acids. In one embodiment, the synthetic peptide is five amino acids, where one or more of said five amino acids is a D-amino acid. In one embodiment, the synthetic peptide is less than 1,300 Da. In one embodiment, the synthetic peptide ranges between approximately 466-1067 Da. In one embodiment, the synthetic peptide ranges between approximately 175-1,000 Da. In one embodiment, the synthetic peptide is selected from the group consisting of D-Val-D-Tyr-D-Val-D-Arg-D-Phe-D-Trp [SEQ ID NO: 163], D-Trp-D-Phe-D-Arg-D-Val-D-Tyr-D-Val [SEQ ID NO: 164], D-Arg-D-Phe-D-Trp [SEQ ID NO: 165], Ac-D-Arg-D-Phe-D-Trp [SEQ ID NO: 166], Ac-D-Arg-D-Phe-D-Trp-NH2 [SEQ ID NO: 167], and D-Trp-D-Phe-D-Arg [SEQ ID NO: 168]. In one embodiment, the synthetic compound is selected from the group consisting of Val-Tyr-Val-Arg-Phe-Trp-NH2 [SEQ ID NO: 19], Val-Tyr-Val-Cit-Phe-Trp-NH2 [SEQ ID NO: 169], Val-Tyr-Val-Cit-Phe-His [SEQ ID NO: 170], Val-Tyr-Val-Cit-Phe-His(2-Me) [SEQ ID NO: 171], Val-Tyr-Val-Cit-Phe-NH(cyclopentyl) [SEQ ID NO: 172], Val-Tyr-Val-Cit-Phe-Trp-NHMe [SEQ ID NO: 173], Val-Tyr-Val-Cit-Phe-Trp(N-Me) [SEQ ID NO: 174], Val-Tyr-His-Arg-Phe-Trp [SEQ ID NO: 175], Val-Tyr-Ala-Arg-Phe-Trp [SEQ ID NO: 176], Val-Tyr-Ser-Arg-Phe-Trp [SEQ ID NO: 177], Val-Tyr-Hse-Arg-Phe-Trp [SEQ ID NO: 178], Val-Tyr-Gly(Et)-Arg-Phe-Trp [SEQ ID NO: 179], Val-Tyr-Val-Orn-Phe-Trp [SEQ ID NO: 180], Val-Tyr-Val-Gln-Phe-Trp [SEQ ID NO: 181], Val-Tyr-Val-Glu-Phe-Trp [SEQ ID NO: 182], Val-Tyr-Val-Gln(N-propyl)-Phe-Trp [SEQ ID NO: 183], Val-Tyr-Val-Gln(N-2-hydroxylpropyl)-Phe-Trp [SEQ ID NO: 184], Val-Tyr-Val-(nor)Arg-Phe-Trp [SEQ ID NO: 185], Val-Tyr-Val-Lys-Phe-Trp [SEQ ID NO: 186], Val-Tyr-Val-Arg-Phe-Val [SEQ ID NO: 187], D-Ala-Tyr-Val-Arg-Phe-Trp [SEQ ID NO: 188], (CH3)2CHCO-Tyr-Val-Glu-Phe-Trp [SEQ ID NO: 189], (CH3)3CCO-Tyr-Val-Glu-Phe-Trp [SEQ ID NO: 190], (CH3)3CCO-Tyr-Val-Glu-Phe-NH(cyclopentyl) [SEQ ID NO: 191], Val-Phe(4-OMe)-Val-Arg-Phe(4-F)-Trp-NH2 [SEQ ID NO: 192], Phe(4-Ph)-Gly(Et)-Ser(p)-morpholine [SEQ ID NO: 193], Phe(4-Ph)-Leu-Ser(p)-morpholine [SEQ ID NO: 194], Phe(4-Ph)-Ala-Ser(p)-(4-Me-piperazine) [SEQ ID NO: 195], Phe[4-(3-OH)-Ph]-Ala-Ser(p)-morpholine [SEQ ID NO: 196]. In one embodiment, the synthetic peptide is selected from the group consisting of Ibutyryl-Tyr-Val-Arg-Phe-Trp [SEQ ID NO: 197], Pivaloyl-Tyr-Val-Arg-Phe-Trp [SEQ ID NO: 198], Gly-Val-Tyr-Val-Cit-Phe-Trp [SEQ ID NO: 199], Val-Tyr-Val-Cit_-Phe-Trp-Gly [SEQ ID NO: 200], Val-Tyr-Val-Cit-Phe-Trp(NMe) [SEQ ID NO: 201], Val-Tyr-Val-Arg-D-Phe-Trp [SEQ ID NO: 202], Ac-D-Trp-D-Ala-D-Arg-NH2 [SEQ ID NO: 203], Boc-D-Trp-D-Phe-D-Arg-NH2 [SEQ ID NO: 204], MeOCO-D-Trp-D-Phe-D-Arg-NH2 [SEQ ID NO: 205], Succ-Tyr-Val-Cit-Phe-Trp [SEQ ID NO: 206], Val-Tyr-Val-Orn-Phe-Trp-NH2 [SEQ ID NO: 207], Ac-Arg-Phe-Trp [SEQ ID NO: 208], Val-Tyr-Val-Cit-Phe-Trp-NHEt [SEQ ID NO: 209], Val-Tyr-Val-Arg-Phe-D-Trp [SEQ ID NO: 210], Val-Tyr-Val-Cit-Phe-D-Trp-NH2 [SEQ ID NO: 211], Val-D-Tyr-Val-Cit-Phe-Trp-NH2 [SEQ ID NO: 212], Val-Tyr-Val-Cit-Phe-NH2 [SEQ ID NO: 213], Val-Tyr-Val-Cit-NH2 [SEQ ID NO: 214], Val-Tyr-Val-Cit-NH(isopropyl) [SEQ ID NO: 215], Val-D-Tyr-Val-Cit-NHEt [SEQ ID NO: 216]. In one embodiment, the synthetic peptide is selected from the group consisting of Val-Tyr-Val-Arg-Phe-Trp-NH2 [SEQ ID NO: 19], Val-Tyr-Val-Arg-Phe-Trp-NHMe [SEQ ID NO: 217], Val-Tyr-Val-Arg-Phe-Trp-NHEt [SEQ ID NO: 218], Val-Tyr-Val-Arg-Phe-D-Trp-NH2 [SEQ ID NO: 219], Val-D-Tyr-Val-Arg-Phe-Trp-NH2 [SEQ ID NO: 220], Val-Tyr-Val-Arg-Phe-NH2 [SEQ ID NO: 221], Val-Tyr-Val-Arg-NH2 [SEQ ID NO: 222], Val-Tyr-Val-Arg-NH(isopropyl) [SEQ ID NO: 223], Val-D-Tyr-Val-Arg-NHEt [SEQ ID NO: 224]. In one embodiment, the synthetic peptide is selected from the group consisting of Val-Phe-Val-Arg-Phe-Trp [SEQ ID NO: 233], Val-Phe-Val-Arg-Phe-Trp-NH2 [SEQ ID NO: 225], Val-Phe-Val-Cit-Phe-Trp-NH2 [SEQ ID NO: 226], Val-Phe-Val-Cit-Phe-Trp-NH2 [SEQ ID NO: 226], Val-Phe-Val-Cit-Phe-Trp-NHMe [SEQ ID NO: 227], Val-Phe-Val-Cit-Phe-Trp-NHEt [SEQ ID NO: 228], Val-Phe-Val-Arg-Phe-NH(cyclopentyl) [SEQ ID NO: 229], Val-Phe-Val-Cit-Phe-NH(cyclopentyl) [SEQ ID NO: 230]. In one embodiment, the present invention contemplates a ligand, wherein three sequential amino acids of the synthetic ligand are selected from the group comprising of: Val-Tyr-Val, Arg-Phe-Trp, Cit-Phe-Trp, Val-(D-Tyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val. In one embodiment, the present invention contemplates a synthetic peptide ligand wherein the compound comprises an amino acid sequence of X1-X2-X3 or X3-X2-X1, wherein: X1 is an amino acid with an acidic group, an amide group, or a basic group; X2 is an amino acid with an aromatic ring; and X3 is Trp, D-Trp. In one embodiment, the present invention contemplates a synthetic peptide ligand wherein the compound comprises an amino acid sequence of X1-X2-X3 or X3-X2-X1, wherein: X1 is an amino acid selected from the group consisting of Arg, Glu, Gln, Lys, Cit, Orn, Gln(N-propyl), Gln(N-2-hydroxylpropyl). In one embodiment, the present invention contemplates a synthetic peptide ligand wherein the compound comprises an amino acid sequence of X4-X5-X6-X1-X2-X3 or X3-X2-X1-X6-X5-X4, wherein: X4 and X6 each are independently selected from the group consisting of hydrophobic amino acids; and X5 is an amino acid with an aromatic ring. In one embodiment, the present invention contemplates a synthetic peptide ligand wherein the compound comprises an amino acid sequence of X1-X2-X3 or X3-X2-X1, wherein: X1 is an amino acid with an aromatic ring; X2 and X3 are independently selected from the group comprising of Ala, Val, Gly, Ser, Thr, Phe, and Tyr.

In one embodiment, the present invention contemplates, a method, comprising: a) providing; i) a PCSK9 protein, wherein said protein comprises a binding site that induces allosteric modulation and a low density lipoprotein receptor binding site; ii) a synthetic ligand capable of binding said binding site; iii) a plurality of hepatocyte cells comprising a population of low density lipoprotein receptors; b) binding said synthetic ligand to said binding site, wherein said synthetic ligand induces a conformation shift of said protein; c) modulating said population of said low density lipoprotein receptors by said conformational shift. In one embodiment, the binding site comprises $His^{417}$, $Lys^{421}$, $Pro^{446}$, $Trp^{453}$, $Gln^{44}$, $Glu^{628}$, $Gly^{629}$, $Asn^{652}$, and $Thr^{653}$ of the PCSK9 protein [SEQ ID NO: 1]. In one embodiment, the synthetic ligand is an allosteric inhibitor ligand wherein said modulating increases said population of said low density lipoprotein receptors measurable on the cell surface of said plurality of hepatocytes. In one embodiment, the synthetic ligand is an allosteric enhancer ligand wherein said modulating decreases said population of said low density lipoprotein receptors measurable on the cell surface of said plurality of hepatocytes. In one embodiment, the conformational shift of said protein is selected from the group consisting of an induced fit shift and a biomechanical shift. In one embodiment, the ligand is a synthetic peptide selected from the group consisting of VYVRFW [SEQ ID NO: 2], VLELYW [SEQ ID NO: 3] and ISDLSY [SEQ ID NO: 4]. In one embodiment, the allosteric inhibitor peptide is selected from the group consisting of SRX55 [SEQ ID NO: 2], SRX56 [SEQ ID NO: 5], SRX60 [SEQ ID NO: 6], SRX61 [SEQ ID NO: 7], SRX62 [SEQ ID NO: 8], SRX63 [SEQ ID NO: 9], SRX64 [SEQ ID NO: 10], SRX65 [SEQ ID NO: 3], and SRX66 [SEQ ID NO: 11]. In one embodiment, the allosteric enhancer peptide is selected from the group consisting of SRX64 [SEQ ID NO: 10], SRX67 [SEQ ID NO: 12], SRX68 [SEQ ID NO: 13], SRX69 [SEQ ID NO: 14], SRX72 [SEQ ID NO: 17] and SRX73 [SEQ ID NO: 18]. In one embodiment, the synthetic peptide comprises between approximately 3-8 amino acids. In one embodiment, the synthetic peptide comprises between approximately 3-8 amino acids, wherein one or more amino acids is a D-amino acid. In one embodiment, the synthetic peptide is six amino acids. In one embodiment, the synthetic peptide is six amino acids, where one or more of said six amino acids is a D-amino acid. In one embodiment the synthetic peptide is five amino acids. In one embodiment, the synthetic peptide is five amino acids, where one or more of said five amino acids is a D-amino acid. In one embodiment, the present invention contemplates a synthetic peptide, wherein three sequential amino acids of the synthetic ligand are selected from the group comprising of: Val-Tyr-Val, Arg-Phe-Trp, Cit-Phe-Trp, Val-(D-Tyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val. In one embodiment, the present invention contemplates a synthetic peptide ligand wherein the compound comprises an amino acid sequence of X1-X2-X3 or X3-X2-X1, wherein: X1 is an amino acid with an acidic group, an amide group, or a basic group; X2 is an amino acid with an aromatic ring; and X3 is Trp, D-Trp. In one embodiment, the present invention contemplates a synthetic peptide ligand wherein the compound comprises an amino acid sequence of X1-X2-X3 or X3-X2-X1, wherein: X1 is_is an amino acid selected from the group consisting of Arg, Glu, Gln, Lys, Cit, Orn, Gln(N-propyl), Gln(N-2-hydroxylpropyl). In one embodiment, the present invention contemplates a synthetic peptide ligand wherein the compound comprises an amino acid sequence of X4-X5-X6-X1-X2-X3 or X3-X2-X1-X6-X5-X4, wherein: X4 and X6 each are independently selected from the group consisting of hydrophobic amino acids; and X5 is an amino acid with an aromatic ring. In one embodiment, the present invention contemplates a synthetic peptide ligand wherein the compound comprises an amino acid sequence of X1-X2-X3 or X3-X2-X1, wherein: X1 is an amino acid with an aromatic ring; X2 and X3 are independently selected from the group comprising of Ala, Val, Gly, Ser, Thr, Phe, and Tyr. In one embodiment, the synthetic peptide is less than 1,300 Da. In one embodiment, the synthetic peptide ranges between approximately 466-1067 Da. In one embodiment, the synthetic peptide ranges between approximately 175-1,000 Da. In one embodiment, the synthetic peptide is selected from the group consisting of D-Val-D-Tyr-D-Val-D-Arg-D-Phe-D-Trp [SEQ ID NO: 163], D-Trp-D-Phe-D-Arg-D-Val-D-Tyr-D-Val [SEQ ID NO: 164], D-Arg-D-Phe-D-Trp [SEQ ID NO: 165], Ac-D-Arg-D-Phe-D-Trp [SEQ ID NO: 166], Ac-D-Arg-D-Phe-D-Trp-NH2 [SEQ ID NO: 167], and D-Trp-D-Phe-D-Arg [SEQ ID NO: 168]. In one embodiment, the synthetic ligand is selected from the group consisting of Val-Tyr-Val-Arg-Phe-Trp-NH2 [SEQ ID NO: 19], Val-Tyr-Val-Cit-Phe-Trp-NH2 [SEQ ID NO: 169], Val-Tyr-Val-Cit-Phe-His [SEQ ID NO: 170], Val-Tyr-Val-Cit-Phe-His(2-Me) [SEQ ID NO: 171], Val-Tyr-Val-Cit-Phe-NH(cyclopentyl) [SEQ ID NO: 172], Val-Tyr-Val-Cit-Phe-Trp-NHMe [SEQ ID NO: 173], Val-Tyr-Val-Cit-Phe-Trp(N-Me) [SEQ ID NO: 174], Val-Tyr-His-Arg-Phe-Trp [SEQ ID NO: 175], Val-Tyr-Ala-Arg-Phe-Trp [SEQ ID NO: 176], Val-Tyr-Ser-Arg-Phe-Trp [SEQ ID NO: 177], Val-Tyr-Hse-Arg-Phe-Trp [SEQ ID NO: 178], Val-Tyr-Gly(Et)-Arg-Phe-Trp [SEQ ID NO: 179], Val-Tyr-Val-Orn-Phe-Trp [SEQ ID NO: 180], Val-Tyr-Val-Gln-Phe-Trp [SEQ ID NO: 181], Val-Tyr-Val-Glu-Phe-Trp [SEQ ID NO: 182], Val-Tyr-Val-Gln(N-propyl)-Phe-Trp [SEQ ID NO: 183], Val-Tyr-Val-Gln(N-2-hydroxylpropyl)-Phe-Trp [SEQ ID NO: 184], Val-Tyr-Val-(nor)Arg-Phe-Trp [SEQ ID NO: 185], Val-Tyr-Val-Lys-Phe-Trp [SEQ ID NO: 186], Val-Tyr-Val-Arg-Phe-Val [SEQ ID NO: 187], D-Ala-Tyr-Val-Arg-Phe-Trp [SEQ ID NO: 188], (CH3)2CHCO-Tyr-Val-Glu-Phe-Trp [SEQ ID NO: 189], (CH3)3CCO-Tyr-Val-Glu-Phe-Trp [SEQ ID NO: 190], (CH3)3CCO-Tyr-Val-Glu-Phe-NH(cyclopentyl) [SEQ ID NO: 191], Val-Phe(4-OMe)-Val-Arg-Phe(4-F)-Trp-NH2 [SEQ ID NO: 192], Phe(4-Ph)-Gly(Et)-Ser(p)-morpholine [SEQ ID NO: 193], Phe(4-Ph)-Leu-Ser(p)-morpholine [SEQ ID NO: 194], Phe(4-Ph)-Ala-Ser(p)-(4-Me-piperazine) [SEQ ID NO: 195], Phe[4-(3-OH)-Ph]-Ala-Ser(p)-morpholine [SEQ ID NO: 196]. In one embodiment, the synthetic peptide is selected from the group consisting of Ibutyryl-Tyr-Val-Arg-Phe-Trp [SEQ ID NO: 197], Pivaloyl-Tyr-Val-Arg-Phe-Trp [SEQ ID NO: 198], Gly-Val-Tyr-Val-Cit-Phe-Trp [SEQ ID NO: 199], Val-Tyr-Val-Cit_-Phe-Trp-Gly [SEQ ID NO: 200], Val-Tyr-Val-Cit-Phe-Trp(NMe) [SEQ ID NO: 201], Val-Tyr-Val-Arg-D-Phe-Trp [SEQ ID NO: 202], Ac-D-Trp-D-Ala-D-Arg-NH2 [SEQ ID NO: 203], Boc-D-Trp-D-Phe-D-Arg-NH2 [SEQ ID NO: 204]. MeOCO-D-Trp-D-Phe-D-Arg-NH2 [SEQ ID NO: 205], Succ-Tyr-Val-Cit-Phe-Trp [SEQ ID NO: 206], Val-Tyr-Val-Orn-Phe-Trp-NH2 [SEQ ID NO: 207], Ac-Arg-Phe-Trp [SEQ ID NO: 208], Val-Tyr-Val-Cit-Phe-Trp-NHEt [SEQ ID NO: 209], Val-Tyr-Val-Arg-Phe-D-Trp [SEQ ID NO: 210], Val-Tyr-Val-Cit-Phe-D-Trp-NH2 [SEQ ID NO: 211], Val-D-Tyr-Val-Cit-Phe-Trp-NH2 [SEQ ID NO: 212], Val-Tyr-Val-Cit-Phe-NH2 [SEQ ID NO: 213], Val-Tyr-Val-Cit-NH2 [SEQ ID NO: 214], Val-Tyr-Val-Cit-NH(isopropyl) [SEQ ID NO: 215], Val-D-Tyr-Val-Cit-NHEt [SEQ ID NO: 216]. In one embodiment, the synthetic peptide is selected from the group consisting of Val-Tyr-Val-Arg-Phe-Trp-NH2 [SEQ ID NO: 19], Val-Tyr-Val-Arg-Phe-Trp-NHMe [SEQ ID NO: 217], Val-Tyr-Val-Arg-Phe-Trp-NHEt [SEQ ID NO: 218], Val-Tyr-Val-Arg-Phe-D-Trp-NH2 [SEQ ID NO: 219], Val-D-Tyr-Val-Arg-Phe-Trp-NH2 [SEQ ID NO: 220], Val-Tyr-Val-Arg-Phe-NH2 [SEQ ID NO: 221], Val-Tyr-Val-Arg-NH2 [SEQ ID NO: 222], Val-Tyr-Val-Arg-NH(isopropyl) [SEQ ID NO: 223], Val-D-Tyr-Val-Arg-NHEt [SEQ ID NO: 224]. In one embodiment, the synthetic peptide is selected from the group consisting of Val-Phe-Val-Arg-Phe-Trp [SEQ ID NO: 233], Val-Phe-Val-Arg-Phe-Trp-NH2 [SEQ ID NO: 225], Val-Phe-Val-Cit-Phe-Trp-NH2 [SEQ ID NO: 226], Val-Phe-Val-Cit-Phe-Trp-NH2 [SEQ ID NO: 226], Val-Phe-Val-Cit-Phe-Trp-NHMe [SEQ ID NO: 227], Val-Phe-Val-Cit-Phe-Trp-NHEt [SEQ ID NO: 228], Val-Phe-Val-Arg-Phe-NH(cyclopentyl) [SEQ ID NO: 229], Val-Phe-Val-Cit-Phe-NH(cyclopentyl) [SEQ ID NO: 230].

In one embodiment, the present invention contemplates a compound of Formula I:

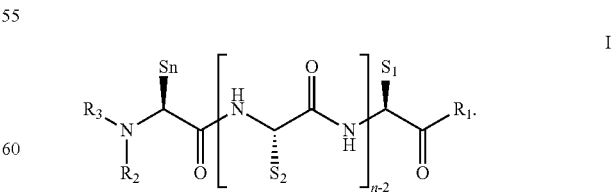

wherein: i) n, the number of amino acid residues, is an integer in the range 3-8; ii) the constituent amino acids are single enantiomers of independently selected natural or unnatural amino acids; iii) $R_2$ and $R_3$, are independently selected from the group consisting of hydrogen, a lower alkyl, a branched alkyl, a hydroxyalkyl, a cycloalkyl, a heterocycle, aryl, heteroaryl, acyl, substituted or unsubstituted benzoyl, alkyl or aryl sulfonyl, methanesulfonyl or toluenesulfonyl, and carbamoyl; iv) $R_1$ is selected from the group consisting of —OH and —NR$_4$-R$_5$; v) $R_4$ and $R_5$, independently, are selected from the group consisting of hydrogen; a lower alkyl, an aryl, a cycloalkyl, an aromatic heterocycle, pyridine, tetrazole, alkoxy; alternatively, $R_4$ and $R_5$ are joined as a heterocyle, such as piperidine; pyrrolidine; morpholine; piperazine; a substituted heterocycle, such as 4-methylpiperazine; or a fused heterocycle, such as dihydroquinoline or indoline and $S_1$, $S_2$ and $S_3$ are side chains. In one embodiment, the compound further comprises a negatively charged polar group. In one embodiment, the negatively charged polar group is selected from at least one of the group consisting of O-phosphate, O-sulfate, 5-O-, and a 5-N-tetrazole incorporated in said side-chains $S_1$, $S_2$, or $S_n$. In one embodiment, the side chain selected from the group consisting of $S_1$, $S_2$ and $S_n$ comprises a phosphoserine. In one embodiment, the side chain $S_1$ comprises —CH2-NH-tetrazole. In one embodiment, the compound further comprises a glycine C-terminus. In one embodiment, the compound comprises between approximately 3-8 amino acids. In one embodiment, the compound is six amino acids. In one embodiment, the present invention contemplates a compound of Formula I, wherein three sequential amino acids of the synthetic ligand are selected from the group comprising of: Val-Tyr-Val, Arg-Phe-Trp, Cit-Phe-Trp, Val-(D-Tyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val. In one embodiment, the compound is less than 1,300 Da. In one embodiment, the compound ranges between approximately 466-1067 Da. In one embodiment, the compound ranges between approximately 175-1,000 Da.

In one embodiment, the present invention contemplates a compound of the Formula II:

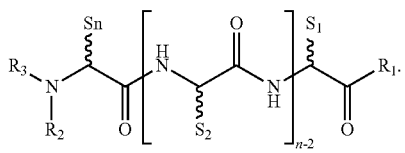

wherein: i) n, the number of amino acid residues, is an integer in the range 3-8, wherein one or more of said amino acids residues is a D-amino acid residue; ii) the constituent amino acids are single enantiomers of independently selected natural or unnatural amino acids; iii) $R_2$ and $R_3$, are independently selected from the group consisting of hydrogen, a lower alkyl, a branched alkyl, a hydroxyalkyl, a cycloalkyl, a heterocycle, aryl, heteroaryl, acyl, substituted or unsubstituted benzoyl, alkyl or aryl sulfonyl, methanesulfonyl or toluenesulfonyl, and carbamoyl; iv) $R_1$ is selected from the group consisting of —OH and —NR$_4$-R$_5$; v) $R_4$ and $R_5$, independently, are selected from the group consisting of hydrogen; a lower alkyl, an aryl, a cycloalkyl, an aromatic heterocycle, pyridine, tetrazole; alternatively, $R_4$ and $R_5$ are joined as a heterocycle, such as piperidine; pyrrolidine; morpholine; piperazine; a substituted heterocycle, such as 4-methylpiperazine; or a fused heterocycle, such as dihydroquinoline or indoline. In one embodiment, the compound further comprises a negatively charged polar group. In one embodiment, said negatively charged polar group is selected from at least one of the group consisting of O-phosphate, O-sulfate, or 5-O- or 5-N-tetrazole incorporated in the side-chain $S_1$, $S_2$, or $S_3$. In one embodiment, the side chain $S_1$, $S_2$ or $S_3$ comprises a phosphoserine. In one embodiment, the side chain $S_1$ comprises —CH2-NH-tetrazole. In one embodiment, the C-terminus comprises a glycine. In one embodiment, the compound comprises between approximately 3-8 amino acids. In one embodiment, the compound is six amino acids. In one embodiment, the present invention contemplates a compound of Formula II, wherein three sequential amino acids of the synthetic ligand are selected from the group comprising of: Val-Tyr-Val, Arg-Phe-Trp, Cit-Phe-Trp, Val-(D-Tyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val. In one embodiment, the compound is less than 1,300 Da. In one embodiment, the compound ranges between approximately 466-1067 Da. In one embodiment, the compound ranges between approximately 175-1,000 Da.

In one embodiment, the present invention contemplates the ligand as a compound of the Formula I:

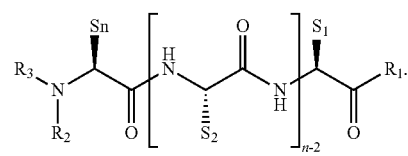

wherein: i) n, the number of amino acid residues, is an integer in the range 3-8; ii) the constituent amino acids are single enantiomers of independently selected natural or unnatural amino acids; iii) $R_2$ and $R_3$, are independently selected from the group consisting of hydrogen, a lower alkyl, a branched alkyl, a hydroxyalkyl, a cycloalkyl, a heterocycle, aryl, heteroaryl, acyl, substituted or unsubstituted benzoyl, alkyl or aryl sulfonyl, methanesulfonyl or toluenesulfonyl, and carbamoyl; iv) $R_1$ is selected from the group consisting of —OH and —NR$_4$-R$_5$; v) $R_4$ and $R_5$, independently, are selected from the group consisting of hydrogen; a lower alkyl, an aryl, a cycloalkyl, an aromatic heterocycle, pyridine, tetrazole, alkoxy; alternatively, $R_4$ and $R_5$ are joined as a heterocyle, such as piperidine; pyrrolidine; morpholine; piperazine; a substituted heterocycle, such as 4-methylpiperazine; or a fused heterocycle, such as dihydroquinoline or indoline and $S_1$, $S_2$ and $S_3$ are side chains. In one embodiment, the compound further comprises a negatively charged polar group. In one embodiment, the negatively charged polar group is selected from at least one of the group consisting of O-phosphate, O-sulfate, 5-O-, and a 5-N-tetrazole incorporated in said side-chains $S_1$, $S_2$, or $S_n$. In one embodiment, the side chain selected from the group consisting of $S_1$, $S_2$ and $S_n$ comprises a phosphoserine. In one embodiment, the side chain $S_1$ comprises —CH2-NH-tetrazole. In one embodiment, the compound further comprises a glycine C-terminus. In one embodiment, the compound comprises between approximately 3-8 amino acids. In one embodiment, the compound is six amino acids. In one embodiment, the present invention contemplates a ligand of Formula I, wherein three sequential amino acids of the synthetic ligand are selected from the group comprising of: Val-Tyr-Val, Arg-Phe-Trp, Cit-Phe-Trp, Val-(D-Tyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val. In one embodiment, the compound is less than 1,300 Da. In one embodiment, the compound ranges between approximately 466-1067 Da. In one embodiment, the compound ranges between approximately 175-1,000 Da.

In one embodiment, the present invention contemplates the ligand as a compound of the Formula II:

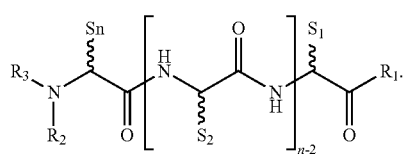

wherein: i) n, the number of amino acid residues, is an integer in the range 3-8, wherein one or more of said amino acids residues is a D-amino acid residue; ii) the constituent amino acids are single enantiomers of independently selected natural or unnatural amino acids; iii) $R_2$ and $R_3$, are independently selected from the group consisting of hydrogen, a lower alkyl, a branched alkyl, a hydroxyalkyl, a cycloalkyl, a heterocycle, aryl, heteroaryl, acyl, substituted or unsubstituted benzoyl, alkyl or aryl sulfonyl, methanesulfonyl or toluenesulfonyl, and carbamoyl; iv) $R_1$ is selected from the group consisting of —OH and —$NR_4$-$R_5$; v) $R_4$ and $R_5$, independently, are selected from the group consisting of hydrogen; a lower alkyl, an aryl, a cycloalkyl, an aromatic heterocycle, pyridine, tetrazole; alternatively, $R_4$ and $R_5$ are joined as a heterocycle, such as piperidine; pyrrolidine; morpholine; piperazine; a substituted heterocycle, such as 4-methylpiperazine; or a fused heterocycle, such as dihydroquinoline or indoline. In one embodiment, the compound further comprises a negatively charged polar group. In one embodiment, said negatively charged polar group is selected from at least one of the group consisting of O-phosphate, O-sulfate, or 5-O- or 5-N-tetrazole incorporated in the side-chain $S_1$, $S_2$, or $S_3$. In one embodiment, the side chain $S_1$, $S_2$ or $S_3$ comprises a phosphoserine. In one embodiment, the side chain $S_1$ comprises —CH2-NH-tetrazole. In one embodiment, the C-terminus comprises a glycine. In one embodiment, the compound comprises between approximately 3-8 amino acids. In one embodiment, the compound is six amino acids. In one embodiment, the present invention contemplates a ligand of Formula II, wherein three sequential amino acids of the synthetic ligand are selected from the group comprising of: Val-Tyr-Val, Arg-Phe-Trp, Cit-Phe-Trp, Val-(D-Tyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val. In one embodiment, the compound is less than 1,300 Da. In one embodiment, the compound ranges between approximately 466-1067 Da. In one embodiment, the compound ranges between approximately 175-1,000 Da.

In one embodiment, the compound is selected from the group consisting of Val-Tyr-Val-Arg-Phe-Trp [SEQ ID NO: 2], β-Ala-Phe(3-CH2NH2)-Val-D-Ser(p)-Phe-Trp [SEQ ID NO: 5]. Thr-Leu-Cys(CH2-Ph)-Thr-Trp-Ser-Ser-Ser(p) [SEQ ID NO: 6], Thr-Leu-Asp(NHCH2Ph)-Thr-Trp-Ser-Ser-Ser(p) [SEQ ID NO: 7], Thr-Leu-Gly(CH2CH2cyclohexyl)-Thr-Trp-Ser-Ser-Ser(p) [SEQ ID NO: 8], Thr-Leu-Hph-Thr-Trp-Ser-Ser-Ser(p) [SEQ ID NO: 9], Thr-Leu-Cys(CH2-Ph)-Thr-Trp(3-Me)-Ser-Ser-Ser(p) [SEQ ID NO: 10], Val-Leu-Glu-Leu-Tyr-Trp [SEQ ID NO: 3], Leu-Asp-Leu-Phe-Phe-Ser [SEQ ID NO: 11], Ile-Leu-Asp-Leu-Ser-Tyr [SEQ ID NO: 12], Ac-Trp-Ser-Ser(p) [SEQ ID NO: 13], Ac-Trp-Ala-Ser(p) [SEQ ID NO: 14], Ac-Trp(5-F)-Ala-Ser(p)-morpholine [SEQ ID NO: 15], Thr-Leu-Thr-Trp-Ser-Ser-Ser(p) [SEQ ID NO: 16], Ac-Tyr-Trp-Gly [SEQ ID NO: 17], Phe(4-Ph)-Ala-Ser(p)-morpholine [SEQ ID NO: 18]. In one embodiment, the present invention contemplates a compound selected from the group consisting of D-Val-D-Tyr-D-Val-D-Arg-D-Phe-D-Trp [SEQ ID NO: 163], D-Trp-D-Phe-D-Arg-D-Val-D-Tyr-D-Val [SEQ ID NO: 164], D-Arg-D-Phe-D-Trp [SEQ ID NO: 165], Ac-D-Arg-D-Phe-D-Trp [SEQ ID NO: 166], Ac-D-Arg-D-Phe-D-Trp-NH2 [SEQ ID NO: 167], and D-Trp-D-Phe-D-Arg [SEQ ID NO: 168].

In one embodiment, the present invention contemplates a compound including, but not limited to, Val-Tyr-Val-Arg-Phe-Trp-NH2 [SEQ ID NO: 19], Val-Tyr-Val-Cit-Phe-Trp-NH2 [SEQ ID NO: 169], Val-Tyr-Val-Cit-Phe-His [SEQ ID NO: 170], Val-Tyr-Val-Cit-Phe-His(2-Me) [SEQ ID NO: 171], Val-Tyr-Val-Cit-Phe-NH(cyclopentyl) [SEQ ID NO: 172], Val-Tyr-Val-Cit-Phe-Trp-NHMe [SEQ ID NO: 173], Val-Tyr-Val-Cit-Phe-Trp(N-Me) [SEQ ID NO: 174].

In one embodiment, the present invention contemplates a compound including, but not limited to, Val-Tyr-His-Arg-Phe-Trp [SEQ ID NO: 175], Val-Tyr-Ala-Arg-Phe-Trp [SEQ ID NO: 176], Val-Tyr-Ser-Arg-Phe-Trp [SEQ ID NO: 177], Val-Tyr-Hse-Arg-Phe-Trp [SEQ ID NO: 178], Val-Tyr-Gly(Et)-Arg-Phe-Trp [SEQ ID NO: 179].

In one embodiment, the present invention contemplates a compound including, but not limited to, Val-Tyr-Val-Orn-Phe-Trp [SEQ ID NO: 180], Val-Tyr-Val-Gln-Phe-Trp [SEQ ID NO: 181], Val-Tyr-Val-Glu-Phe-Trp [SEQ ID NO: 182], Val-Tyr-Val-Gln(N-propyl)-Phe-Trp [SEQ ID NO: 183], Val-Tyr-Val-Gln(N-2-hydroxylpropyl)-Phe-Trp [SEQ ID NO: 184], Val-Tyr-Val-(nor)Arg-Phe-Trp [SEQ ID NO: 185], Val-Tyr-Val-Lys-Phe-Trp [SEQ ID NO: 186].

In one embodiment, the present invention contemplates a compound of the formula: Val-Tyr-Val-Arg-Phe-Val [SEQ ID NO: 187].

In one embodiment, the present invention contemplates a compound including, but not limited to, D-Ala-Tyr-Val-Arg-Phe-Trp [SEQ ID NO: 188], (CH3)2CHCO-Tyr-Val-Glu-Phe-Trp [SEQ ID NO: 189], (CH3)3CCO-Tyr-Val-Glu-Phe-Trp [SEQ ID NO: 190].

In one embodiment, the present invention contemplates a compound including, but not limited to, (CH3)3CCO-Tyr-Val-Glu-Phe-NH(cyclopentyl) [SEQ ID NO: 191], Val-Phe(4-OMe)-Val-Arg-Phe(4-F)-Trp-NH2 [SEQ ID NO: 192].

In one embodiment, the present invention contemplates a compound including, but not limited to, Phe(4-Ph)-Gly(Et)-Ser(p)-morpholine [SEQ ID NO: 193], Phe(4-Ph)-Leu-Ser(p)-morpholine [SEQ ID NO: 194], Phe(4-Ph)-Ala-Ser(p)-(4-Me-piperazine) [SEQ ID NO: 195], Phe[4-(3-OH)-Ph]-Ala-Ser(p)-morpholine [SEQ ID NO: 196].

In one embodiment, the present invention contemplates a compound selected from the group consisting of Val-Tyr-Val-Arg-Phe-Trp-NH2 [SEQ ID NO: 19], Val-Tyr-Val-Cit-Phe-Trp-NH2 [SEQ ID NO: 169], Val-Tyr-Val-Cit-Phe-His [SEQ ID NO: 170], Val-Tyr-Val-Cit-Phe-His(2-Me) [SEQ ID NO: 171], Val-Tyr-Val-Cit-Phe-NH(cyclopentyl) [SEQ ID NO: 172], Val-Tyr-Val-Cit-Phe-Trp-NHMe [SEQ ID NO: 173], Val-Tyr-Val-Cit-Phe-Trp(N-Me) [SEQ ID NO: 174], Val-Tyr-His-Arg-Phe-Trp [SEQ ID NO: 175], Val-Tyr-Ala-Arg-Phe-Trp [SEQ ID NO: 176], Val-Tyr-Ser-Arg-Phe-Trp [SEQ ID NO: 177], Val-Tyr-Hse-Arg-Phe-Trp [SEQ ID NO: 178], Val-Tyr-Gly(Et)-Arg-Phe-Trp [SEQ ID NO: 179], Val-Tyr-Val-Orn-Phe-Trp [SEQ ID NO: 180], Val-Tyr-Val-Gln-Phe-Trp [SEQ ID NO: 181], Val-Tyr-Val-Glu-Phe-Trp [SEQ ID NO: 182], Val-Tyr-Val-Gln(N-propyl)-Phe-Trp [SEQ ID NO: 183], Val-Tyr-Val-Gln(N-2-hydroxylpropyl)-Phe-Trp

[SEQ ID NO: 184], Val-Tyr-Val-(nor)Arg-Phe-Trp [SEQ ID NO: 185], Val-Tyr-Val-Lys-Phe-Trp [SEQ ID NO: 186], Val-Tyr-Val-Arg-Phe-Val [SEQ ID NO: 187], D-Ala-Tyr-Val-Arg-Phe-Trp [SEQ ID NO: 188], (CH3)2CHCO-Tyr-Val-Glu-Phe-Trp [SEQ ID NO: 189], (CH3)3CCO-Tyr-Val-Glu-Phe-Trp [SEQ ID NO: 190], (CH3)3CCO-Tyr-Val-Glu-Phe-NH(cyclopentyl) [SEQ ID NO: 191], Val-Phe(4-OMe)-Val-Arg-Phe(4-F)-Trp-NH2 [SEQ ID NO: 192], Phe(4-Ph)-Gly(Et)-Ser(p)-morpholine [SEQ ID NO: 193], Phe(4-Ph)-Leu-Ser(p)-morpholine [SEQ ID NO: 194], Phe(4-Ph)-Ala-Ser(p)-(4-Me-piperazine) [SEQ ID NO: 195], Phe[4-(3-OH)-Ph]-Ala-Ser(p)-morpholine [SEQ ID NO: 196].

In one embodiment, the present invention contemplates a compound selected from the group consisting of Ibutyryl-Tyr-Val-Arg-Phe-Trp [SEQ ID NO: 197], Pivaloyl-Tyr-Val-Arg-Phe-Trp [SEQ ID NO: 198], Gly-Val-Tyr-Val-Cit-Phe-Trp [SEQ ID NO: 199], Val-Tyr-Val-Cit_-Phe-Trp-Gly [SEQ ID NO: 200], Val-Tyr-Val-Cit-Phe-Trp(NMe) [SEQ ID NO: 201], Val-Tyr-Val-Arg-D-Phe-Trp [SEQ ID NO: 202], Ac-D-Trp-D-Ala-D-Arg-NH2 [SEQ ID NO: 203], Boc-D-Trp-D-Phe-D-Arg-NH2 [SEQ ID NO: 204], MeOCO-D-Trp-D-Phe-D-Arg-NH2 [SEQ ID NO: 205], Succ-Tyr-Val-Cit-Phe-Trp [SEQ ID NO: 206], Val-Tyr-Val-Orn-Phe-Trp-NH2, Ac-Arg-Phe-Trp [SEQ ID NO: 208].

In one embodiment, the present invention contemplates a compound selected from the group consisting of Val-Phe-Val-Arg-Phe-Trp [SEQ ID NO: 233], Val-Phe-Val-Arg-Phe-Trp-NH2 [SEQ ID NO: 225], Val-Phe-Val-Cit-Phe-Trp-NH2 [SEQ ID NO: 226], Val-Phe-Val-Cit-Phe-Trp-NH2 [SEQ ID NO: 226], Val-Phe-Val-Cit-Phe-Trp-NHMe [SEQ ID NO: 227], Val-Phe-Val-Cit-Phe-Trp-NHEt [SEQ ID NO: 228], Val-Phe-Val-Arg-Phe-NH(cyclopentyl) [SEQ ID NO: 229], Val-Phe-Val-Cit-Phe-NH(cyclopentyl) [SEQ ID NO: 230].

In one embodiment, the compound comprises between approximately 3-8 amino acids. In one embodiment, the compound is six amino acids. In one embodiment, the compound is less than 1,300 Da. In one embodiment, the compound ranges between approximately 466-1,067 Da. In one embodiment, the compound ranges between approximately 175-1,000 Da.

In one embodiment, the present invention contemplates a pharmaceutical composition comprising a compound of Formula I:

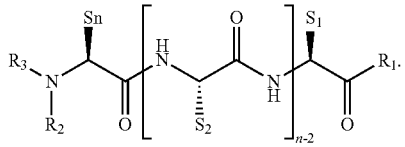

I and a carrier, wherein: i) n, the number of amino acid residues, is an integer in the range 3-8; ii) the constituent amino acids are single enantiomers of independently selected natural or unnatural amino acids; iii) $R_2$ and $R_3$, are independently selected from the group consisting of hydrogen, a lower alkyl, a branched alkyl, a hydroxyalkyl, a cycloalkyl, a heterocycle, aryl, heteroaryl, acyl, substituted or unsubstituted benzoyl, alkyl or aryl sulfonyl, methanesulfonyl or toluenesulfonyl, and carbamoyl; iv) $R_1$ is selected from the group consisting of —OH and —NR$_4$-R$_5$; v) $R_4$ and $R_5$, independently, are selected from the group consisting of hydrogen; a lower alkyl, an aryl, a cycloalkyl, an aromatic heterocycle, pyridine, tetrazole; alternatively, $R_4$ and $R_5$ are joined as a heterocycle, such as piperidine; pyrrolidine; morpholine; piperazine; a substituted heterocycle, such as 4-methylpiperazine; or a fused heterocycle, such as dihydroquinoline or indoline. In one embodiment, the pharmaceutical composition further comprises a negatively charged polar group. In one embodiment, said negatively charged polar group is selected from at least one of the group consisting of O-phosphate, O-sulfate, or 5-O- or 5-N-tetrazole incorporated in the side-chain $S_1$, $S_2$, or $S_3$. In one embodiment, the side chain $S_1$, $S_2$ or $S_3$ comprises a phosphoserine. In one embodiment, the side chain $S_1$ comprises —CH2-NH-tetrazole. In one embodiment, the C-terminus comprises a glycine. In one embodiment, the pharmaceutical composition further comprises a statin. In one embodiment, the statin includes, but is not limited to, atorvastatin, rosuvastatin and/or simvastatin. In one embodiment, the pharmaceutical composition comprises an anti-diabetic drug. In one embodiment, the pharmaceutical composition comprises a cardiovascular drug. In one embodiment, the pharmaceutical composition comprises ezetimibe (Zetia®). In one embodiment, the pharmaceutical composition comprises an anti-hypertensive including, but not limited to, amlodipine besylate (Norvasc®). In one embodiment the anti-diabetic drug includes, but is not limited to, sitagliptin (Januvia®) and/or metformin. In one embodiment, the compound comprises between approximately 3-8 amino acids. In one embodiment, the compound is six amino acids. In one embodiment, the present invention contemplates a compound of Formula I, wherein three sequential amino acids of the synthetic ligand are selected from the group comprising of: Val-Tyr-Val, Arg-Phe-Trp, Cit-Phe-Trp, Val-(D-Tyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val. In one embodiment, the compound is less than 1,300 Da. In one embodiment, the compound ranges between approximately 466-1067 Da. In one embodiment, the compound ranges between approximately 175-1,000 Da. In one embodiment, the compound comprises a synthetic peptide.

In one embodiment, the present invention contemplates a pharmaceutical composition comprising a compound of Formula II:

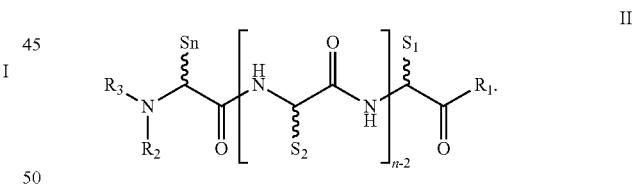

II and a carrier, wherein: i) n, the number of amino acid residues, is an integer in the range 3-8, wherein one or more of said amino acids residues is a D-amino acid residue; ii) the constituent amino acids are single enantiomers of independently selected natural or unnatural amino acids; iii) $R_2$ and $R_3$, are independently selected from the group consisting of hydrogen, a lower alkyl, a branched alkyl, a hydroxyalkyl, a cycloalkyl, a heterocycle, aryl, heteroaryl, acyl, substituted or unsubstituted benzoyl, alkyl or aryl sulfonyl, methanesulfonyl or toluenesulfonyl, and carbamoyl; iv) $R_1$ is selected from the group consisting of —OH and —NR$_4$-R$_5$; v) $R_4$ and $R_5$, independently, are selected from the group consisting of hydrogen; a lower alkyl, an aryl, a cycloalkyl, an aromatic heterocycle, pyridine, tetrazole; alternatively, $R_4$ and $R_5$ are joined as a heterocycle, such as piperidine; pyrrolidine; morpholine; piperazine; a substituted heterocycle, such as 4-methylpiperazine; or a fused heterocycle, such as dihydroquinoline or indoline. In one embodiment, the pharmaceutical composition further comprises a negatively charged polar group. In one embodiment, said negatively charged polar group is selected from at least one of the group consisting of O-phosphate, O-sulfate, or 5-O- or 5-N-tetrazole incorporated in the side-chain $S_1$, $S_2$, or $S_3$. In one embodiment, the side chain $S_1$, $S_2$ or $S_3$ comprises a phosphoserine. In one embodiment, the side chain $S_1$ comprises —CH2-NH-tetrazole. In one embodiment, the C-terminus comprises a glycine. In one embodiment, the present invention contemplates a compound of Formula II, wherein three sequential amino acids of the synthetic ligand are selected from the group comprising of: Val-Tyr-Val, Arg-Phe-Trp, Cit-Phe-Trp, Val-(D-Tyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val.

In one embodiment, the pharmaceutical composition further comprises a statin. In one embodiment, the statin includes, but is not limited to, atorvastatin, rosuvastatin and/or simvastatin. In one embodiment, the pharmaceutical composition comprises an anti-diabetic drug. In one embodiment, the pharmaceutical composition comprises a cardiovascular drug. In one embodiment, the pharmaceutical composition comprises ezetimibe (Zetia®). In one embodiment, the pharmaceutical composition comprises an anti-hypertensive including, but not limited to, amlodipine besylate (Norvasc®). In one embodiment the anti-diabetic drug includes, but is not limited to, sitagliptin (Januvia®) and/or metformin. In one embodiment, the compound comprises between approximately 3-8 amino acids, wherein one or more of said approximately 3-8 amino acids is a D-amino acid. In one embodiment, the compound is six amino acids. In one embodiment, the compound is less than 1,300 Da. In one embodiment, the compound ranges between approximately 466-1067 Da. In one embodiment, the compound ranges between approximately 175-1,000 Da. In one embodiment, the compound comprises a synthetic peptide.

In one embodiment, the compound comprises a synthetic peptide. In one embodiment, the compound is formulated as a pharmaceutical composition. In one embodiment, the pharmaceutical composition further comprises a pharmaceutical drug. In one embodiment, the pharmaceutical drug is selected from the group consisting of a statin, a cardiovascular drug, a metabolic drug, and an antihypertensive drug. In one embodiment, the pharmaceutical drug is selected from the group consisting of ezetimibe, amlodipine besylate, sitagliptin, metformin, atorvastatin, rosuvastatin and simvastatin. In one embodiment, the pharmaceutical composition is formulated as selected from the group consisting of a tablet, a liquid, a gel, a capsule, a sachet, a microparticle, a liposome, a nanoparticle, a salt, a transdermal patch, an ointment, a lotion, a cream, a gel, a drop, a strip, a suppository, a spray and a powder.

In one embodiment, the present invention contemplates a composition comprising a PCSK9 allosteric ligand ranging between approximately 350-1,500 Da. In one embodiment, the PCSK9 allosteric ligand is less than 1,300 Da. In one embodiment, the PCSK9 allosteric ligand comprises between approximately 3-6 amino acids. In one embodiment, the PCSK9 allosteric ligand ranges between approximately 550-1,000 Da. In one embodiment, the composition is a pharmaceutical composition. In one embodiment, the composition is a pharmaceutical composition for administration to a patient. In one embodiment, said administering further comprises a delivery system selected from the group including, but not limited to, liposomes, microparticles and nanoparticles. In one embodiment, the pharmaceutical composition comprises an effective dose of said ligand. In one embodiment, the pharmaceutical composition comprises salts. In one embodiment, the pharmaceutical composition is formulated for oral administration.

In one embodiment, the present invention contemplates a PCSK9 allosteric ligand that comprises between approximately 3-6 amino acids of which one or more is a D-amino acid. In one embodiment, the composition is a pharmaceutical composition. In one embodiment, the pharmaceutical composition comprises an effective dose of said ligand. In one embodiment, the pharmaceutical composition comprises salts. In one embodiment, the pharmaceutical composition is formulated for oral administration.

In one embodiment, the present invention contemplates a method, comprising: a) administering a PCSK9 allosteric inhibitor peptide to a subject, wherein said subject has at least one symptom of a cardiovascular disease; and b) reducing said at least one symptom of cardiovascular disease by said PCSK9 allosteric inhibitor peptide administration. In one embodiment, said at least one symptom is reduced between 10%-85%. In one embodiment, said at least one symptom is reduced between 20%-65%. In one embodiment, said at least one symptom is reduced between 30%-55%. In one embodiment, the cardiovascular disease comprises a coronary disease. In one embodiment, the cardiovascular disease comprises hypertension. In one embodiment, the cardiovascular disease comprises hypercholesterolemia. In one embodiment, the cardiovascular disease comprises atherosclerosis. In one embodiment, the at least one symptom comprises reduced circulating high density lipoprotein. In one embodiment, the at least one symptom comprises elevated circulating cholesterol. In one embodiment, the at least one symptom comprises elevated circulating low density lipoprotein. In one embodiment, the at least one symptom comprises high blood pressure. In one embodiment, the administering comprises an effective dose of said PCSK9 allosteric inhibitor peptide. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment, the allosteric inhibitor peptide comprises between approximately 3-8 amino acids. In one embodiment, the allosteric inhibitor peptide is six amino acids. In one embodiment, the allosteric inhibitor peptide is less than 1,300 Da. In one embodiment, the allosteric inhibitor peptide ranges between approximately 466-1067 Da. In one embodiment, the allosteric inhibitor peptide ranges between approximately 175-1,000 Da. In one embodiment the peptide comprises between 3-8 amino acids and contains one or more D-amino acids. In one embodiment, the allosteric inhibitor peptide is six amino acids, wherein one or more of said six amino acids is a D-amino acid. In one embodiment the peptide is selected from the group consisting of Ibutyryl-Tyr-Val-Arg-Phe-Trp [SEQ ID NO: 197], Pivaloyl-Tyr-Val-Arg-Phe-Trp [SEQ ID NO: 198], Gly-Val-Tyr-Val-Cit-Phe-Trp [SEQ ID NO: 199], Val-Tyr-Val-Cit_-Phe-Trp-Gly [SEQ ID NO: 200], Val-Tyr-Val-Cit-Phe-Trp(NMe) [SEQ ID NO: 201], Val-Tyr-Val-Arg-D-Phe-Trp [SEQ ID NO: 202], Ac-D-Trp-D-Ala-D-Arg-NH2 [SEQ ID NO: 203], Boc-D-Trp-D-Phe-D-Arg-NH2 [SEQ ID NO: 204], MeOCO-D-Trp-D-Phe-D-Arg-NH2 [SEQ ID NO: 205], Succ-Tyr-Val-Cit-Phe-Trp [SEQ ID NO: 206], Val-Tyr-Val- Orn-Phe-Trp-NH2 [SEQ ID NO: 207], Ac-Arg-Phe-Trp [SEQ ID NO: 208], Val-Tyr-Val-Cit-Phe-Trp-NH2 [SEQ ID NO: 169], Val-Tyr-Val-Cit-Phe-Trp-NHMe [SEQ ID NO: 173], Val-Tyr-Val-Cit-Phe-Trp-NHEt [SEQ ID NO: 209], Val-Tyr-Val-Cit-Phe-Trp-NH(propyl) [SEQ ID NO: 231], Val-Tyr-Val-Cit-Phe-Trp-NH(isopropyl) [SEQ ID NO: 232], Val-Tyr-Val-Arg-Phe-D-Trp [SEQ ID NO: 210], Val-Tyr-Val-Cit-Phe-D-Trp-NH2 [SEQ ID NO: 211], Val-D-Tyr-Val-Cit-Phe-Trp-NH2 [SEQ ID NO: 212], Val-Tyr-Val-Cit-Phe-NH2 [SEQ ID NO: 213], Val-Tyr-Val-Cit-NH2 [SEQ ID NO: 214], Val-Tyr-Val-Cit-NH(isopropyl) [SEQ ID NO: 215], Val-D-Tyr-Val-Cit-NHEt [SEQ ID NO: 216]. In one embodiment, the synthetic peptide is selected from the group consisting of Val-Tyr-Val-Arg-Phe-Trp-NH2 [SEQ ID NO: 19], Val-Tyr-Val-Arg-Phe-Trp-NHMe [SEQ ID NO: 217], Val-Tyr-Val-Arg-Phe-Trp-NHEt [SEQ ID NO: 218], Val-Tyr-Val-Arg-Phe-D-Trp-NH2 [SEQ ID NO: 219], Val-D-Tyr-Val-Arg-Phe-Trp-NH2 [SEQ ID NO: 220], Val-Tyr-Val-Arg-Phe-NH2 [SEQ ID NO: 221], Val-Tyr-Val-Arg-NH2 [SEQ ID NO: 222], Val-Tyr-Val-Arg-NH(isopropyl) [SEQ ID NO: 223], Val-D-Tyr-Val-Arg-NHEt [SEQ ID NO: 224].

In one embodiment, the synthetic peptide is selected from the group consisting of Val-Phe-Val-Arg-Phe-Trp [SEQ ID NO: 233], Val-Phe-Val-Arg-Phe-Trp-NH2 [SEQ ID NO: 225], Val-Phe-Val-Cit-Phe-Trp-NH2 [SEQ ID NO: 226], Val-Phe-Val-Cit-Phe-Trp-NH2 [SEQ ID NO: 226], Val-Phe-Val-Cit-Phe-Trp-NHMe [SEQ ID NO: 227], Val-Phe-Val-Cit-Phe-Trp-NHEt [SEQ ID NO: 228], Val-Phe-Val-Arg-Phe-NH(cyclopentyl) [SEQ ID NO: 229], Val-Phe-Val-Cit-Phe-NH(cyclopentyl) [SEQ ID NO: 230].

In one embodiment, the present invention contemplates a method, comprising: a) administering a PCSK9 allosteric enhancer peptide to a subject, wherein said subject has at least one symptom of a cardiovascular disease; and b) reducing said at least one symptom of cardiovascular disease by said PCSK9 allosteric enhancer peptide administration. In one embodiment, the cardiovascular disease comprises hypocholesterolemia. In one embodiment, said at least one symptom comprises reduced circulating cholesterol. In one embodiment, said at least one symptom comprises reduced high density lipoprotein. In one embodiment, the at least one symptom comprises reduced low density lipoprotein. In one embodiment, the at least one symptom comprises low blood pressure. In one embodiment, said at least one symptom is reduced between 10%-85%. In one embodiment, said at least one symptom is reduced between 20%-65%. In one embodiment, said at least one symptom is reduced between 30%-55%. In one embodiment, the administering comprises an effective dose of said PCSK9 allosteric enhancer peptide. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment, the allosteric enhancer peptide comprises between approximately 3-8 amino acids. In one embodiment, the allosteric enhancer peptide is six amino acids. In one embodiment, the allosteric enhancer peptide is less than 1,300 Da. In one embodiment, the allosteric enhancer peptide ranges between approximately 466-1067 Da. In one embodiment, the allosteric enhancer peptide ranges between approximately 175-1,000 Da.

In one embodiment, the present invention contemplates a method, comprising: a) administering a PCSK9 allosteric synthetic peptide to a subject, wherein said subject has at least one symptom of a liver disease; and b) reducing said at least one symptom of liver disease by said PCSK9 allosteric peptide administration. In one embodiment, the at least one symptom comprises elevated low density lipoprotein receptor density. In one embodiment the at least one symptom comprises reduced low density lipoprotein receptor density. In one embodiment, said at least one symptom is reduced between 10%-85%. In one embodiment, said at least one symptom is reduced between 20%-65%. In one embodiment, said at least one symptom is reduced between 30%-55%. In one embodiment, the PCSK9 allosteric synthetic peptide comprises a PCSK9 allosteric enhancer peptide. In one embodiment, the PCSK9 allosteric synthetic peptide comprises a PCSK9 allosteric inhibitor peptide. In one embodiment, the administering comprises an effective dose of said PCSK9 allosteric peptide. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment, the allosteric synthetic peptide comprises between approximately 3-8 amino acids. In one embodiment, the allosteric synthetic peptide is six amino acids. In one embodiment, the allosteric synthetic peptide is less than 1,300 Da. In one embodiment, the allosteric synthetic peptide ranges between approximately 466-1067 Da. In one embodiment, the allosteric synthetic peptide ranges between approximately 175-1,000 Da. In one embodiment the peptide comprises between 3-8 amino acids and contains one or more D-amino acids. In one embodiment, the allosteric inhibitor peptide is six amino acids, wherein one or more of said six amino acids is a D-amino acid. In one embodiment the peptide is selected from the group consisting of Ibutyryl-Tyr-Val-Arg-Phe-Trp [SEQ ID NO: 197], Pivaloyl-Tyr-Val-Arg-Phe-Trp [SEQ ID NO: 198], Gly-Val-Tyr-Val-Cit-Phe-Trp [SEQ ID NO: 199], Val-Tyr-Val-Cit_-Phe-Trp-Gly [SEQ ID NO: 200], Val-Tyr-Val-Cit-Phe-Trp(NMe) [SEQ ID NO: 201], Val-Tyr-Val-Arg-D-Phe-Trp [SEQ ID NO: 202], Ac-D-Trp-D-Ala-D-Arg-NH2 [SEQ ID NO: 203], Boc-D-Trp-D-Phe-D-Arg-NH2 [SEQ ID NO: 204], MeOCO-D-Trp-D-Phe-D-Arg-NH2 [SEQ ID NO: 205], Succ-Tyr-Val-Cit-Phe-Trp [SEQ ID NO: 206], Val-Tyr-Val-Orn-Phe-Trp-NH2 [SEQ ID NO: 207], Ac-Arg-Phe-Trp [SEQ ID NO: 208], Val-Tyr-Val-Cit-Phe-Trp-NH2 [SEQ ID NO: 169], Val-Tyr-Val-Cit-Phe-Trp-NHMe [SEQ ID NO: 173], Val-Tyr-Val-Cit-Phe-Trp-NHEt [SEQ ID NO: 200], Val-Tyr-Val-Cit-Phe-Trp-NH(propyl) [SEQ ID NO: 231], Val-Tyr-Val-Cit-Phe-Trp-NH(isopropyl) [SEQ ID NO: 232], Val-Tyr-Val-Arg-Phe-D-Trp [SEQ ID NO: 210], Val-Tyr-Val-Cit-Phe-D-Trp-NH2 [SEQ ID NO: 211], Val-D-Tyr-Val-Cit-Phe-Trp-NH2 [SEQ ID NO: 212], Val-Tyr-Val-Cit-Phe-NH2 [SEQ ID NO: 213], Val-Tyr-Val-Cit-NH2 [SEQ ID NO: 214], Val-Tyr-Val-Cit-NH(isopropyl) [SEQ ID NO: 215], Val-D-Tyr-Val-Cit-NHEt [SEQ ID NO: 216]. In one embodiment, the synthetic peptide is selected from the group consisting of Val-Tyr-Val-Arg-Phe-Trp-NH2 [SEQ ID NO: 19], Val-Tyr-Val-Arg-Phe-Trp-NHMe [SEQ ID NO: 217], Val-Tyr-Val-Arg-Phe-Trp-NHEt [SEQ ID NO: 218], Val-Tyr-Val-Arg-Phe-D-Trp-NH2 [SEQ ID NO: 219], Val-D-Tyr-Val-Arg-Phe-Trp-NH2 [SEQ ID NO: 220], Val-Tyr-Val-Arg-Phe-NH2 [SEQ ID NO: 221], Val-Tyr-Val-Arg-NH2 [SEQ ID NO: 222], Val-Tyr-Val-Arg-NH(isopropyl) [SEQ ID NO: 223], Val-D-Tyr-Val-Arg-NHEt [SEQ ID NO:

224]. In one embodiment, the synthetic peptide is selected from the group consisting of Val-Phe-Val-Arg-Phe-Trp [SEQ ID NO: 233], Val-Phe-Val-Arg-Phe-Trp-NH2 [SEQ ID NO: 225], Val-Phe-Val-Cit-Phe-Trp-NH2 [SEQ ID NO: 226], Val-Phe-Val-Cit-Phe-Trp-NH2 [SEQ ID NO: 226], Val-Phe-Val-Cit-Phe-Trp-NHMe [SEQ ID NO: 227], Val-Phe-Val-Cit-Phe-Trp-NHEt [SEQ ID NO: 228], Val-Phe-Val-Arg-Phe-NH(cyclopentyl) [SEQ ID NO: 229], Val-Phe-Val-Cit-Phe-NH(cyclopentyl) [SEQ ID NO: 230].

In one embodiment, the present invention contemplates a method, comprising: a) administering a PCSK9 allosteric synthetic peptide to a subject, wherein said subject has at elevated PCSK9 protein levels in the blood; and b) reducing said at least one symptom of elevated PCSK9 by said PCSK9 allosteric peptide administration. In one embodiment, the at least one symptom comprises reduced low density lipoprotein receptor density. In one embodiment, said at least one symptom is reduced between 10%-85%. In one embodiment, said at least one symptom is reduced between 20%-65%. In one embodiment, said at least one symptom is reduced between 30%-55%. In one embodiment, the PCSK9 allosteric synthetic peptide comprises a PCSK9 allosteric inhibitor peptide that may contain one or more D-amino acids. In one embodiment, the administering comprises an effective dose of said PCSK9 allosteric peptide. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment, the allosteric synthetic peptide comprises between approximately 3-8 amino acids. In one embodiment, the allosteric synthetic peptide comprises between approximately 3-8 amino acids, wherein one or more of said 3-8 amino acids is a D-amino acid. In one embodiment, the allosteric synthetic peptide is six amino acids. In one embodiment, the allosteric synthetic peptide is six amino acids, wherein one or more of said six amino acids is a D-amino acid. In one embodiment, the allosteric synthetic peptide is three amino acids. In one embodiment, the allosteric synthetic peptide is three amino acids, wherein one or more of said three amino acids is a D-amino acid. In one embodiment the peptide is selected from the group consisting of Ibutyryl-Tyr-Val-Arg-Phe-Trp [SEQ ID NO: 197], Pivaloyl-Tyr-Val-Arg-Phe-Trp [SEQ ID NO: 198], Gly-Val-Tyr-Val-Cit-Phe-Trp [SEQ ID NO: 199], Val-Tyr-Val-Cit_-Phe-Trp-Gly [SEQ ID NO: 200], Val-Tyr-Val-Cit-Phe-Trp (NMe) [SEQ ID NO: 20], Val-Tyr-Val-Arg-D-Phe-Trp [SEQ ID NO: 202], Ac-D-Trp-D-Ala-D-Arg-NH2 [SEQ ID NO: 203], Boc-D-Trp-D-Phe-D-Arg-NH2 [SEQ ID NO: 204], MeOCO-D-Trp-D-Phe-D-Arg-NH2 [SEQ ID NO: 205], Succ-Tyr-Val-Cit-Phe-Trp [SEQ ID NO: 206], Val-Tyr-Val-Orn-Phe-Trp-NH2 [SEQ ID NO: 207], Ac-Arg-Phe-Trp [SEQ ID NO: 208], Val-Tyr-Val-Cit-Phe-Trp-NH2 [SEQ ID NO: 169], Val-Tyr-Val-Cit-Phe-Trp-NHMe [SEQ ID NO: 173], Val-Tyr-Val-Cit-Phe-Trp-NHEt [SEQ ID NO: 209], Val-Tyr-Val-Cit-Phe-Trp-NH(propyl) [SEQ ID NO: 23], Val-Tyr-Val-Cit-Phe-Trp-NH(isopropyl) [SEQ ID NO: 232], Val-Tyr-Val-Arg-Phe-D-Trp [SEQ ID NO: 210], Val-Tyr-Val-Cit-Phe-D-Trp-NH2 [SEQ ID NO: 211], Val-D-Tyr-Val-Cit-Phe-Trp-NH2 [SEQ ID NO: 212], Val-Tyr-Val-Cit-Phe-NH2 [SEQ ID NO: 213], Val-Tyr-Val-Cit-NH2 [SEQ ID NO: 214], Val-Tyr-Val-Cit-NH(isopropyl) [SEQ ID NO: 215], Val-D-Tyr-Val-Cit-NHEt [SEQ ID NO: 216]. In one embodiment, the synthetic peptide is selected from the group consisting of Val-Tyr-Val-Arg-Phe-Trp-NH2 [SEQ ID NO: 19], Val-Tyr-Val-Arg-Phe-Trp-NHMe [SEQ ID NO: 217], Val-Tyr-Val-Arg-Phe-Trp-NHEt [SEQ ID NO: 218], Val-Tyr-Val-Arg-Phe-D-Trp-NH2 [SEQ ID NO: 219], Val-D-Tyr-Val-Arg-Phe-Trp-NH2 [SEQ ID NO: 220], Val-Tyr-Val-Arg-Phe-NH2 [SEQ ID NO: 221], Val-Tyr-Val-Arg-NH2 [SEQ ID NO: 222], Val-Tyr-Val-Arg-NH(isopropyl) [SEQ ID NO: 223], Val-D-Tyr-Val-Arg-NHEt [SEQ ID NO: 224]. In one embodiment, the synthetic peptide is selected from the group consisting of Val-Phe-Val-Arg-Phe-Trp [SEQ ID NO: 233], Val-Phe-Val-Arg-Phe-Trp-NH2 [SEQ ID NO: 225], Val-Phe-Val-Cit-Phe-Trp-NH2 [SEQ ID NO: 226], Val-Phe-Val-Cit-Phe-Trp-NH2 [SEQ ID NO: 226], Val-Phe-Val-Cit-Phe-Trp-NHMe [SEQ ID NO: 227], Val-Phe-Val-Cit-Phe-Trp-NHEt [SEQ ID NO: 228], Val-Phe-Val-Arg-Phe-NH(cyclopentyl) [SEQ ID NO: 229], Val-Phe-Val-Cit-Phe-NH(cyclopentyl) [SEQ ID NO: 230].

In one embodiment, the present invention contemplates a method, comprising: a) administering a PCSK9 allosteric synthetic peptide to a subject, wherein said subject has reduced PCSK9 protein levels in the blood; and b) reducing said at least one symptom of deficient levels of circulating PCSK9 by said PCSK9 allosteric peptide administration. In one embodiment, the at least one symptom comprises excessive low density lipoprotein receptor density. In one embodiment, at least one symptom comprises circulating LDL-cholesterol levels below 75 mg/dL. In one embodiment, said at least one symptom comprises circulating LDL-cholesterol levels below 50 mg/dL. In one embodiment, the PCSK9 allosteric synthetic peptide comprises a PCSK9 allosteric enhancer peptide that may contain one or more D-amino acids. In one embodiment, the administering comprises an effective dose of said PCSK9 allosteric peptide. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment, the allosteric synthetic peptide comprises between approximately 3-8 amino acids. In one embodiment, the allosteric synthetic peptide comprises between approximately 3-8 amino acids, wherein one or more of said 3-8 amino acids is a D-amino acid. In one embodiment, the allosteric synthetic peptide is six amino acids. In one embodiment, the allosteric synthetic peptide is six amino acids, wherein one or more of said six amino acids is a D-amino acid. In one embodiment, the allosteric synthetic peptide is three amino acids. In one embodiment, the allosteric synthetic peptide is three amino acids, wherein one or more of said three amino acids is a D-amino acid.

In one embodiment, the present invention contemplates a method comprising: a) providing; i) a PCSK9 protein, wherein said protein comprises an allosteric modulation site and an orthosteric low density lipoprotein receptor (LDLR) binding site; and ii) an allosteric synthetic peptide capable of binding said allosteric modulation site; b) binding said allosteric synthetic peptide to said allosteric modulation site, wherein said allosteric synthetic peptide induces a conformational shift of said orthosteric LDLR binding site. In one embodiment, said binding of said allosteric synthetic peptide to said allosteric modulation site, inhibits an induced fit conformational shift of said orthosteric LDLR binding site. In one embodiment, the binding induces a conformational shift of said PCSK9 protein. In one embodiment, the resulting PCSK9 conformational shift reduces the binding affinity of said orthosteric LDLR binding site interaction to a LDLR, wherein low density lipoprotein clearance is increased. In one embodiment, the conformational shift enhances dissociation of said orthosteric low density lipoprotein receptor binding site from a low density lipoprotein receptor. In one embodiment, the conformational shift reduces the orthosteric Cis-His Rich Domain (CHRD) binding site to a binding ligand (e.g., for example, to facilitate vesicle trafficking at low pH; DeVay et al., "Characterization of proprotein convertase subtilisin/kexin type 9 (PCSK9) trafficking reveals a novel lysosomal targeting mechanism via amyloid precursor-like protein 2 (APLP2)" *J Biol Chem.* 288(15):10805-10818 (2013). In one embodiment, the orthosteric low density lipoprotein receptor binding site conformational shift comprises an induced fit inhibition. In one embodiment, the binding of said allosteric synthetic peptide reduces the conformational shift required for the induced fit of the orthosteric LDLR binding site of PCSK9, inhibiting the binding affinity of said orthosteric LDLR interaction, wherein low density lipoprotein clearance is increased. In one embodiment, the inducing of said orthosteric low density lipoprotein receptor binding site conformational shift is biomechanical. In one embodiment, the conformational shift results in biomechanical stiffening of the connecting loop between a PCSK9 catalytic domain and a PCSK9 C-terminal domain. In one embodiment, the biomechanical conformational shift comprises a translocational and/or rotational movement of amino acid alanine$^{443}$ side chain and/or backbone. In one embodiment, the biomechanical conformational shift comprises a translocational and/or rotational movement of amino acid valine$^{441}$ side chain and/or backbone. In one embodiment, the biomechanical conformational shift comprises a translocational and/or rotational movement of amino acid aspartic acid$^{422}$ side chain and/or backbone. In one embodiment, the biomechanical conformational shift comprises a translocational and/or rotational movement of amino acid threonine$^{162}$ side chain and/or backbone. In one embodiment, the biomechanical conformational shift comprises a translocational and/or rotational movement of amino acid proline$^{445}$ side chain and/or backbone. In one embodiment, the biomechanical conformational shift comprises a translocational and/or rotational movement of amino acid proline$^{446}$ side chain and/or backbone. In one embodiment, the biomechanical conformational shift comprises a reorientation and translocation of histidine$^{449}$. In one embodiment, the biomechanical mechanism comprises the inhibition of the translocational and/or rotational movement of amino acid alanine$^{443}$ side chain and/or backbone. In one embodiment, the biomechanical mechanism comprises the inhibition of the translocational and/or rotational movement of amino acid valine$^{441}$ side chain and/or backbone. In one embodiment, the biomechanical mechanism comprises the inhibition of the translocational and/or rotational movement of amino acid aspartic acid$^{422}$ side chain and/or backbone. In one embodiment, the biomechanical mechanism comprises the inhibition of the translocational and/or rotational movement of amino acid threonine$^{162}$ side chain and/or backbone. In one embodiment, the biomechanical mechanism comprises the inhibition of the translocational and/or rotational movement of amino acid proline$^{445}$ side chain and/or backbone. In one embodiment, the biomechanical mechanism comprises the inhibition of the translocational and/or rotational movement of amino acid proline$^{446}$ side chain and/or backbone. In one embodiment, the biomechanical shift comprises the inhibition of the translocational and/or rotational movement of histidine$^{449}$ side chain and/or backbone. In one embodiment, the allosteric synthetic peptide is VYVRFW [SEQ ID NO: 2]. In one embodiment, the allosteric synthetic peptide is VLELYW [SEQ ID NO: 3]. In one embodiment, the allosteric synthetic peptide is ISDLSY [SEQ ID NO: 4]. In one embodiment, the allosteric synthetic peptide comprises between approximately 3-8 amino acids. In one embodiment, the allosteric synthetic peptide is six amino acids. In one embodiment, the allosteric synthetic peptide is less than 1,300 Da. In one embodiment, the allosteric synthetic peptide ranges between approximately 466-1067 Da. In one embodiment, the allosteric synthetic peptide ranges between approximately 175-1,000 Da. In one embodiment the peptide comprises between 3-8 amino acids and contains one or more D-amino acids. In one embodiment, the allosteric inhibitor peptide is six amino acids, wherein one or more of said six amino acids is a D-amino acid. In one embodiment the peptide is selected from the group consisting of Ibutyryl-Tyr-Val-Arg-Phe-Trp [SEQ ID NO: 197], Pivaloyl-Tyr-Val-Arg-Phe-Trp [SEQ ID NO: 198], Gly-Val-Tyr-Val-Cit-Phe-Trp [SEQ ID NO: 199], Val-Tyr-Val-Cit_-Phe-Trp-Gly [SEQ ID NO: 200], Val-Tyr-Val-Cit-Phe-Trp(NMe) [SEQ ID NO: 201], Val-Tyr-Val-Arg-D-Phe-Trp [SEQ ID NO: 202], Ac-D-Trp-D-Ala-D-Arg-NH2 [SEQ ID NO: 203], Boc-D-Trp-D-Phe-D-Arg-NH2 [SEQ ID NO: 204], MeOCO-D-Trp-D-Phe-D-Arg-NH2 [SEQ ID NO: 205], Succ-Tyr-Val-Cit-Phe-Trp [SEQ ID NO: 206], Val-Tyr-Val-Orn-Phe-Trp-NH2 [SEQ ID NO: 207], Ac-Arg-Phe-Trp [SEQ ID NO: 208], Val-Tyr-Val-Cit-Phe-Trp-NH2 [SEQ ID NO: 169], Val-Tyr-Val-Cit-Phe-Trp-NHMe [SEQ ID NO: 173], Val-Tyr-Val-Cit-Phe-Trp-NHEt [SEQ ID NO: 209], Val-Tyr-Val-Cit-Phe-Trp-NH(propyl) [SEQ ID NO: 231], Val-Tyr-Val-Cit-Phe-Trp-NH(isopropyl) [SEQ ID NO: 232], Val-Tyr-Val-Arg-Phe-D-Trp [SEQ ID NO: 210], Val-Tyr-Val-Cit-Phe-D-Trp-NH2 [SEQ ID NO: 211], Val-D-Tyr-Val-Cit-Phe-Trp-NH2 [SEQ ID NO: 212], Val-Tyr-Val-Cit-Phe-NH2 [SEQ ID NO: 213], Val-Tyr-Val-Cit-NH2 [SEQ ID NO: 214], Val-Tyr-Val-Cit-NH(isopropyl) [SEQ ID NO: 215], Val-D-Tyr-Val-Cit-NHEt [SEQ ID NO: 216]. In one embodiment, the synthetic peptide is selected from the group consisting of Val-Tyr-Val-Arg-Phe-Trp-NH2 [SEQ ID NO: 19], Val-Tyr-Val-Arg-Phe-Trp-NHMe [SEQ ID NO: 217], Val-Tyr-Val-Arg-Phe-Trp-NHEt [SEQ ID NO: 218], Val-Tyr-Val-Arg-Phe-D-Trp-NH2 [SEQ ID NO: 219], Val-D-Tyr-Val-Arg-Phe-Trp-NH2 [SEQ ID NO: 220], Val-Tyr-Val-Arg-Phe-NH2 [SEQ ID NO: 221], Val-Tyr-Val-Arg-NH2 [SEQ ID NO: 222], Val-Tyr-Val-Arg-NH(isopropyl) [SEQ ID NO: 223], Val-D-Tyr-Val-Arg-NHEt [SEQ ID NO: 224].

In one embodiment, the present invention contemplates a compound of the formula: Val-Tyr-Val-Arg-Phe-Trp [SEQ ID NO: 2].

In one embodiment, the present invention contemplates a compound of the formula: β-Ala-Phe(3-CH2NH2)-Val-D-Ser(p)-Phe-Trp [SEQ ID NO: 5].

In one embodiment, the present invention contemplates a compound of the formula: Thr-Leu-Cys(CH2-Ph)-Thr-Trp-Ser-Ser-Ser(p) [SEQ ID NO: 6].

In one embodiment, the present invention contemplates a compound of the formula: Thr-Leu-Asp(NHCH2Ph)-Thr-Trp-Ser-Ser-Ser(p) [SEQ ID NO: 7].

In one embodiment, the present invention contemplates a compound of the formula: Thr-Leu-Gly(CH2CH2cyclohexyl)-Thr-Trp-Ser-Ser-Ser(p) [SEQ ID NO: 8].

In one embodiment, the present invention contemplates a compound of the formula: Thr-Leu-Hph-Thr-Trp-Ser-Ser-Ser(p) [SEQ ID NO: 9].

In one embodiment, the present invention contemplates a compound of the formula: Thr-Leu-Cys(CH2-Ph)-Thr-Trp(3-Me)-Ser-Ser-Ser(p) [SEQ ID NO: 10].

In one embodiment, the present invention contemplates a compound of the formula: Val-Leu-Glu-Leu-Tyr-Trp [SEQ ID NO: 3].

In one embodiment, the present invention contemplates a compound of the formula: Leu-Asp-Leu-Phe-Phe-Ser [SEQ ID NO: 11].

In one embodiment, the present invention contemplates a compound of the formula: Ile-Leu-Asp-Leu-Ser-Tyr [SEQ ID NO: 12].

In one embodiment, the present invention contemplates a compound of the formula: Ac-Trp-Ser-Ser(p) [SEQ ID NO: 13].

In one embodiment, the present invention contemplates a compound of the formula: Ac-Trp-Ala-Ser(p) [SEQ ID NO: 14].

In one embodiment, the present invention contemplates a compound of the formula: Ac-Trp(5-F)-Ala-Ser(p)-morpholine [SEQ ID NO: 15].

In one embodiment, the present invention contemplates a compound of the formula: Thr-Leu-Thr-Trp-Ser-Ser-Ser(p) [SEQ ID NO: 16].

In one embodiment, the present invention contemplates a compound of the formula: Ac-Tyr-Trp-Gly [$SEQ ID NO: 17].

In one embodiment, the present invention contemplates a compound of the formula: Phe(4-Ph)-Ala-Ser(p)-morpholine [SEQ ID NO: 18].

In one embodiment, the present invention contemplates a compound including, but not limited to, Val-Tyr-Val-Arg-Phe-Trp-NH2 [SEQ ID NO: 19], Ala-Phe(3-CH2NH2)-Val-D-Ser(p)-Phe-Trp-NH2 [SEQ ID NO: 20], Thr-Leu-Cys(CH2-Ph)-Thr-Trp-Ser-Ser-Ser(p)-NH2 [SEQ ID NO: 21], Thr-Leu-Asp(NHCH2Ph)-Thr-Trp-Ser-Ser-Ser(p)-NH2 [SEQ ID NO: 22], Thr-Leu-Gly(CH2CH2cyclohexyl)-Thr-Trp-Ser-Ser-Ser(p)-NH2 [SEQ ID NO: 23], Thr-Leu-Hph-Thr-Trp-Ser-Ser-Ser(p)-NH2 [SEQ ID NO: 24], Thr-Leu-Cys(CH2-Ph)-Thr-Trp(3-Me)-Ser-Ser-Ser(p)-NH2 [SEQ ID NO: 25], Val-Leu-Glu-Leu-Tyr-Trp-NH2 [SEQ ID NO: 26], Leu-Asp-Leu-Phe-Phe-Ser-NH2 [SEQ ID NO: 27], Ile-Leu-Asp-Leu-Ser-Tyr-NH2 [SEQ ID NO: 28], Ac-Trp-Ser-Ser(p)-NH2 [SEQ ID NO: 29], Ac-Trp-Ala-Ser(p)-NH2 [SEQ ID NO: 3], Ac-Trp(5-F)-Ala-Ser(p)-NH2 [SEQ ID NO: 31] and Thr-Leu-Thr-Trp-Ser-Ser-Ser(p)-NH2 [SEQ ID NO: 32].

In one embodiment, the present invention contemplates a compound including, but not limited to, Ac-Trp-Ser-Ser(p)-NHCH3 [SEQ ID NO: 33], Ac-Trp-Ala-Ser(p)-NHCH3 [SEQ ID NO: 34], Ac-Trp-Ala-Ser(p)-morpholine [SEQ ID NO: 35], Ac-Trp-Ala-Ser(p)-4-methylpiperizine [SEQ ID NO: 36], Ac-Trp-Ala-Ser(p)-piperidine [SEQ ID NO: 37], Ac-Trp-Ala-Ser(p)-pyrrolidine [SEQ ID NO: 38].

In one embodiment, the present invention contemplates a compound including, but not limited to, Ac-Thr-Leu-Cys(CH2-Ph)-Thr-Trp-Ser-Ser-Ser(p) [SEQ ID NO: 39], Ac-Thr-Leu-Asp(NHCH2Ph)-Thr-Trp-Ser-Ser-Ser(p) [SEQ ID NO: 40], Ac-Thr-Leu-Gly(CH2CH2cyc Thr-Leu-Hph-Thr-Trp-Ser-Ser-Ser(p)-NH2lohexyl)-Thr-Trp-Ser-Ser-Ser(p) [SEQ ID NO: 41], Ac-Thr-Leu-Hph-Thr-Trp-Ser-Ser-Ser(p) [SEQ ID NO: 42], Ac-Thr-Leu-Cys(CH2-Ph)-Thr-Trp(3-Me)-Ser-Ser-Ser(p) [SEQ ID NO: 43], Ac-Val-Leu-Glu-Leu-Tyr-Trp [SEQ ID NO: 44], Ac-Leu-Asp-Leu-Phe-Phe-Ser [SEQ ID NO: 45], Ac-Ile-Leu-Asp-Leu-Ser-Tyr [SEQ ID NO: 46], and Ac-Thr-Leu-Thr-Trp-Ser-Ser-Ser(p) [SEQ ID NO: 47].

In one embodiment, the present invention contemplates a compound including, but not limited to, Thr-Leu-Cys(CH2-Ph)-Thr-Trp-Ser-Ala-Ser(p) [SEQ ID NO: 48], Thr-Leu-Asp(NHCH2Ph)-Thr-Trp-Ser-Ala-Ser(p) [SEQ ID NO: 49], Thr-Leu-Gly(CH2CH2cyclohexyl)-Thr-Trp-Ser-Ala-Ser(p) [SEQ ID NO: 50], Thr-Leu-Hph-Thr-Trp-Ser-Ala-Ser(p), [SEQ ID NO: 51], Thr-Leu-Cys(CH2-Ph)-Thr-Trp(3-Me)-Ser-Ala-Ser(p) [SEQ ID NO: 52] and Thr-Leu-Thr-Trp-Ser-Ala-Ser(p) [SEQ ID NO: 53].

In one embodiment, the present invention contemplates a compound including, but not limited to, Thr-Leu-Cys(CH2-Ph)-Thr-Trp-Ser-Ala-Ser(p)-NH2 [SEQ ID NO: 54], Thr-Leu-Asp(NHCH2Ph)-Thr-Trp-Ser-Ala-Ser(p)-NH2 [SEQ ID NO: 55], Thr-Leu-Gly(CH2CH2cyclohexyl)-Thr-Trp-Ser-Ala-Ser(p)-NH2 [SEQ ID NO: 56], Thr-Leu-Hph-Thr-Trp-Ser-Ala-Ser(p)-NH2 [SEQ ID NO: 57], Thr-Leu-Cys(CH2-Ph)-Thr-Trp(3-Me)-Ser-Ala-Ser(p)-NH2 [SEQ ID NO: 58] and Thr-Leu-Thr-Trp-Ser-Ala-Ser(p)-NH2 [SEQ ID NO: 59].

In one embodiment, the present invention contemplates a compound including, but not limited to, Ac-Thr-Leu-Cys(CH2-Ph)-Thr-Trp-Ser-Ala-Ser(p) [SEQ ID NO: 60], Ac-Thr-Leu-Asp(NHCH2Ph)-Thr-Trp-Ser-Ala-Ser(p) [SEQ ID NO: 61], Ac-Thr-Leu-Gly(CH2CH2cyclohexyl)-Thr-Trp-Ser-Ala-Ser(p) [SEQ ID NO: 62], Ac-Thr-Leu-Hph-Thr-Trp-Ser-Ala-Ser(p) [SEQ ID NO: 63], Ac-Thr-Leu-Cys(CH2-Ph)-Thr-Trp(3-Me)-Ser-Ala-Ser(p) [SEQ ID NO: 64] and Ac-Thr-Leu-Thr-Trp-Ser-Ala-Ser(p) [SEQ ID NO: 65].

In one embodiment, the present invention contemplates a compound including, but not limited to, Ac-Thr-Leu-Cys(CH2-Ph)-Thr-Trp-Ser-Ala-Ser(p)-NH2 [SEQ ID NO: 66], Ac-Thr-Leu-Asp(NHCH2Ph)-Thr-Trp-Ser-Ala-Ser(p)-NH2 [SEQ ID NO: 67], Ac-Thr-Leu-Gly(CH2CH2cyclohexyl)-Thr-Trp-Ser-Ala-Ser(p)-NH2 [SEQ ID NO: 68], Ac-Thr-Leu-Hph-Thr-Trp-Ser-Ala-Ser(p)-NH2 [SEQ ID NO: 69], Ac-Thr-Leu-Cys(CH2-Ph)-Thr-Trp(3-Me)-Ser-Ala-Ser(p)-NH2 [SEQ ID NO: 70], Ac-Thr-Leu-Thr-Trp-Ser-Ala-Ser(p)-NH2 [SEQ ID NO: 71].

In one embodiment, the present invention contemplates a compound including, but not limited to, Thr-Leu-Cys(CH2-Ph)-Thr-Trp-Ser-Ser(p) [SEQ ID NO: 72], Thr-Leu-Asp(NHCH2Ph)-Thr-Trp-Ser-Ser(p) [SEQ ID NO: 73], Thr-Leu-Gly(CH2CH2cyclohexyl)-Thr-Trp-Ser-Ser(p) [SEQ ID NO: 74], Thr-Leu-Hph-Thr-Trp-Ser-Ser(p) [SEQ ID NO: 75], Thr-Leu-Cys(CH2-Ph)-Thr-Trp(3-Me)-Ser-Ser(p) [SEQ ID NO: 76] and Thr-Leu-Thr-Trp-Ser-Ser(p) [SEQ ID NO: 77].

In one embodiment, the present invention contemplates a compound including, but not limited to, Ac-Thr-Leu-Cys(CH2-Ph)-Thr-Trp-Ser-Ser(p)-NH2 [SEQ ID NO: 78], Ac-Thr-Leu-Asp(NHCH2Ph)-Thr-Trp-Ser-Ser(p)-NH2 [SEQ ID NO: 79], Ac-Thr-Leu-Gly(CH2CH2cyclohexyl)-Thr-Trp-Ser-Ser(p)-NH2 [SEQ ID NO: 80], Ac-Thr-Leu-Hph-Thr-Trp-Ser-Ser(p)-NH2 [SEQ ID NO: 81], Ac-Thr- Leu-Cys(CH2-Ph)-Thr-Trp(3-Me)-Ser-Ser(p)-NH2 [SEQ ID NO: 82] and Ac-Thr-Leu-Thr-Trp-Ser-Ser(p)-NH2 [SEQ ID NO: 83].

In one embodiment, the present invention contemplates a compound including, but not limited to, Thr-Leu-Cys(CH2-Ph)-Thr-Trp-Ala-Ser(p) [SEQ ID NO: 84]. Thr-Leu-Asp(NHCH2Ph)-Thr-Trp-Ala-Ser(p) [SEQ ID NO: 85], Thr-Leu-Gly(CH2CH2cyclohexyl)-Thr-Trp-Ala-Ser(p) [SEQ ID NO: 86], Thr-Leu-Hph-Thr-Trp-Ala-Ser(p) [SEQ ID NO: 87], Thr-Leu-Cys(CH2-Ph)-Thr-Trp(3-Me)-Ala-Ser(p) [SEQ ID NO: 88] and Thr-Leu-Thr-Trp-Ala-Ser(p) [SEQ ID NO: 89].

In one embodiment, the present invention contemplates a compound including, but not limited to, Ac-Thr-Leu-Cys(CH2-Ph)-Thr-Trp-Ala-Ser(p)-NH2 [SEQ ID NO: 90], Ac-Thr-Leu-Asp(NHCH2Ph)-Thr-Trp-Ala-Ser(p)-NH2 [SEQ ID NO: 91], Ac-Thr-Leu-Gly(CH2CH2cyclohexyl)-Thr-Trp-Ala-Ser(p)-NH2 [SEQ ID NO: 92], Ac-Thr-Leu-Hph-Thr-Trp-Ala-Ser(p)-NH2 [SEQ ID NO: 93], Ac-Thr-Leu-Cys(CH2-Ph)-Thr-Trp(3-Me)-Ala-Ser(p)-NH2 [SEQ ID NO: 94] and Ac-Thr-Leu-Thr-Trp-Ala-Ser(p)-NH2 [SEQ ID NO: 95].

In one embodiment, the present invention contemplates a compound including, but not limited to, Thr-Leu-Cys(CH2-Ph)-Ala-Trp-Ser-Ser-Ser(p) [SEQ ID NO: 96], Thr-Leu-Asp(NHCH2Ph)-Ala-Trp-Ser-Ser-Ser(p) [SEQ ID NO: 97], Thr-Leu-Gly(CH2CH2cyclohexyl)-Ala-Trp-Ser-Ser-Ser(p) [SEQ ID NO: 98], Thr-Leu-Hph-Ala-Trp-Ser-Ser-Ser(p) [SEQ ID NO: 99], Ac-Thr-Leu-Cys(CH2-Ph)-Ala-Trp-Ser-Ser-Ser(p) [SEQ ID NO: 100], Ac-Thr-Leu-Asp(NHCH2Ph)-Ala-Trp-Ser-Ser-Ser(p) [SEQ ID NO: 101], Ac-Thr-Leu-Gly(CH2CH2cyclohexyl)-Ala-Trp-Ser-Ser-Ser(p) [SEQ ID NO: 102], Ac-Thr-Leu-Hph-Ala-Trp-Ser-Ser-Ser(p) [SEQ ID NO: 103], Ac-Thr-Leu-Cys(CH2-Ph)-Ala-Trp-Ser-Ser-Ser(p)-NH2 [SEQ ID NO: 104], Ac-Thr-Leu-Asp(NHCH2Ph)-Ala-Trp-Ser-Ser-Ser(p)-NH2 [SEQ ID NO: 105], Ac-Thr-Leu-Gly(CH2CH2cyclohexyl)-Ala-Trp-Ser-Ser-Ser(p)-NH2 [SEQ ID NO: 106] and Ac-Thr-Leu-Hph-Ala-Trp-Ser-Ser-Ser(p)-NH2 [SEQ ID NO: 107].

In one embodiment, the present invention contemplates a compound including, but not limited to, Thr-Leu-Cys(CH2-Ph)-Ser-Trp-Ser-Ser-Ser(p) [SEQ ID NO: 108], Thr-Leu-Asp(NHCH2Ph)-Ser-Trp-Ser-Ser-Ser(p) [SEQ ID NO: 109], Thr-Leu-Gly(CH2CH2cyclohexyl)-Ser-Trp-Ser-Ser-Ser(p) [SEQ ID NO: 110], Thr-Leu-Hph-Ser-Trp-Ser-Ser-Ser(p) [SEQ ID NO: 111], Ac-Thr-Leu-Cys(CH2-Ph)-Ser-Trp-Ser-Ser-Ser(p) [SEQ ID NO: 112], Ac-Thr-Leu-Asp(NHCH2Ph)-Ser-Trp-Ser-Ser-Ser(p) [SEQ ID NO: 113], Ac-Thr-Leu-Gly(CH2CH2cyclohexyl)-Ser-Trp-Ser-Ser-Ser(p) [SEQ ID NO: 114], Ac-Thr-Leu-Hph-Ser-Trp-Ser-Ser-Ser(p) [SEQ ID NO: 115] Ac-Thr-Leu-Cys(CH2-Ph)-Ser-Trp-Ser-Ser-Ser(p)-NH2 [SEQ ID NO: 116], Ac-Thr-Leu-Asp(NHCH2Ph)-Ser-Trp-Ser-Ser-Ser(p)-NH2 [SEQ ID NO: 117], Ac-Thr-Leu-Gly(CH2CH2cyclohexyl)-Ser-Trp-Ser-Ser-Ser(p)-NH2 [SEQ ID NO: 118] and Ac-Thr-Leu-Hph-Ser-Trp-Ser-Ser-Ser(p)-NH2 [SEQ ID NO: 119].

In one embodiment, the present invention contemplates a compound including, but not limited to, Ac-Cys(CH2-Ph)-Thr-Trp-Ser-Ser-Ser(p) [SEQ ID NO: 120], Ac-Asp(NHCH2Ph)-Thr-Trp-Ser-Ser-Ser(p) [SEQ ID NO: 121], Ac-Gly(CH2CH2cyclohexyl)-Thr-Trp-Ser-Ser-Ser(p) [SEQ ID NO: 122], Ac-Hph-Thr-Trp-Ser-Ser-Ser(p) [SEQ ID NO: 123], Ac-Cys(CH2-Ph)-Thr-Trp-Ser-Ser-Ser(p)-NH2 [SEQ ID NO: 124], Ac-Asp(NHCH2Ph)-Thr-Trp-Ser-Ser-Ser(p)-NH2 [SEQ ID NO: 125], Ac-Gly(CH2CH2cyclohexyl)-Thr-Trp-Ser-Ser-Ser(p)-NH2 [SEQ ID NO: 126] and Ac-Hph-Thr-Trp-Ser-Ser-Ser(p)-NH2 [SEQ ID NO: 127].

In one embodiment, the present invention contemplates a compound including, but not limited to, BOC-Cys(CH2-Ph)-Thr-Trp-Ser-Ser-Ser(p) [SEQ ID NO: 128], BOC-Asp(NHCH2Ph)-Thr-Trp-Ser-Ser-Ser(p) [SEQ ID NO: 129], BOC-Gly(CH2CH2cyclohexyl)-Thr-Trp-Ser-Ser-Ser(p) [SEQ ID NO: 130], BOC-Hph-Thr-Trp-Ser-Ser-Ser(p) [SEQ ID NO: 131], BOC-Cys(CH2-Ph)-Thr-Trp-Ser-Ser-Ser(p)-NH2 [SEQ ID NO: 132], BOC-Asp(NHCH2Ph)-Thr-Trp-Ser-Ser-Ser(p)-NH2 [SEQ ID NO: 133], BOC-Gly(CH2CH2cyclohexyl)-Thr-Trp-Ser-Ser-Ser(p)-NH2 [SEQ ID NO: 134] and BOC-Hph-Thr-Trp-Ser-Ser-Ser(p)-NH2 [SEQ ID NO: 135].

In one embodiment, the present invention contemplates a compound including, but not limited to, Thr-Leu-Cys(CH3)-Thr-Trp-Ser-Ser-Ser(p) [SEQ ID NO: 136], Thr-Leu-Cys(CH(CH3)2)-Thr-Trp-Ser-Ser-Ser(p) [SEQ ID NO: 137], Thr-Leu-Cys(CH2-3,4-difluorophenyl)-Thr-Trp-Ser-Ser-Ser(p) [SEQ ID NO: 138], Thr-Leu-Cys(CH2-3-hydroxyphenyl)-Thr-Trp-Ser-Ser-Ser(p) [SEQ ID NO: 139], Thr-Leu-Cys(CH2-3-methyphenyl)-Thr-Trp-Ser-Ser-Ser(p) [SEQ ID NO: 140] and Ac-Leu-Cys(CH2-Ph)-Thr-Trp-Ser-Ser-Ser(p)-NH2 [SEQ ID NO: 141].

In one embodiment, the present invention contemplates a compound selected from the group consisting of Ac-Tyr-Trp(6-OMe)-Gly [SEQ ID NO: 143], Ac-Tyr(3-F)-Trp-Gly [SEQ ID NO: 144], pivaloyl-Tyr-Trp-Gly [SEQ ID NO: 145], mesyl-Tyr-Trp-Gly [SEQ ID NO: 146], BOC-Tyr-Trp-Gly [SEQ ID NO: 147].

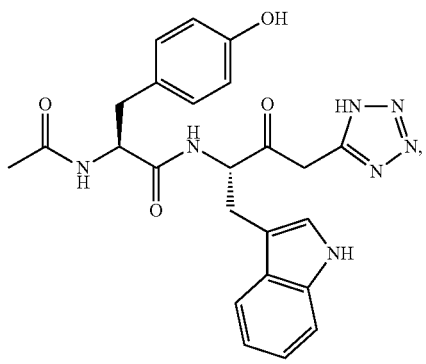

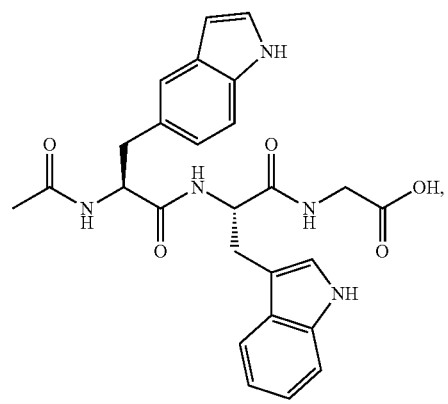

-continued

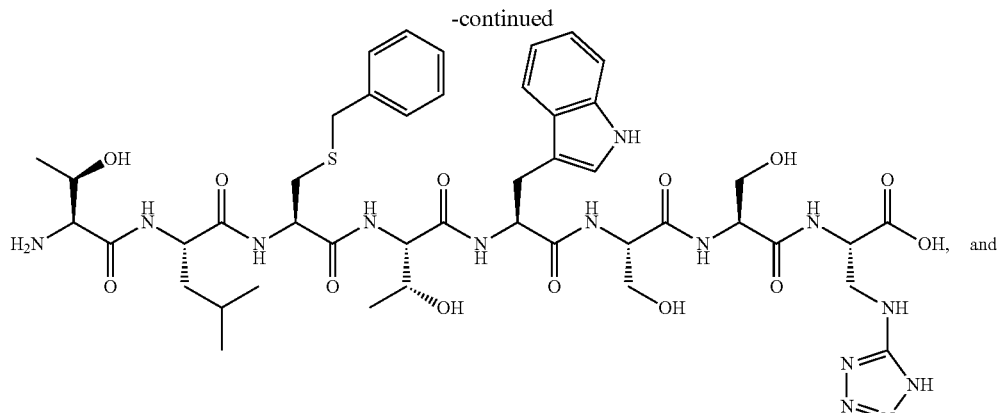

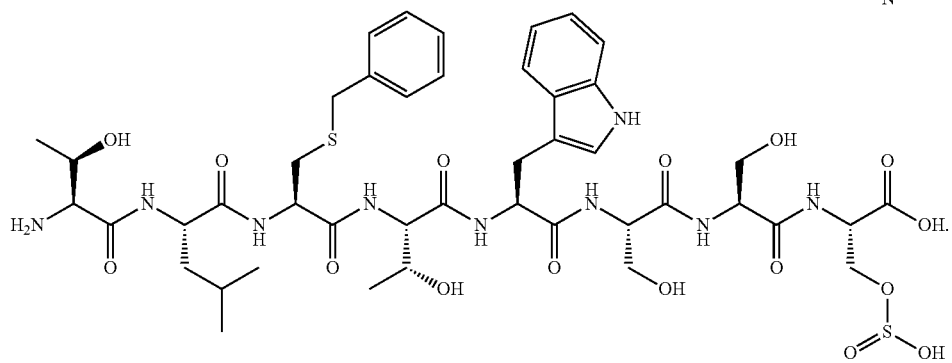

In one embodiment, the present invention contemplates a compound of the formula: Ac-D-Trp-D-Phe(3CF3)-D-Arg-NH2 [SEQ ID NO: 148].

In one embodiment, the present invention contemplates a compound of the formula: Ac-D-Trp-D-Phe(3Cl)-D-Arg-NH2 [SEQ ID NO: 149].

In one embodiment, the present invention contemplates a compound of the formula: Ac-D-Trp-D-Phe-D-Arg-NH2 [SEQ ID NO: 150].

In one embodiment, the present invention contemplates a compound of the formula: Ac-D-Trp-D-Phe-D-Arg [SEQ ID NO: 151].

In one embodiment, the present invention contemplates a compound of the formula: NAc-NMe-D-Arg-D-Phe(3OH)-D-Trp-NH2 [SEQ ID NO: 152].

In one embodiment, the present invention contemplates a compound of the formula: Ac-Arg-Phe(3CF3)-Gly [SEQ ID NO: 153].

In one embodiment, the present invention contemplates a compound of the formula: Ac-Ala-Val-Arg-N(Me)(Ph3CF3) [SEQ ID NO: 154].

In one embodiment, the present invention contemplates a compound of the formula: Ac-D-Arg-D-Phe(3OH)-D-Trp [SEQ ID NO: 155].

In one embodiment, the present invention contemplates a compound of the formula: Ac-D-Arg-D-Phe(3OH)-D-Trp-NH2 [SEQ ID NO: 156].

In one embodiment, the present invention contemplates a compound of the formula: Propionyl-D-Arg-D-Phe(3OH)-D-Trp [SEQ ID NO: 157].

In one embodiment, the present invention contemplates a compound of the formula: Ac-Val-Arg-Phe-Trp [SEQ ID NO: 158].

In one embodiment, the present invention contemplates a compound of the formula: Ac-Tyr-Val-Arg-Phe-Trp [SEQ ID NO: 159].

In one embodiment, the present invention contemplates a compound of the formula: Val-Tyr-Asp-Arg-Phe-Trp [SEQ ID NO: 160].

In one embodiment, the present invention contemplates a compound of the formula: Val-Tyr-Glu-Arg-Phe-Trp [SEQ ID NO: 161].

In one embodiment, the present invention contemplates a compound of the formula: Val-Tyr-Val-Cit-Phe-Trp [SEQ ID NO: 162].

In one embodiment, the present invention contemplates a compound of the formula: D-Val-D-Tyr-D-Val-D-Arg-D-Phe-D-Trp [SEQ ID NO: 163].

In one embodiment, the present invention contemplates a compound of the formula: D-Trp-D-Phe-D-Arg-D-Val-D-Tyr-D-Val [SEQ ID NO: 164].

In one embodiment, the present invention contemplates a compound of the formula: D-Arg-D-Phe-D-Trp [SEQ ID NO: 165].

In one embodiment, the present invention contemplates a compound of the formula: Ac-D-Arg-D-Phe-D-Trp [SEQ ID NO: 166].

In one embodiment, the present invention contemplates a compound of the formula: Ac-D-Arg-D-Phe-D-Trp-NH2 [SEQ ID NO: 167].

In one embodiment, the present invention contemplates a compound of the formula: D-Trp-D-Phe-D-Arg [SEQ ID NO: 168].

In one embodiment, the present invention contemplates a compound of the formula: Val-Tyr-Val-Cit-Phe-Trp-NH2 [SEQ ID NO: 169], Val-Tyr-Val-Cit-Phe-Trp-NHMe [SEQ ID NO: 173], Val-Tyr-Val-Cit-Phe-Trp-NHEt [SEQ ID NO: 209], Val-Tyr-Val-Cit-Phe-Trp-NH(propyl) [SEQ ID NO: 231], Val-Tyr-Val-Cit-Phe-Trp-NH(isopropyl) [SEQ ID NO: 232], Val-Tyr-Val-Arg-Phe-D-Trp [SEQ ID NO: 210], Val-Tyr-Val-Cit-Phe-D-Trp-NH2 [SEQ ID NO: 211], Val-D-Tyr- Val-Cit-Phe-Trp-NH2 [SEQ ID NO: 212], Val-Tyr-Val-Cit-Phe-NH2 [SEQ ID NO: 213], Val-Tyr-Val-Cit-NH2 [SEQ ID NO: 214], Val-Tyr-Val-Cit-NH(isopropyl) [SEQ ID NO: 215], Val-D-Tyr-Val-Cit-NHEt [SEQ ID NO: 216].

In one embodiment, the synthetic peptide is selected from the group consisting of Val-Tyr-Val-Arg-Phe-Trp-NH2 [SEQ ID NO: 19], Val-Tyr-Val-Arg-Phe-Trp-NHMe [SEQ ID NO: 217], Val-Tyr-Val-Arg-Phe-Trp-NHEt [SEQ ID NO: 218], Val-Tyr-Val-Arg-Phe-D-Trp-NH2 [SEQ ID NO: 219], Val-D-Tyr-Val-Arg-Phe-Trp-NH2 [SEQ ID NO: 220], Val-Tyr-Val-Arg-Phe-NH2 [SEQ ID NO: 221], Val-Tyr-Val-Arg-NH2 [SEQ ID NO: 222], Val-Tyr-Val-Arg-NH(isopropyl) [SEQ ID NO: 223], Val-D-Tyr-Val-Arg-NHEt [SEQ ID NO: 224].

In one embodiment, the present invention contemplates a compound of the formula: Val-Tyr-Val-Cit-Phe-Trp-NHMe [SEQ ID NO: 173].

In one embodiment, the present invention contemplates a compound of the formula: Val-Tyr-Val-Cit-Phe-Trp-NHEt [SEQ ID NO: 209].

In one embodiment, the present invention contemplates a compound of the formula: Val-Tyr-Val-Cit-Phe-Trp-NH(propyl) [SEQ ID NO: 231].

In one embodiment, the present invention contemplates a compound of the formula: Val-Tyr-Val-Cit-Phe-Trp-NH(isopropyl) [SEQ ID NO: 232].

In one embodiment, the present invention contemplates a compound of the formula: Val-Tyr-Val-Arg-Phe-D-Trp [SEQ ID NO: 210].

In one embodiment, the present invention contemplates a compound of the formula: Val-Tyr-Val-Cit-Phe-D-Trp-NH2 [SEQ ID NO: 2].

In one embodiment, the present invention contemplates a compound of the formula: Val-D-Tyr-Val-Cit-Phe-Trp-NH2 [SEQ ID NO: 212].

In one embodiment, the present invention contemplates a compound of the formula: Val-Tyr-Val-Cit-Phe-NH2 [SEQ ID NO: 213].

In one embodiment, the present invention contemplates a compound of the formula: Val-Tyr-Val-Cit-NH2 [SEQ ID NO: 214].

In one embodiment, the present invention contemplates a compound of the formula: Val-Tyr-Val-Cit-NH(isopropyl) [SEQ ID NO: 215].

In one embodiment, the present invention contemplates a compound of the formula: Val-D-Tyr-Val-Cit-NHEt [SEQ ID NO: 216].

In one embodiment, the present invention contemplates a compound of the formula: Ibutyryl-Tyr-Val-Arg-Phe-Trp [SEQ ID NO: 197], Pivaloyl-Tyr-Val-Arg-Phe-Trp [SEQ ID NO: 198], Gly-Val-Tyr-Val-Cit-Phe-Trp [SEQ ID NO: 199], Val-Tyr-Val-Cit_-Phe-Trp-Gly [SEQ ID NO: 200], Val-Tyr-Val-Cit-Phe-Trp(NMe) [SEQ ID NO: 201], Val-Tyr-Val-Arg-D-Phe-Trp [SEQ ID NO: 202], Ac-D-Trp-D-Ala-D-Arg-NH2 [SEQ ID NO: 203], Boc-D-Trp-D-Phe-D-Arg-NH2 [SEQ ID NO: 204], MeOCO-D-Trp-D-Phe-D-Arg-NH2 [SEQ ID NO: 205], Succ-Tyr-Val-Cit-Phe-Trp [SEQ ID NO: 206], Val-Tyr-Val-Orn-Phe-Trp-NH2 [SEQ ID NO: 207], Ac-Arg-Phe-Trp [SEQ ID NO: 208].

In one embodiment, the synthetic peptide is selected from the group consisting of Val-Tyr-Val-Arg-Phe-Trp-NH2 [SEQ ID NO: 19], Val-Tyr-Val-Arg-Phe-Trp-NHMe [SEQ ID NO: 217], Val-Tyr-Val-Arg-Phe-Trp-NHEt [SEQ ID NO: 218], Val-Tyr-Val-Arg-Phe-D-Trp-NH2 [SEQ ID NO: 219], Val-D-Tyr-Val-Arg-Phe-Trp-NH2 [SEQ ID NO: 220], Val-Tyr-Val-Arg-Phe-NH2 [SEQ ID NO: 221], Val-Tyr-Val-Arg-NH2 [SEQ ID NO: 222], Val-Tyr-Val-Arg-NH(isopropyl) [SEQ ID NO: 223], Val-D-Tyr-Val-Arg-NHEt [SEQ ID NO: 224].

In one embodiment, the synthetic peptide is selected from the group consisting of Val-Phe-Val-Arg-Phe-Trp [SEQ ID NO: 233], Val-Phe-Val-Arg-Phe-Trp-NH2 [SEQ ID NO: 225], Val-Phe-Val-Cit-Phe-Trp-NH2 [SEQ ID NO: 226], Val-Phe-Val-Cit-Phe-Trp-NH2 [SEQ ID NO: 226], Val-Phe-Val-Cit-Phe-Trp-NHMe [SEQ ID NO: 227], Val-Phe-Val-Cit-Phe-Trp-NHEt [SEQ ID NO: 228], Val-Phe-Val-Arg-Phe-NH(cyclopentyl) [SEQ ID NO: 229], Val-Phe-Val-Cit-Phe-NH(cyclopentyl) [SEQ ID NO: 230].

Definitions

The term "compound" or "ligand" as used herein, refers to any exogenous molecule comprising natural amino acids capable of interacting with (i.e., for example, attaching, binding etc.) to a binding partner thereby altering the biological function of the binding partner. Compounds/ligands may include, but are not limited to, an amino acid chain comprising at least two peptide bonds, antibodies, proteins, peptides, and/or tripeptides. Such compounds/ligands may be derivatized by substituents including, but not limited to, hydroxyls, sulfurs, amines, amides, ethers, esters, aliphatic chains, aromatic rings, aliphatic rings, substituted aromatic rings and/or substituted aliphatic rings. Such compounds/ligands may be an inhibitor compound/ligand, or an enhancer compound/ligand. A compound/ligand may also include a "drug", thereby referring to any pharmacologically active substance capable of being administered, which achieves a desired effect. Drugs or compounds/ligands can be synthetic or naturally occurring The term "synthetic ligand" as used herein, refers to a molecule comprising amino acids which is a ligand, and was designed ex vivo and is subsequently synthesized using in vitro, in vivo, or a combination of in vitro and in vivo means to produce a molecule of pre-specified characteristics (e.g., charge, shape, molecular weight) and is bound by another naturally occurring biomolecule to form a complex. Preferably these synthetic ligands are smaller than a target natural biomolecule, more preferably these synthetic ligands are less than 1,300 Da, and more preferably are between 350 and 1,250 Da.

The term "synthetic peptide" as used herein, refers to non-natural amino acid sequence of approximately 3-8 amino acids and ranging between approximately 350-1,500 Da. Preferably a non-natural amino acid sequence of approximately 4-5 amino acids and ranging between approximately 550-1,000 Da. For example, a synthetic peptide is six amino acids and less than 1,300 Da, for example, ranging between approximately 466-1067 Da. Preferably, a synthetic peptide is made in accordance with Example V.

The term "side chain" as used herein refers to the differentiating radical attached to the alpha carbon of an amino acid (i.e., for example, S1, S2 and/or Sn).

The term "allosteric site" as used herein, refers to a ligand binding site, other than the native chemically active/receptor binding site that, when bound to an exogenous ligand, changes the shape and activity of a protein (as an enzyme). For example, an "allosteric enhancer peptide" refers to a ligand binding to an allosteric site that may increase the native activity and/or respective affinity(ies) of the protein (e.g., for example, a PCSK9 allosteric enhancer peptide). Alternatively, an "allosteric inhibitor peptide" refers to a ligand binding to an allosteric site that may decrease the native activity and/or respective affinity(ies) of the protein (e.g., for example, a PCSK9 allosteric inhibitor peptide). For example, the binding site comprises His417, Lys421, Pro446, Trp453, Gln454, Glu628, Gly629, Asn652, and Thr653 of the PCSK9 [SEQ ID NO: 1] protein.

The term "orthosteric site" as used herein, refers to a primary, unmodulated binding site of a ligand (e.g., for example, a peptide) to a receptor, binding and/or a catalytic site.

The term "conformation" as used herein, refers to a three-dimensional stereochemical configuration of an amino acid sequence. For example, any specific conformation results from a thermodynamic balance between steric interactions, hydrophobic interactions, hydrogen bonding, electrochemical bonding and/or salt bridge interactions between individual amino acids in an amino acid sequence.

The term "conformational shift" as used herein, refers to the introduction of an exogenous force or molecule (e.g., an inhibitor peptide) that may alter a first thermodynamic balance (conformation 1) into a second thermodynamic balance (conformation 2), or enhances the dynamic range and/or the type and/or the number of metastable folding states within a lone protein, and/or a protein-ligand complex, and/or a protein-protein complex. Furthermore, a conformation shift may be predominantly exhibited under certain specific external conditions (pH, temperature, etc.) and/or during specific periods within the lifetime of a lone protein or multi-part complex, including but not limited to conditions preferential for molecular recognition, initial binding interaction, induced fit interaction, functional activity, and/or dissociation.

The term "EGFA" as used herein, refers to the most amino EGF-like domain of the low density lipoprotein receptor. For example, the EGF-like domain may comprise an extracellular portion of the LDLR receptor.

The term "LDL-R" and "LDLR" as used herein, refers to an abbreviation for the low density lipoprotein receptor. The abbreviation may be in reference to the entire LDL-R receptor protein or any portion thereof. LDL-Rs reside on a cell surface and can bind to low density lipoproteins such that the LDL-R/LDL complex become internalized within a cell (i.e., for example, a hepatocyte), wherein the LDL is released and the LDL-R is recycled back to the cell surface.

The term, "binding interface" as used herein, refers to any collection of attractive interactions (i.e., for example, hydrogen bonding, electrostatic interactions, hydrophobic interactions, etc) between the functional groups (i.e., for example, hydroxyl, amide, amine, carboxyl, amidine, guanidine, hydrocarbon, sulfonyl etc.) of at least two different molecules. The collection of attractive forces forms a stable molecular plane thereby forming a 'binding interface' between the at least two molecules.

The term "induced fit" as used herein, refers to any acceptance of a peptide requiring a change in receptor conformation. Such a conformation may be facilitated by a translational/rotational movement of amino acid side chains and flexible loops, thereby rearranging the electrostatic and/or hydrophobic fields.

The term "complex" or "composition" as used herein, refers to any chemical association of two or more ions or molecules joined usually by weak electrostatic bonds rather than by covalent bonds. For example, a complex or composition may be formed between a peptide as described herein and a PCSK9 amino acid sequence, thereby creating a peptide/PCSK9 amino acid sequence complex or composition. Optionally, such complexes or compositions may also include, but are not limited to, an LDLR amino acid sequence or any portion thereof, including but not limited to the EGFA region.

The term "hydrogen bond" as used herein, an electrostatic attraction between a hydrogen atom in one polar molecule (as of water) and a small electronegative atom (as of oxygen, nitrogen, or fluorine) in usually another molecule of the same or a different polar substance.

The term "salt bridge" as used herein, refers to any interaction or a combinations of interactions, such as hydrogen bonding and/or electrostatic interactions, which align cationic and anionic chemical structures in such a way that the charged moieties overlap.

The term "interaction" as used herein, refers to any effect that one molecule and/or functional group may have on another molecule and/or functional group. Such effects may include, but are not limited to, steric (i.e., for example, physical), electrostatic (i.e., for example, electrical attraction or repulsion), electromagnetic, hydrophilic, or hydrophobic effects.

The term "overlap" as used herein, refers to any positioning of molecules in such a way that the electronic structure of one molecule is on top of, and extending past the border of another molecule, or be positioned in this way.

The term "hypercholesterolemia" as used herein, refers to any medical condition wherein blood cholesterol levels are elevated above the clinically recommended levels. For example, if cholesterol is measured using low density lipoproteins (LDLs), hypercholesterolemia may exist if the measured LDL levels are above, for example, approximately 80 mg/dl. Alternatively, if cholesterol is measured using free plasma cholesterol, hypercholesterolemia may exist if the measured free cholesterol levels are above, for example, approximately 200-220 mg/dl.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" and/or "disorder", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The terms "increase," "enhance," "elevate," and grammatical equivalents (including "higher," "larger," etc.) when in reference to the expression of any symptom in an untreated subject relative to a treated subject, mean that the quantity and/or magnitude of the symptoms in the treated subject is greater than in the untreated subject by any amount that is recognized as clinically relevant by any medically trained personnel. In one embodiment, the quantity and/or magnitude of the symptoms in the treated subject is at least 10% greater than, at least 25% greater than, at least 50% greater than, at least 75% greater than, and/or at least 90% greater than the quantity and/or magnitude of the symptoms in the untreated subject.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in emulsion with, in solution with, mixed with, etc.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to the measure of the thermodynamic tendency of two or more molecules to assemble to form a multi-part complex and to remain assembled in said complex. For example, the SRX55 [SEQ ID NO: 2] ligand has a high affinity for PCSK9 and is thermodynamically favored to form a complex. It is understood that a change in conditions (e.g., pH during the receptor internalization process) For example, a decrease in the LDL affinity for LDLR and the two molecules may dissociate, or separate, from one another.

The term "derived from" as used herein, refers to the source of a compound or amino acid sequence. In one respect, a compound or amino acid sequence may be derived from an organism or particular species. In another respect, a compound or amino acid sequence may be derived from a larger complex or sequence. In another respect, a compound or sequence may be derived by chemical modification of part or all of an amino acid sequence found in nature.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from three or more amino acids by combination of the amino group of one acid with the carboxyl group of another and are usually obtained by partial hydrolysis of proteins. In general, a peptide comprises amino acids having an order of magnitude within the tens or smaller.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and dimethylsulfoxide, vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity.

Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity' such that there is single protein species (i.e., for example, based upon SDS-PAGE or HPLC analysis). A purified composition is not intended to mean that all trace impurities have been removed.

As used herein, the term "substantially purified" refers to molecules, such as amino acid sequences, that are removed from their natural environment, isolated or separated, and are at least 60% free, preferably 75% free, and more preferably 90% free from other components with which they are naturally associated. An "isolated polypeptide" is therefore a substantially purified polypeptide.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The terms "amino acid sequence" and "polypeptide sequence" as used herein, are interchangeable and to refer to a sequence of amino acids.

A "variant" of a protein is defined as an amino acid sequence which differs by one or more amino acids from a polypeptide sequence or any homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both.

A "deletion" is defined as a change in amino acid sequence in which one or more amino acid residues, respectively, are absent.

An "insertion" or "addition" is that change in an amino acid sequence which has resulted in the addition of one or more amino acid residues.

The term "derivative" as used herein, refers to any chemical modification of an amino acid. Illustrative of such modifications would include, but are not limited to, replacement of hydrogen by an alkyl, aryl, hydroxyl, sulfhydryl, sulfoxyl, sulfonyl, acyl, phosphoryl, alkoxyl, amino or amino heterocyclic group. For example, tyrosine is a 4-hydroxyl amino acid derivative of phenylalanine, and phosphoserine is an O-phosphoric derivative of serine. Other possible chemical modifications might include, but are not limited to, C-terminal amides, and acyl or sulfonyl N-terminal modifications.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte/target being measuring/affected. The "binding" interaction may be brief as in the situation where binding causes a chemical reaction to occur. That is typical when the binding component is an enzyme and the analyte/target is a substrate for the enzyme. Reactions resulting from contact between the binding agent and the analyte/target are also within the definition of binding for the purposes of the present invention.

The term "consensus sequence" as used herein, refers to any amino acid sequence that is common to any particular series of peptide sequences. Generally, a consensus sequence is believed to contain particular amino acid residues that play a common role in the biological activity of the particular series of peptide sequences. For example, a consensus sequence may include, but is not limited to, RFW and/or VYV. In particular, a consensus sequence may be determined by an alginment analysis. See, Table I.

TABLE I

Consensus Sequence Analysis For Representative Peptide Embodiments

| SEQUENCES | Converted to standard amino acids | Alignment | | |
|---|---|---|---|---|
| C01 (SRX55) [SEQ ID NO: 2]: Val-Tyr-Val-Arg-Phe-Trp | C01 [SEQ ID NO: 2]: Val-Tyr-Val-Arg-Phe-Trp | C03 | TLCTWSSS-- | 8 |
| C02 (SRX56) [SEQ ID NO: 5]: β-Ala-Phe(3-CH2NH2)-Val-D-Ser(p)-Phe-Trp | C02 [SEQ ID NO: 234]: Ala-Phe-Val-Ser-Phe-Trp | C07 | TLCTWSSS-- | 8 |
| C03 (SRX60) [SEQ ID NO: 6]: Thr-Leu-Cys(CH2-Ph)-Thr-Trp-Ser-Ser-Ser(p) | C03 [SEQ ID NO: 235]: Thr-Leu-Cys-Thr-Trp-Ser-Ser-Ser | C011 | ----WSS--- | 3 |
| C04 (SRX61) [SEQ ID NO: 7]: Thr-Leu-Asp(NHCH2Ph)-Thr-Trp-Ser-Ser-Ser(p) | C04 [SEQ ID NO: 236]: Thr-Leu-Asp-Thr-Trp-Ser-Ser-Ser | C05 | TLGTWSSS-- | 8 |
| C05 (SRX62) [SEQ ID NO: 8]: Thr-Leu-Gly(CH2CH2cyclohexyl)-Thr-Trp-Ser-Ser-Ser(p) | C05 [SEQ ID NO: 237]: Thr-Leu-Gly-Thr-Trp-Ser-Ser-Ser | C06 | TLFTWSSS-- | 8 |
| C06 (SRX63) [SEQ ID NO: 9]: Thr-Leu-Hph-Thr-Trp-Ser-Ser-Ser(p) | C06 [SEQ ID NO: 238]: Thr-Leu-Phe-Thr-Trp-Ser-Ser-Ser | C04 | TLDTWSSS-- | 8 |
| C07 (SRX64) [SEQ ID NO: 10]: Thr-Leu-Cys(CH2-Ph)-Thr-Trp(3-Me)-Ser-Ser-Ser(p) | C07 [SEQ ID NO: 235]: Thr-Leu-Cys-Thr-Trp-Ser-Ser-Ser | C015 | TL-TWSSS-- | 7 |
| C08 (SRX65) [SEQ ID NO: 3]: Val-Leu-Glu-Leu-Tyr-Trp | C08 [SEQ ID NO: 3]: Val-Leu-Glu-Leu-Tyr-Trp | C012 | ----WAS--- | 3 |
| C09 (SRX66) [SEQ ID NO: 11]: Leu-Asp-Leu-Phe-Phe-Ser | C09 [SEQ ID NO: 11]: Leu-Asp-Leu-Phe-Ser | C013 | ----WAS--- | 3 |
| C010 (SRX67) [SEQ ID NO: 12]: Ile-Leu-Asp-Leu-Ser-Tyr | C010 [SEQ ID NO: 12]: Ile-Leu-Asp-Leu-Ser-Tyr | C016 | ----FAS--- | 3 |
| C011 (SRX68) [SEQ ID NO: 13]: Ac-Trp-Ser-Ser(p) | C011: Trp-Ser-Ser | C038 | ----FAS--- | 3 |
| C012 (SRX69) [SEQ ID NO: 14]: Ac-Trp-Ala-Ser(p) | C012: Trp-Ala-Ser | C039 | ----FAS--- | 3 |
| C013 (SRX70) [SEQ ID NO: 15]: Ac-Trp(5-F)-Ala-Ser(p)-morpholine | C013: Trp-Ala-Ser | C037 | ----FGS--- | 3 |
| C014 (SRX72) [SEQ ID NO: 17]: Ac-Tyr-Trp-Gly | C014: Tyr-Trp-Gly | C018 | ----WFRVYV | 6 |
| C015 (SRX36) [SEQ ID NO: 16]: Thr-Leu-Thr-Trp-Ser-Ser-Ser(p) | C015 [SEQ ID NO: 239]: Thr-Leu-Thr-Trp-Ser-Ser-Ser | C022 | ----WFR--- | 3 |
| C016 (SRX73) [SEQ ID NO: 18]: Phe(4-Ph)-Ala-Ser(p)-morpholine | C016: Phe-Ala-Ser | C024 | ---VYVRFW- | 6 |
| C017 (SRX77) [SEQ ID NO: 163]: D-Val-D-Tyr-D-Val-D-Arg-D-Phe-D-Trp | C017 [SEQ ID NO: 2]: Val-Tyr-Val-Arg-Phe-Trp | C032 | ---VYVRFW- | 6 |
| C018 (SRX78) [SEQ ID NO: 164]: D-Trp-D-Phe-D-Arg-D-Val-D-Tyr-D-Val | C018 [SEQ ID NO: 240]: Trp-Phe-Arg-Val-Tyr-Val | C023 | ---VYVRFW- | 6 |
| C019 (SRX79) [SEQ ID NO: 165]: D-Arg-D-Phe-D-Trp | C019: Arg-Phe-Trp | C017 | ---VYVRFW- | 6 |
| C020 (SRX80) [SEQ ID NO: 166]: Ac-D-Arg-D-Phe-D-Trp | C020: Arg-Phe-Trp | C01 | ---VYVRFW- | 6 |
| C021 (SRX81) [SEQ ID NO: 167]: Ac-D-Arg-D-Phe-D-Trp-NH2 | C021: Arg-Phe-Trp | C019 | ------RFW- | 3 |
| C022 (SRX82) [SEQ ID NO: 168]: D-Trp-D-Phe-D-Arg | | C036 | ---VFVRFW- | 6 |
| | | C020 | ------RFW- | 3 |
| | | C025 | ---VYHRFW- | 6 |
| | | C026 | ---VYSRFW- | 6 |
| | | C027 | ---VYGRFW- | 6 |
| | | C021 | ------RFW- | 3 |
| | | C033 | ---AYVRFW- | 6 |
| | | C034 | ----YVEFW- | 5 |
| | | C035 | ----YVEF-- | 4 |
| | | C028 | ---VYVEFW- | 6 |
| | | C029 | ---VYVEFW- | 6 |
| | | C030 | ---VYVQFW- | 6 |
| | | C031 | ---VYVQFW- | 6 |

TABLE I-continued

Consensus Sequence Analysis For Representative Peptide Embodiments

| SEQUENCES | Converted to standard amino acids | Alignment |
|---|---|---|
| C023 (SRX310) [SEQ ID NO: 169]: Val-Tyr-Val-Cit-Phe-Trp-NH2 | C022: Trp-Phe-Arg | C02 ---AFVSFW- 6 |
| C024 (SRX314) [SEQ ID NO: 209]: Val-Tyr-Val-Cit-Phe-Trp-NHEt | C023 [SEQ ID NO: 2]: Val-Tyr-Val-Arg-Phe-Trp | C08 ---VLELYW- 6 |
| C025 [SEQ ID NO: 175]: Val-Tyr-His-Arg-Phe-Trp | C024 [SEQ ID NO: 2]: Val-Tyr-Val-Arg-Phe-Trp | C014 -------YWG 3 |
| C026 [SEQ ID NO: 178]: Val-Tyr-Hse-Arg-Phe-Trp | C025 [SEQ ID NO: 175]: Val-Tyr-His-Arg-Phe-Trp | C09 ----LDLFFS 6 |
| C027 [SEQ ID NO: 179]: Val-Tyr-Gly(Et)-Arg-Phe-Trp | C026 [SEQ ID NO: 177]: Val-Tyr-Ser-Arg-Phe-Trp | C010 ---ILDLSY- 6 |
| C028 [SEQ ID NO: 180]: Val-Tyr-Val-Orn-Phe-Trp | C027 [SEQ ID NO: 246]: Val-Tyr-Gly-Arg-Phe-Trp | |
| C029 [SEQ ID NO: 182]: Val-Tyr-Val-Glu-Phe-Trp | C028 [SEQ ID NO: 182]: Val-Tyr-Val-Glu-Phe-Trp | |
| C030 [SEQ ID NO: 183]: Val-Tyr-Val-Gln(N-propyl)-Phe-Trp | C029 [SEQ ID NO: 182]: Val-Tyr-Val-Glu-Phe-Trp | |
| C031 [SEQ ID NO: 184]: Val-Tyr-Val-Gln(N-2-hydroxylpropyl)-Phe-Trp | C030 [SEQ ID NO: 181]: Val-Tyr-Val-Gln-Phe-Trp | |
| C032 [SEQ ID NO: 185]: Val-Tyr-Val-(nor)Arg-Phe-Trp | C031 [SEQ ID NO: 181]: Val-Tyr-Val-Gln-Phe-Trp | |
| C033 [SEQ ID NO: 188]: D-Ala-Tyr-Val-Arg-Phe-Trp | C032 [SEO ID NO: 2]: Val-Tyr-Val-Arg-Phe-Trp | |
| C034 [SEQ ID NO: 189]: (CH3)2CHCO-Tyr-Val-Glu-Phe-Trp | C033 [SEQ ID NO: 241]: Ala-Tyr-Val-Arg-Phe-Trp | |
| C035 [SEQ ID NO: 191]: (CH3)3CCO-Tyr-Val-Glu-Phe-NH(cyclopentyl) | C034 [SEQ ID NO: 242]: Tyr-Val-Glu-Phe-Trp | |
| C036 [SEQ ID NO: 192]: Val-Phe(4-OMe)-Val-Arg-Phe(4-F)-Trp-NH2 | C035: Tyr-Val-Glu-Phe | |
| C037 [SEQ ID NO: 243]: Phe(4-Ph)-Gly(Et)-Ser(p)-morpholine | C036 [SEQ ID NO: 233]: Val-Phe-Val-Arg-Phe-Trp | |
| C038 [SEQ ID NO: 244]: Phe(4-Ph)-Ala-Ser(p)-(4-Me-piperazine) | C37: Phe-Gly-Ser | |
| C039 [SEQ ID NO: 245]: Phe[4-(3-OH)-Ph]-Ala-Ser(p)-morpholine | C38: Phe-Ala-Ser | |
| | C39: Phe-Ala-Ser | |

Chemical Terminology:
  Alkyl: a chain consisting of only carbon and hydrogen atoms such that each carbon atom directly connects to exactly 4 different atoms, using only single bonds.
  Lower alkyl: an alkyl chain containing 1-6 carbon atoms.
  Branched alkyl: an alkyl chain containing one or more carbon atoms which are directly connected to more than 2 other carbon atoms without creating a ring of carbon atoms.
  Hydroxyalkyl: an alkyl chain where at least one carbon atom is bonded to a hydoxyl, that is, —OH.
  Cycloalkyl: an alkyl chain forming a ring. Examples would include —CH2-cyclopropyl or -cyclohexyl.
  Heterocycle: a chain of atoms forming a ring and containing one or more "heteroatoms"; that is, atoms other than C or H able to form stable covalent bonds, such as N, O, or S. In this context, "heterocyle" will imply a non-aromatic ring. Examples include a tetrahydrofuran ring, with 4 carbon atoms and one oxygen, or a morpholine, with 4 carbon atoms and one nitrogen and one oxygen arranged such that the N and O are 1,4 to one another.
  Aromatic ring: a ring of atoms containing alternating single and double "pi" bonds such that the number pi electrons (typically 2 per double bonds for stable compounds) is an even number but not a multiple of four.
  Heteroaryl: an aromatic ring at least one heteroatom. In this context, the heteroaryl will imply a 3-6 membered ring.
  Acyl: a carbonyl containing radical: —CO—R. In this document, R=affords a typical peptide modifying group, such as: —CH3 (acetyl), —CH(CH2)2 (isobutyryl).
  Benzoyl: a carbonyl containing radical: —CO-Ph, where Ph=phenyl.
  Sulfonyl: a sulfonyl containing radical: —SO2-R.
  Carbamoyl: a radical: —CONR1R2
  Alkoxy: an alkyl chain containing one or more ether (—O—) linkages, such as: —CH2CH2OCH3.
  Aryl: phenyl or substituted phenyl
  Heteroaryl: a 5 or 6 membered aromatic heterocycle
  Fused heterocyle: a ring system, such as indole, containing two or more fused rings, of which at least one is a heterocycle. The rings need not be aromatic: indoline has an aromatic ring fused to a non-aromatic ring.
  Negatively charged polar group: A polar group carrying a negative charge at physiologic pH.

DETAILED DESCRIPTION OF THE INVENTION

This invention is related to the field of hypercholesterolemia. In particular, the invention provides compositions and methods to modulate circulating levels of low density lipoproteins by altering the conformation of the protein PCSK9 using a synthetic peptide and/or a synthetic peptide derivative sequences of 3-8 amino acids ranging between 350-2,000 Da. Altering the conformation of PCSK9 affects the interaction between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for peptides which can raise LDL levels.

I. Physiological Role of Native PCSK9

Proprotein convertase subtilisin/kexin type 9, also known as PCSK9, is an enzyme that in humans is encoded by the PCSK9 gene. Seidah et al., "The secretory proprotein convertase neural apoptosis-regulated convertase 1 (NARC-1): liver regeneration and neuronal differentiation" *Proc. Natl. Acad. Sci. U.S.A.* 100 (3): 928-933 (2003). Similar genes (orthologs) are found across many species. Many enzymes, including PSCK9, are inactive when they are first synthesized, because they have a section of peptide chains that blocks their activity; proprotein convertases remove that section to activate the enzyme.

Figure 8:
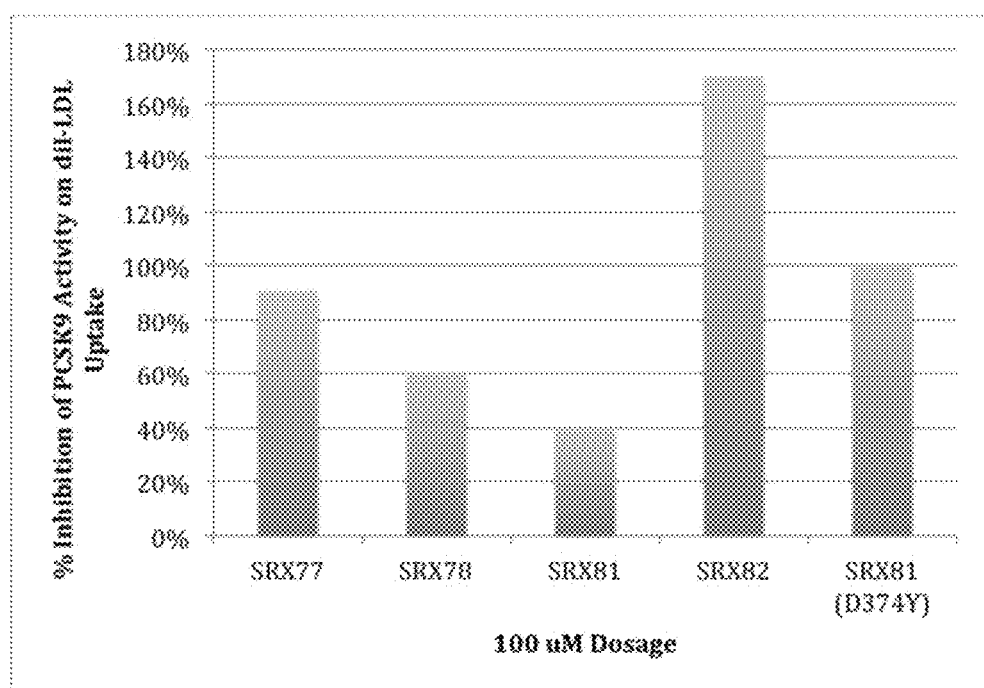
FIG. 8 shows exemplary data of % PCSK9 inhibition in HepG2 cells. The cells were incubated in a 96-well plate for a total of 20 h in the absence or presence PCSK9 protein alone (mutant D374Y: 2 nM; WT: 10 nM) or protein, pre-mixed and pre-incubated for 4 hours, with 100 uM of SRX compounds. After 16 h, dil-LDL (5 ug/ml) was added to the incubation mixtures. After 4 h, fluorescence was measured (Ex: 520 nm/Em: 575 nm; cutoff: 550 nm). The % inhibition of the PCSK9 activity on Dil-LDL uptake was calculated from relative fluorescence.
Figure 9:
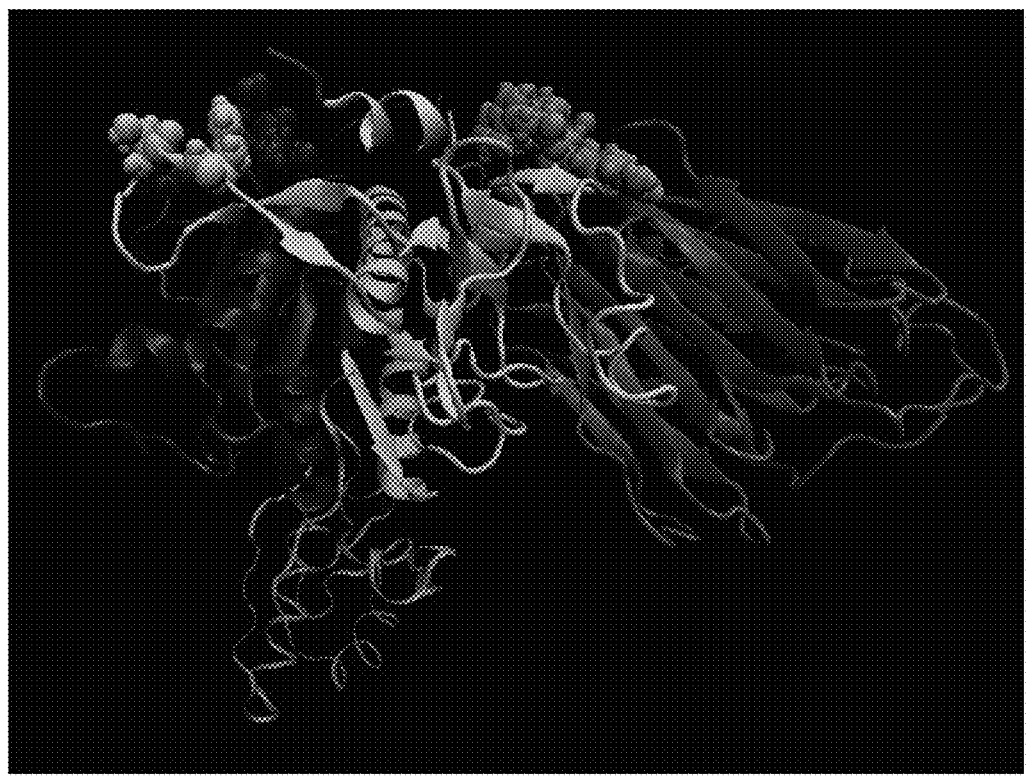
FIG. 9 presents an illustrative embodiment showing the binding of an allosteric modulatory synthetic peptide (e.g., SRX55 [SEQ ID NO: 2]) to a PCSK9 protein. The prodomain is shown in light blue. The two halves of the PCSK9 "catalytic" domain are shown as yellow and dark blue, respectively. The EGF-A binding site is shown as blue and yellow spacefill. SRX55 [SEQ ID NO: 2] (green) is shown binding to the allosteric ligand binding site. The N-terminal helix is shown in white.

An illustrative embodiment shows the binding of an allosteric modulatory synthetic peptide (e.g., SRX55 [SEQ ID NO: 2]) to a PCSK9 protein. See, FIG. 8. The prodomain is shown in light blue. The two halves of the PCSK9 "catalytic" domain are shown as yellow and dark blue, respectively. The EGF-A binding site is shown as blue and yellow spacefill. SRX55 [SEQ ID NO: 2] (green) is shown binding to the allosteric ligand binding site. The N-terminal helix is shown in white.

The PSCK9 gene encodes a proprotein convertase belonging to the proteinase K subfamily of the secretory subtilase family. The encoded protein is synthesized as a soluble zymogen that undergoes autocatalytic intramolecular processing in the endoplasmic reticulum. The protein may function as a proprotein convertase. For example, a human PCSK9 amino acid sequence [SEQ ID NO: 1] is:

```
001 mgtvssrrsw wplplllll  lllgpagara qededgdyee lvlalrseed glaeapehgt 061 tatfhrcakd pwrlpgtyvv vlkeethlsq sertarrlqa qaarrgyltk ilhvfhgllp 121 gflvkmsgdl lelalklphv dyieedssvf aqsipwnler itppryrade yqppdggslv 181 evylldtsiq sdhreiegrv mvtdfenvpe edgtrfhrqa skcdshgthl agvvsgrdag 241 vakgasmrsl rvlncqgkgt vsgtliglef irksqlvqpv gplvvllpla ggysrvlnaa 301 cqrlaragvv lvtaagnfrd daclyspasa pevitvgatn aqdqpvtlgt lgtnfgrcvd 361 lfapgediig assdcstcfv sqsgtsqaaa hvagiaamml saepeltlae lrqrlihfsa 421 kdvineawfp edqrvltpnl vaalppsthg agwqlfcrtv wsahsgptrm atavarcapd 481 eellscssfs rsgkrrgerm eaqggklvcr ahnafggegv yaiarccllp qancsvhtap 541 paeasmgtry hchqqghvlt gcsshweved lgthkppvlr prgqpnqcvg hreasihasc 601 chapgleckv kehgipapqe qvtvaceegw tltgcsalpg tshvlgayav dntcvvrsrd 661 vsttgstseg avtavaiccr srhlaqasqe lq (Accession No. NP_777596).
```

PSCK9 is believed to play a regulatory role in cholesterol homeostasis. For example, PCSK9 can bind to the epidermal growth factor-like repeat A (EGF-A) domain of the low-density lipoprotein receptor (LDL-R) resulting in LDL-R internalization and degradation. Clearly, it would be expected that reduced LDL-R levels result in decreased metabolism of LDL-C, which could lead to hypercholesterolemia.

As it is estimated that approximately 9 million Americans have a high or very high risk for heart-related problems that could benefit from PCSK9 inhibitors (especially when in combination with statins). PCSK9 inhibitors could result in such widespread usage having the potential to replace statins in certain conditions. PCSK9 has medical significance because it acts in cholesterol homeostasis. Drugs that block PCSK9 biological actions are believed to lower circulating low-density lipoprotein cholesterol (LDL-C) levels (i.e., for example, by increasing the availability of LDL-Rs and, consequently, LDL-C clearance). Such drugs are beginning Phase III clinical trials to assess their safety and efficacy in humans, and to determine if they can improve outcomes in heart disease.

Drugs that inhibit LDL-R/PCSK9 complex formation have been suggested to lower cholesterol much more than conventionally available cholesterol-lowering drugs (i.e., for example, statins). It is biologically plausible that this would also lower heart attacks and other diseases caused by raised cholesterol. Studies with humans, including phase III clinical trials now underway, are focused as to whether PCSK9 inhibition actually does lower cardiovascular disease, with acceptable side effects. Lopez D., "Inhibition of PCSK9 as a novel strategy for the treatment of hypercholesterolemia" *Drug News Perspect.* 21(6): 323-e30 (2008); Steinberg et al., "Inhibition of PCSK9: a powerful weapon for achieving ideal LDL cholesterol levels" *Proc. Natl. Acad. Sci. U.S.A.* 106(24): 9546-9547 (2009); Mayer, "Annexin A2 is a C-terminal PCSK9-binding protein that regulates endogenous low density lipoprotein receptor levels" *J. Biol. Chem.* 283(46): 31791-31801 ((2008); and Anonymous, "Bristol-Myers Squibb selects Isis drug targeting PCSK9 as development candidate for prevention and treatment of cardiovascular disease" *Press Release. FierceBiotech.* 2008-04-08.

Currently, it has been reported that PCSK9 antibody drugs are in clinical trials (e.g., for example, Sanofi/Regeneron, Amgen, Pfizer, Novartis, Roche). However, one disadvantage of antibody therapy is that the administration is performed by subcutaneous or intravenous injection. A number of monoclonal antibodies that bind to PCSK9 near the catalytic domain that interact with the LDL-R and hence inhibit LDL-R/PCSK9 complex formation are currently in clinical trials. These antibodies include AMG145 (Amgen), 1D05-IgG2 (Merck & Co.), and SAR236553/REGN727 (Aventis/Regeneron). Lambert et al., "The PCSK9 decade" *J. Lipid Res.* 53(12): 2515-2524 (2012).

Peptides that mimic the EGF-A domain of the LDL-R have been developed to inhibit LDL-R/PCSK9 complex formation. Shan et al., "PCSK9 binds to multiple receptors and can be functionally inhibited by an EGF-A peptide". *Biochem. Biophys. Res. Commun.* 375(1): 69-73 (2008). Peptidic PCSK9 inhibitors of the EGF-A binding site were identified by screening both linear and disulfide-constrained phage-displayed peptide libraries. This approach identified a 13-amino acid peptide (Pep2-8) that includes structural mimicry of the natural binding domain of LDL receptor. The peptide inhibitor binding site was determined to largely overlap with that of the EGF(A) domain; therefore, Pep2-8 acts a competitive inhibitor of LDL receptor binding. This is akin to the inhibition mechanism of anti-PCSK9 monoclonal antibodies, which also disrupt the interaction of the LDL receptor-EGF(A) domain with PCSK9. Zhang et al., "Identification of a Small Peptide That Inhibits PCSK9 Protein Binding to the Low Density Lipoprotein Receptor" *J Biol Chem* 289:942-955 (2014).

PCSK9 antisense oligonucleotides (Isis Pharmaceuticals) have been shown to increase expression of the LDL-R and decrease circulating total cholesterol levels in mice. Graham et al., "Antisense inhibition of proprotein convertase subtilisin/kexin type 9 reduces serum LDL in hyperlipidemic mice" *J. Lipid Res.* 48(4): 763-767 (2007). It has also been reported that a locked nucleic acid (Santaris Pharma) reduced PCSK9 mRNA levels in mice. Gupta et al., "A locked nucleic acid antisense oligonucleotide (LNA) silences PCSK9 and enhances LDLR expression in vitro and in vivo" *PLoS ONE* 5 (5): e10682 (2010); and Lindholm et al., "PCSK9 LNA antisense oligonucleotides induce sustained reduction of LDL cholesterol in nonhuman primates". *Mol. Ther.* 20(2):376-381 (2012). Initial clinical trials of an RNAi (ALN-PCS, Alnylam Pharmaceuticals) has shown positive results as an effective means of inhibiting LDL-R/PCSK9 complex formation. Frank-Kamenetsky et al., "Therapeutic RNAi targeting PCSK9 acutely lowers plasma cholesterol in rodents and LDL cholesterol in nonhuman primates" *Proc. Natl. Acad. Sci. U.S.A.* 105(33): 11915-11920 (2008).

II. PCSK9 Allosteric Site Modulation Peptides

Variants of PCSK9 can reduce or increase circulating cholesterol. Abifadel et al., "Mutations in PCSK9 cause autosomal dominant hypercholesterolemia" *Nat. Genet.* 34 (2): 154-156 (2003). LDL-C is normally removed from the blood when it binds to an LDL-R on the surface of liver cells, and is internalized within the hepatocyte as a receptor-ligand complex. However, when PCSK9 binds to an LDL-R, the LDL-R is concomitantly degraded along with the complexed LDL particle. However, if a PCSK9 is not bound to an LDL-R, the LDL-R is recycled after internalization thereby returning to the surface of the cell for removal of more cholesterol.

In some embodiments, the invention relates to synthetic peptide sequences of 3-8 amino acids in length, and less than approximately 1,300 Da, having a modulation effect on PCSK9's ability to form an LDL-R/PCSK9 complex. In some embodiments, the synthetic peptides comprise a lipophilic N-terminal amino acid (e.g., phenylalanine) In some embodiments, the present invention contemplate the use of peptides that bind to a PCSK9 allosteric site. In some embodiments, the peptides decrease LDL-R/PCSK9 complex formation and are thereby useful to treat various diseases comprising lipid dysregulation. In some embodiments, the peptides increase LDL-R/PCSK9 complex formation and are thereby useful in research and development of therapies relevant to LDL dysregulation.

Although it is not necessary to understand the mechanism of an invention, it is believed that "gain-of-function" (GOF) PCSK9 mutants may result in conditions including, but not limited to, hypercholesterolemia. For example, peptides (e.g., synthetic peptides and/or synthetic peptide derivatives) that bind to a PCSK9 allosteric site and increase the affinity of PCSK9's low density lipoprotein receptor for a low density lipoprotein receptor on the surface of a cell (e.g., a hepatocyte) would be expected to increase the symptoms of hypercholesterolemia by increasing low density lipoprotein receptor internalization and degradation.

Although it is not necessary to understand the mechanism of an invention, it is believed that "loss-of-function" (LOF) PCSK9 mutants may result in conditions comprising reduced low density lipoproteins and would be expected to result in hypocholesterolemia thereby reducing the risk of cardiovascular diseases, including but not limited to, coronary heart disease. For example, peptides that bind to a PCSK9 allosteric site that decrease the affinity of PCSK9's low density lipoprotein receptor binding site for a low density lipoprotein receptor on the surface of a cell (e.g., a hepatocyte) would be expected to reduce the symptoms of hypercholesterolemia by promoting low density lipoprotein internalization and clearance due to concomitant recycling of the low density lipoprotein receptor.

The presently disclosed embodiments of PCSK9 allosteric peptides have several advantages over current therapeutic strategies to control LDL discussed above. For example, small PCSK9 allosteric peptides, as contemplated herein, have the advantage that these peptides can be administered orally without immunological reactions seen with antibody administration, or systemic degradation problems as seen with nucleic acid administration (i.e., antisense or locked nucleic acids). Nonetheless, as these small peptides have long half-lives, encapsulation drug delivery systems, such as liposomes or other biodegradable protective compositions, will lengthen these half-lives to a greater extent than either antibodies or nucleic acids.

Figure 1:
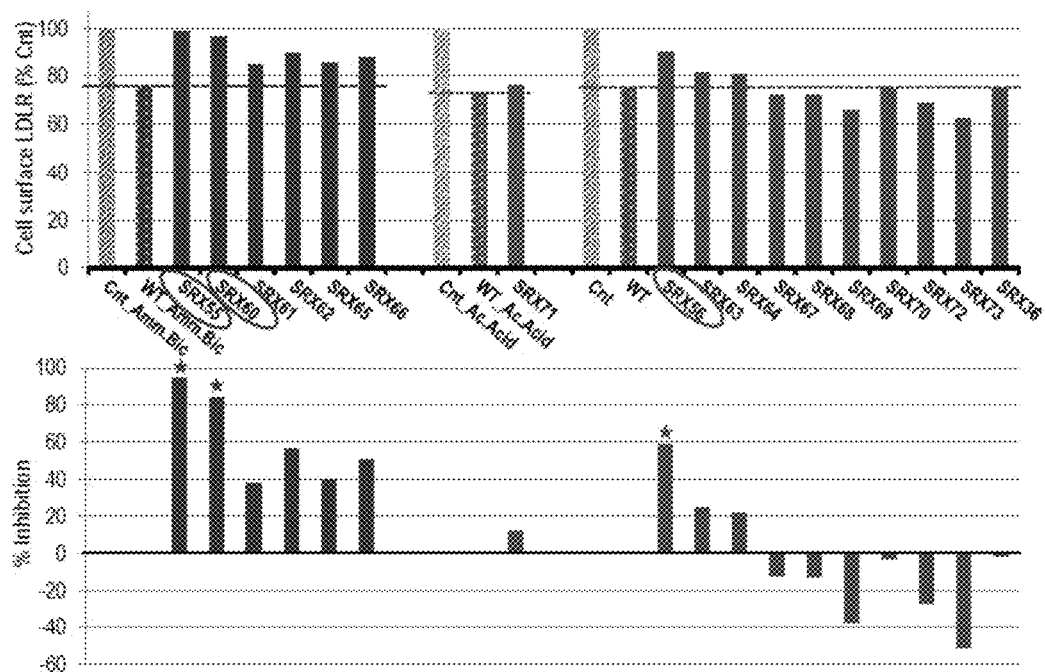
FIG. 1 shows exemplary data of WT PCSK9 inhibition as measured by FACS in HuH7 cells. HuH7 cells were incubated for 18 h in the absence (Cnt) or presence of 0.75 μg/ml PCSK9-WT protein alone (WT) or mixed with 100 μM of various SRX peptides. The level of LDLR at the cell surface was measured by FACS using anti human LDLR Ab and a suitable secondary Ab labeled with Alexa 647. Cell surface LDLR is reported relative to Cnt. % inhibition of activity was calculated as [SRX−WT]/[Cnt−WT]×100%.
Figure 2:
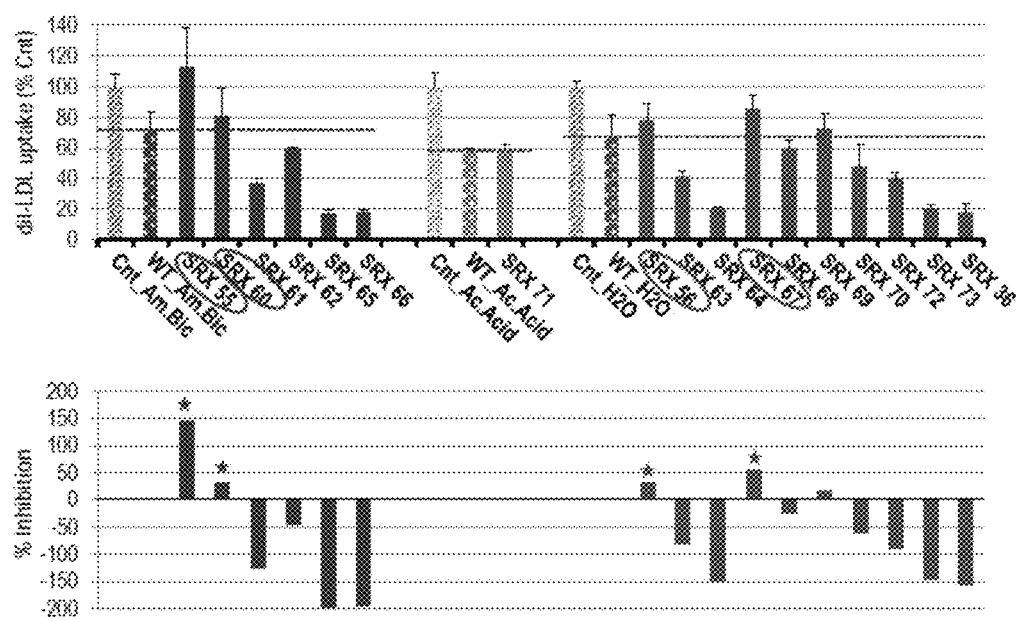
FIG. 2 shows exemplary data of WT PCSK9 activity by numerous PCSK9 allosteric modulation peptides. HuH7 cells were incubated in a 96-well plate for a total of 20 h in the absence (Cnt) or presence of 1.0 μg/ml PCSK9-WT protein alone (WT) or mixed with 100 uM of various SRX peptides. After 16 h, dil-LDL (5 ug/ml) was added to the incubation mixtures. After 4 h, fluorescence was measured (Ex: 520 nm/Em: 575 nm; cutoff: 550 nm). Dil-LDL uptake is calculated as RFU corrected for the number of cells.
Figure 3:
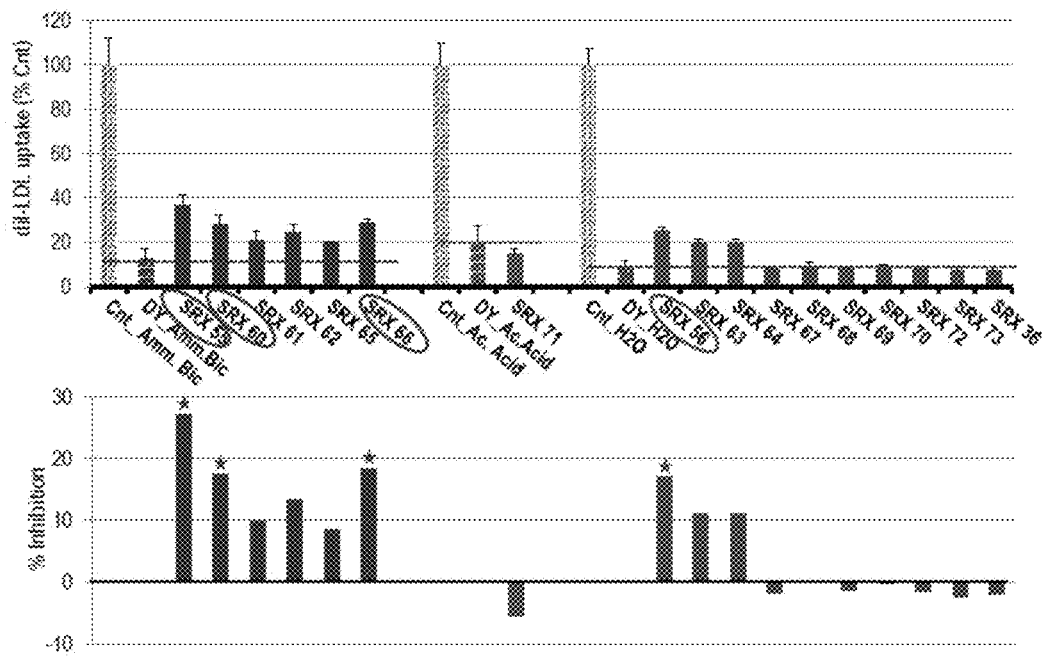
FIG. 3 shows exemplary data of a mutated PCSK9 protein ("gain of function" (GOF)-D374Y) modulation by numerous PCSK9 allosteric modulation peptides. HuH7 cells were incubated in a 96-well plate for a total of 20 h in the absence (Cnt) or presence of 0.5 μg/ml PCSK9-D374Y protein alone (DY) or mixed with 100 uM of various SRX peptides. After 16 h, dil-LDL (5 ug/ml) was added to the incubation mixtures. After 4 h, fluorescence was measured (Ex: 520 nm/Em: 575 nm; cutoff: 550 nm). Dil-LDL uptake is calculated as RFU corrected for the number of cells.
Figure 4:
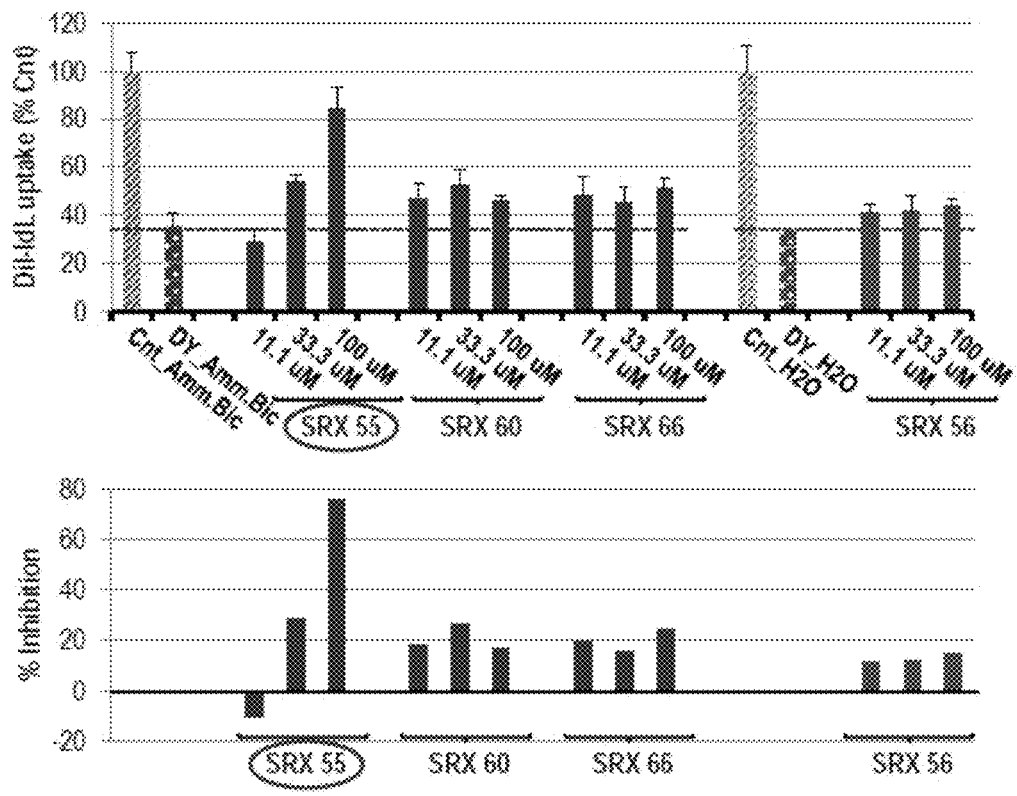
FIG. 4 shows exemplary data of a mutated PCSK9 protein ('gain of function" GOF-D374Y) modulation showing dose dependent inhibition by SRX55 [SEQ ID NO: 2], as measured by dil-LDL uptake in HuH7 cells. HuH7 cells were incubated in a 96-well plate for a total of 20 h in the absence (Cnt) or presence of 0.5 μg/ml PCSK9 GOF-D374Y protein alone (DY) or mixed with increasing concentrations of various SRX peptides. After 16 h, dil-LDL (5 ug/ml) was added to the incubation mixtures. After 4 h, fluorescence was measured (Ex: 520 nm/Em: 575 nm; cutoff: 550 nm). Dil-LDL uptake is calculated as RFU corrected for the number of cells.
Figure 5:
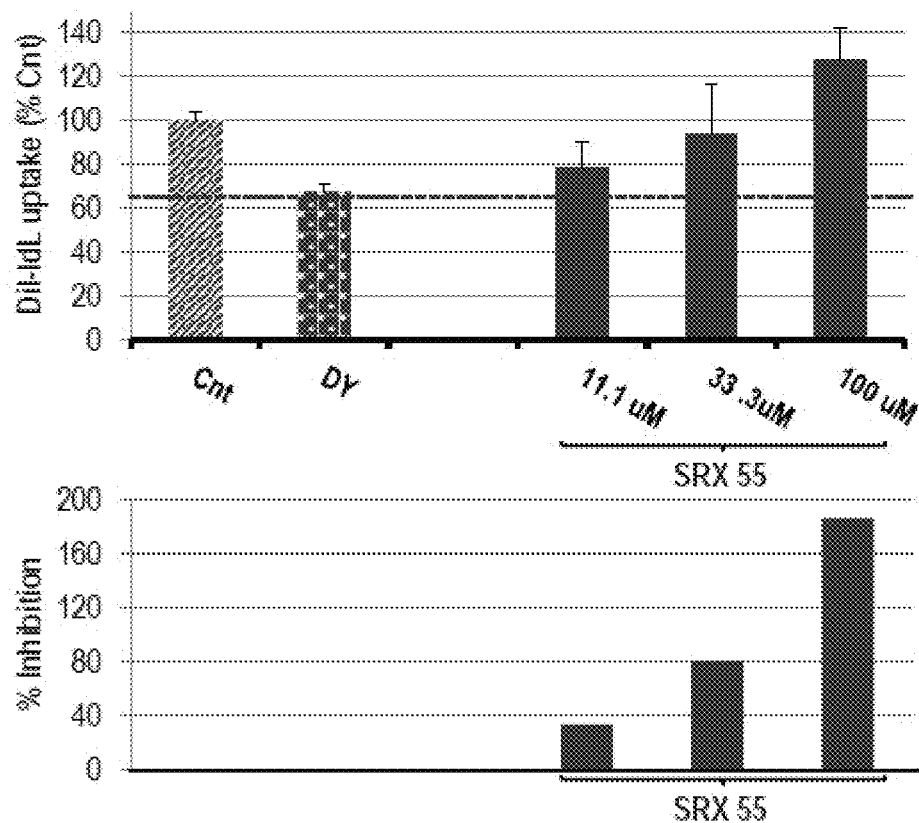
FIG. 5 shows exemplary data of a mutated PCSK9 protein ("gain of function" GOF-D374Y) modulation showing dose-dependent inhibition by SRX55 [SEQ ID NO: 2], as measured by dil-LDL uptake in HepG2 cells. HepG2 cells were incubated in a 96-well plate for a total of 20 h in the absence (Cnt) or presence of 2 μg/ml PCSK9 GOF-D374Y protein alone (DY) or mixed with increasing concentrations of SRX55 [SEQ ID NO: 2] peptide. After 16 h, dil-LDL (5 ug/ml) was added to the incubation mixtures. After 4 h, fluorescence was measured (Ex: 520 nm/Em: 575 nm; cutoff: 550 nm). Dil-LDL uptake is calculated as RFU corrected for the number of cells.
Figure 6:
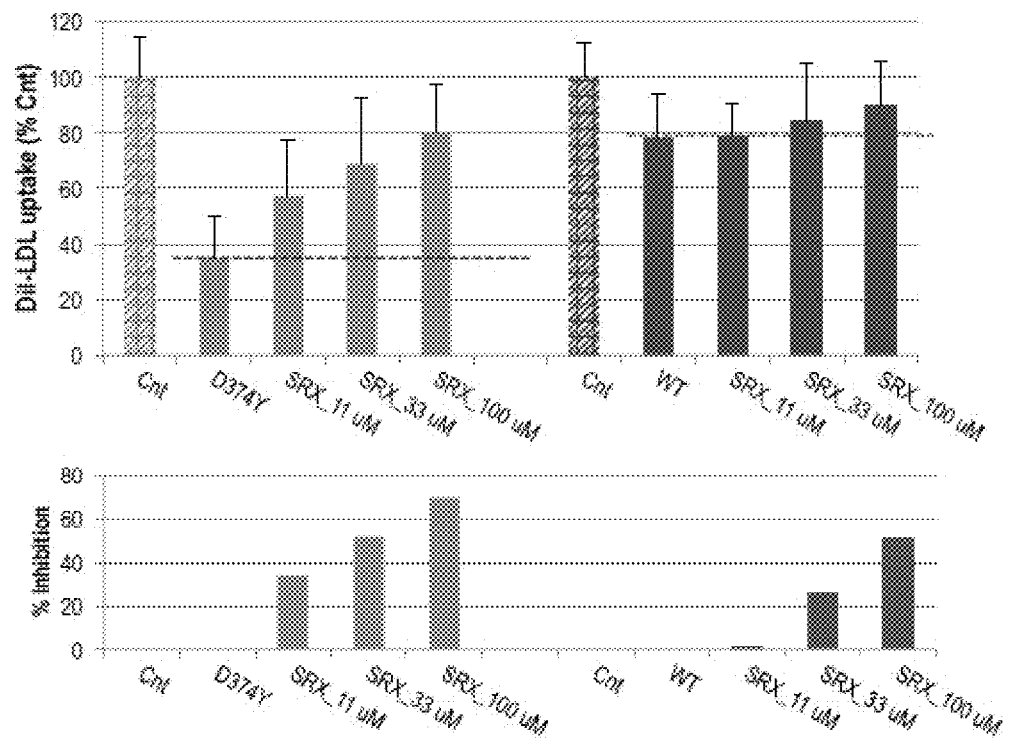
FIG. 6 shows exemplary data of HepG2 cells were incubated in a 96-well plate for a total of 20 h in the absence (Cnt) or presence PCSK9 protein alone (D374Y: 0.6 ug/ml; WT: 1.2 ug/ml) or mixed with increasing concentrations of SRX55 [SEQ ID NO: 2] peptide. After 16 h, dil-LDL (5 ug/ml) was added to the incubation mixtures. After 4 h, fluorescence was measured (Ex: 520 nm/Em: 575 nm; cutoff: 550 nm). Dil-LDL uptake is calculated as RFU corrected for the number of cells. The PCSK9 and −/+SRX55 [SEQ ID NO: 2] mixtures were pre-incubated for 3 hrs at 37 C prior to addition to the cells.
Figure 7:
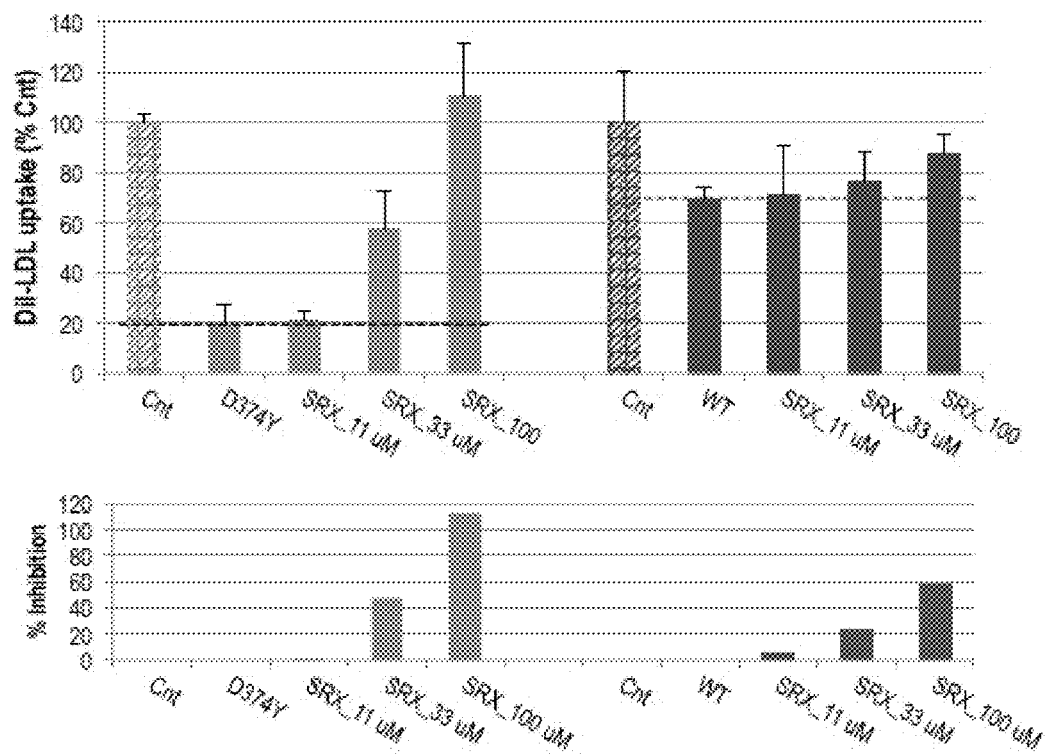
FIG. 7 shows exemplary data of FL-83B cells were incubated in a 96-well plate for a total of 20 h in the absence (Cnt) or presence PCSK9 protein alone (D374Y: 0.6 ug/ml; WT: 1.2 ug/ml) or mixed with increasing concentrations of SRX55 [SEQ ID NO: 2] peptide. After 16 h, dil-LDL (5 ug/ml) was added to the incubation mixtures. After 4 h, fluorescence was measured (Ex: 520 nm/Em: 575 nm; cutoff: 550 nm). Dil-LDL uptake is calculated as RFU corrected for the number of cells. The PCSK9 and −/+SRX55 [SEQ ID NO: 2] mixtures were pre-incubated for 3 hrs at 37 C prior to addition to the cells.

The data presented in Example m exemplifies sixteen (16) synthetic peptides having various effects on PCSK9's ability to bind to LDL-R mediated by binding to a PCSK9 allosteric site. For example, three synthetic peptides were able to increase cell surface expression of LDL-R by 60-95%, by preventing WT PCSK9/LDL-R complex formation, as measured by FACS in HuH7 cells. In particular, one synthetic peptide (SRX55 [SEQ ID NO: 2]) was able to increase cell surface expression of LDL-R by 100%, by changing WT PCSK9/LDL-R complex affinity. See, FIG. 1. These same three synthetic peptides were determined to increase LDL internalization by 30-50%, as measured by dil-LDL uptake in HuH7 cells. In another study, one peptide was able to inhibit the activity of GOF PCSK9-D374Y by 100%, as measured by di-LDL uptake in HepG2 cells, and four peptides showed a 20-30%, as measured by dil-LDL uptake in HuH7 cells. Some peptides also show inhibitory activity in mouse hepatocyte dil-LDL uptake.

Figure 10:
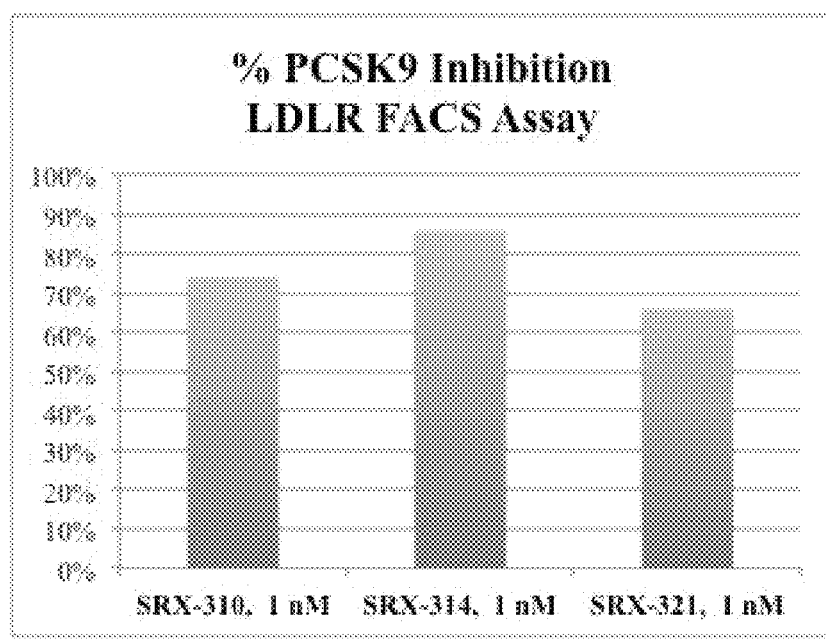
FIG. 10 shows exemplary data of % PCSK9 inhibition in HuH7 cells. The cells were incubated in 12-well plates for approximately 24 hours, followed by treatment with 10 nM of recombinant PCSK9 plus dosage with the indicated concentration of SRX compound. After a 6-hour incubation period, cells were rinsed, collected, stained with antibody and a cell viability stain, and then measured by flow cytometry (aka fluorescence activated cell sorting—FACS). PCSK9% inhibition was calculated as the % amount LDLR recovery with SRX treatment normalized by the LDLR drop caused by 10 nM PCSK9 treatment. The compounds shown are SRX310: Val-Tyr-Val-Cit-Phe-Trp-NH2 [SEQ ID NO: 169], SRX314: Val-Tyr-Val-Cit-Phe-Trp-NHEt [SEQ ID NO: 209], and SRX321: Val-Tyr-Val-Arg-Phe-NH(cyclopentyl) [SEQ ID NO: 247].

Another example of three synthetic peptides inhibiting PCSK9, and thus increasing cell surface LDLR above the tested 10 nM of recombinant PCSK9 levels, is shown in FIG. 10. In that example SRX310 [SEQ ID NO: 169], SRX314 [SEQ ID NO: 209], and SRX321 [SEQ ID NO: 247] increased cell surface LDLR levels (as measured by FACS), showing a >60% reversal of the recombinant PCSK9 activity at the indicated SRX compound dose.

In particular, the present data shows an ability of PSCK9 allosteric synthetic peptides to modulate LDLR cell surface levels by binding a peptide to PCSK9. See, FIG. 1. In that experiment, the LDLR levels of a hepatocyte culture model (HuH7 cells) were measured by fluorescence activated cell sorting (FACS) in accordance with Example III. Cell surface LDLR is reported as a percentage of Basal levels of LDLR, indicated by the Cnt_Amm.Bic, Cnt_Ac.Acid, and Cnt bars in the top graph. See, FIG. 1 (top panel). LDLR levels in the presence of exogenous PCSK9 is indicated as WT_Amm.Bic, WT-Ac.Acid, and WT, and Exogenous PCSK9 in combination with a tested peptide is indicated as SRX##. The measured LDLR levels are reported as % versus basal controls (Cnt) of the respective group. Examples of peptides (e.g., an allosteric synthetic inhibitor peptide) which positively modulate (increase) LDLR cell surface level include SRX55 [SEQ ID NO: 2], SRX56 [SEQ ID NO: 5], SRX60 [SEQ ID NO: 6], and SRX62 [SEQ ID NO: 8], and exemplary peptides (e.g., an allosteric synthetic enhancer peptide) which negatively modulate (decrease) LDLR cell surface levels include SRX69 [SEQ ID NO: 14], SRX72 [SEQ ID NO: 17], and SRX73 [SEQ ID NO: 18]. This was further shown a percent inhibition (% inhibition was calculated as [SRX−WT]/[Cnt−WT]×100%) where positive modulation (increase) of LDLR level is reported as positive % inhibition, and negative modulation (decrease) of LDLR level is reported as negative % inhibition. See, FIG. 1 (bottom panel).

The ability to modulate hepatocyte LDL internalization by the binding of a ligand to the PCSK9:LDLR complex is demonstrated in FIGS. 2 through 7. LDL internalization was measured by uptake of a fluorescently tagged LDL molecule (diI-LDL) in the absence of exogenous PCSK9 (Cnt), in the presence of exogenous PCSK9 (normal PCSK9=WT, D374Y mutant PCSK9=DY), or in the presence of PCSK9 and a tested peptide (indicated as SRX##, or SRX if a single peptide results is shown in a graph).

LDL internalization, as reported by dil-LDL % uptake vs Cnt, can be modulated in a model hepatocyte cell line (HuH7) in the presence of the tested SRX peptides. See, FIG. 2 (top panel). LDL internalization was shown to be positively modulated (increased) by allosteric synthetic inhibitor peptides such as SRX55 [SEQ ID NO: 2], SRX 56 [SEQ ID NO: 5], SRX60 [SEQ ID NO: 6], and SRX67 [SEQ ID NO: 12]. LDL internalization can be negatively modulated (decreased) by allosteric synthetic enhancer peptides such SRX36 [SEQ ID NO: 16], SRX61 [SEQ ID NO: 7], SRX64 [SEQ ID NO: 10], SRX65 [SEQ ID NO: 3], SRX66 [SEQ ID NO: 11], and SRX73 [SEQ ID NO: 18]. The percent inhibition is shown, where positive modulation (increase) in LDL internalization is reported as >0% inhibition, and negative modulation (decrease) in LDL internalization is reported as <0% inhibition. See, FIG. 2 (bottom panel).

LDL internalization, as reported by dil-LDL % uptake vs Cnt, can be modulated in a model hepatocyte cell line (HuH7) by the presence of the tested SRX peptides in combination with a clinically relevant pathologic gain-of-function D374Y exogenous PCSK9 (DY). See, FIG. 3 (top panel). LDL internalization was shown to be positively modulated (increased) by allosteric synthetic inhibitor peptides such as SRX55 [SEQ ID NO: 2], SRX 56 [SEQ ID NO: 5], SRX60 [SEQ ID NO: 6], SRX63 [SEQ ID NO: 9], SRX64 [SEQ ID NO: 10], and SRX66 [SEQ ID NO: 11]. LDL internalization can be negatively modulated (decreased) by allosteric synthetic enhancer peptides such SRX36 [SEQ ID NO: 16], SRX71, SRX72 [SEQ ID NO: 17], and SRX73 [SEQ ID NO: 18]. The percent inhibition is shown, where positive modulation (increase) in LDL internalization is reported as >0% inhibition, and negative modulation (decrease) in LDL internalization is reported as <0% inhibition. See, FIG. 3 (bottom panel).

LDL internalization, as reported by dil-LDL % uptake vs Cnt, can be positively modulated (increased) by the presence of allosteric synthetic inhibitor peptides (SRX55 [SEQ ID NO: 2], SRX 60 [SEQ ID NO: 6], SRX66 [SEQ ID NO: 11] and SRX56 [SEQ ID NO: 5]) in combination with a clinically relevant pathologic gain-of-function D374Y PCSK9 (DY). SRX55 [SEQ ID NO: 2] was shown to have a positive modulation in a dose dependent manner. See, FIG. 4 (top panel). The percent inhibition is shown, where positive modulation (increase) in LDL internalization is reported as >0% inhibition, note that SRX55 [SEQ ID NO: 2] at 11.1 uM is within sampling noise of 0%. See, FIG. 4 (bottom panel).

LDL internalization, as reported by dil-LDL % uptake vs Cnt, can be positively modulated (increased) in a second model hepatocyte cell line (HepG2) in combination with a clinically relevant pathologic gain-of-function D374Y PCSK9 (DY) in a dose dependent manner with SRX55 [SEQ ID NO: 2]. See, FIG. 5 (top panel). This positive modulation is further shown as a percent inhibition, where positive modulation (increase) in LDL internalization is reported as >0% inhibition. See, FIG. 5 (bottom panel).

LDL internalization, as reported by dil-LDL % uptake vs Cnt, can be positively modulated (increased) in a second hepatocyte cell line (HepG2) when pre incubated in combination with a clinically relevant pathologic gain-of-function D374Y PCSK9 (DY) or normal PCSK9 (WT) in a dose dependent manner with SRX55 [SEQ ID NO: 2]. See, FIG. 6 (top panel). This positive modulation is further shown as percent inhibition, where positive modulation (increase) in LDL internalization is reported as >0% inhibition. See, FIG. 6 (bottom panel).

LDL internalization, as reported by dil-LDL % uptake vs Cnt, can be positively modulated (increased) in a third hepatocyte cell line (FL83B) when pre incubated in combination with a clinically relevant pathologic gain-of-function D374Y PCSK9 (DY) or normal PCSK9 (WT) in a dose dependent manner with SRX55 [SEQ ID NO: 2]. See, FIG. 7 (top panel). This positive modulation is further shown as percent inhibition, where positive modulation (increase) in LDL internalization is reported as >0% inhibition. See, FIG. 7 (bottom panel).

An efficacious peptides (e.g., for example, SRX55 [SEQ ID NO: 2]; Compound 1) performed in consistent order across all assays and PCSK9 phenotypes. Improved peptides were then designed that were expected to have better drug-like properties, as they were designed based upon an analysis of the preliminary results. Typically, the design of these improved peptides have at least one of the first three amino acids from the C-terminus incorporated with a negatively charged polar group, such as a phosphate, a sulfate, a tetrazole or a carboxylic acid. For example, in Compound 3, the polar group comprises a phosphate group:

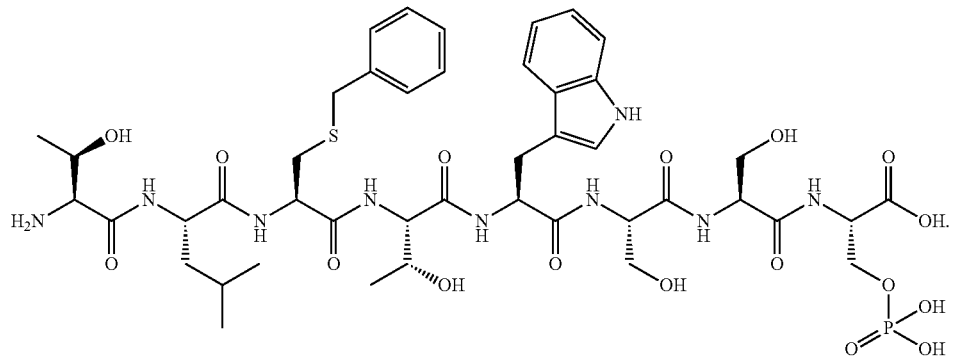

Compound 3

Thr-Leu-Cys(CH2—Ph)-Thr-Trp-Ser-Ser(p) {SEQ ID NO: 6]

Alternatively, in Compound 14, the C-terminal glycine comprises a polar group:

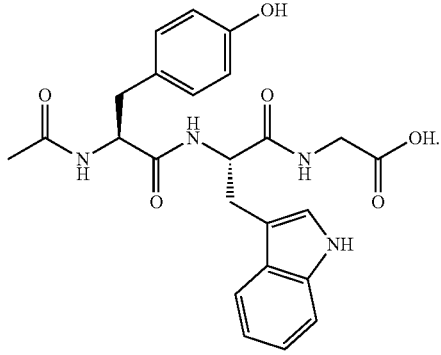

Compound 14

Ac-Tyr-Trp-Gly [SEQ ID NO: 17]

The constituent amino acids may be of defined stereochemistry, usually the natural "L" enantiomer and may have naturally occurring or synthetic side chains. The peptide "N" terminus may be free, alkylated, sulfonated, or acylated. The "C" terminus may be the carboxylic acid or an amide.

Various natural and unnatural amino acids may be contemplated. Tryptophan indole side chains may be substituted with alkyl, alkoxy, halo, carboxy, etc. to form other analogs. Phenylalanine, tyrosine, and homophenylalanine phenyl moieties may have additional phenyl substitution, such as alkyl, alkoxy, halo, carboxy, etc. Serine may be substituted in some examples by alanine Threonine may be substituted by serine or alanine Valine, leucine, and isoleucine may be interchanged in some analogs. Amino acids with carboxylic acid side chains, such as aspartic acid, may have the side chain derivatized as an amide.

Examples of synthetic allosteric peptides showing improved ability to inhibit PCSK9, demonstrated by changes in LDLR cell surface levels by binding a peptide to PCSK9 are shown as FIG. 10. In that experiment, the LDLR levels of a hepatocyte culture model (HuH7 cells) were measured by fluorescence activated cell sorting (FACS) in accordance with Example III.

III. Clinical Therapeutics

In some embodiments, the present invention contemplates the administration of a PCSK9 allosteric inhibitor peptide to a subject having a symptom of a cardiovascular disease. In one embodiment, the cardiovascular disease comprises hypercholesterolemia. In one embodiment, the cardiovascular disease comprises hypertension. In one embodiment, the hypercholesterolemia comprises elevated low density lipoprotein levels.

In some embodiments, the present invention contemplates the administration of a PCSK9 allosteric inhibitor peptide to a subject having a symptom of a metabolic disease. In one embodiment, the metabolic disease comprises diabetes.

Although it is not necessary to understand the mechanism of an invention, it is believed that the administration of a PCSK9 allosteric inhibitor synthetic peptide (i.e., for example, SRX55 [SEQ ID NO: 2]) induces a conformational shift of the PCSK9 protein such that the affinity of the low density lipoprotein binding site for a low density lipoprotein receptor is decreased, wherein PCSK9/LDL-R complex formation is decreased. The decrease in PCSK9/LDL-R complex formation results in an increase in the bioavailability of LDL-R receptors for binding to circulating LDL, thereby increasing the internalization and clearance of LDL by LDL-R. It is further believed that PCSK9 allosteric inhibitor peptides result in increased bioavailability of hepatocyte cell LDL-Rs.

A. Hypercholesterolemia

Hypercholesterolemia (also spelled hypercholesterolaemia) is the presence of high levels of cholesterol in the blood. It is a form of "hyperlipidemia" (elevated levels of lipids in the blood) and "hyperlipoproteinemia" (elevated levels of lipoproteins in the blood). Durrington, P "Dyslipidaemia" *The Lancet* 362(9385):717-731. Hypercholesterolemia is typically due to a combination of environmental and genetic factors. Environmental factors include obesity and dietary choices. Genetic contributions are usually due to the additive effects of multiple genes, though occasionally may be due to a single gene defect such as in the case of familial hypercholesterolaemia. A number of secondary causes exist including: diabetes mellitus type 2, obesity, alcohol, monoclonal gammopathy, dialysis, nephrotic syndrome, obstructive jaundice, hypothyroidism, Cushing's syndrome, anorexia nervosa, medications (thiazide diuretics, ciclosporin, glucocorticoids, beta blockers, retinoic acid). Bhatnagar et al., (2008) "Hypercholesterolaemia and its management" *BMJ* 337: a993. Genetic abnormalities are in some cases completely responsible for hypercholesterolemia, such as in familial hypercholesterolemia where there is one or more genetic mutations in the autosomal dominant APOB gene, the autosomal recessive LDLRAP1 gene, autosomal dominant familial hypercholesterolemia (HCHOLA3) variant of the PCSK9 gene, or the LDL receptor gene. "Hypercholesterolemia" *Genetics Home Reference* U.S. National Institutes of Health, ghr.nlm.nih.gov/condition=hypercholesterolemia. Even when there is no single mutation responsible for hypercholesterolemia, genetic predisposition still plays a major role in combination with sedentary lifestyle, obesity, or an atherogenic diet. Citkowitz et al., (2010) "Polygenic Hypercholesterolemia". *eMedicine Medscape*, emedicine.medscape.com/article/121424-overview.

Cholesterol is a sterol. It is one of three major classes of lipids which all animal cells utilize to construct their membranes and is thus manufactured by all animal cells. Plant cells do not manufacture cholesterol. It is also the precursor of the steroid hormones, bile acids and vitamin D. Since cholesterol is insoluble in water, it is transported in the blood plasma within protein particles (lipoproteins). Lipoproteins are classified by their density: very low density lipoprotein (VLDL), intermediate density lipoprotein (IDL), low density lipoprotein (LDL) and high density lipoprotein (HDL). Biggerstaff et al., (2004). "Understanding lipoproteins as transporters of cholesterol and other lipids" *Adv Physiol Educ* 28 (1-4): 105-6. All the lipoproteins carry cholesterol, but elevated levels of the lipoproteins other than HDL (termed non-HDL cholesterol), particularly LDL-cholesterol are associated with an increased risk of atherosclerosis and coronary heart disease. Carmena et al., (2004) "Atherogenic lipoprotein particles in atherosclerosis" *Circulation* 109 (23 Suppl 1): 1112-7. In contrast, higher levels of HDL cholesterol are protective. Kontush et al., (2006) "Antiatherogenic small, dense HDL—guardian angel of the arterial wall?" *Nat Clin Pract Cardiovasc Med* 3(3):144-153. Elevated levels of non-HDL cholesterol and LDL in the blood may be a consequence of diet, obesity, inherited (genetic) diseases (such as LDL receptor mutations in familial hypercholesterolemia), or the presence of other diseases such as diabetes and an underactive thyroid. Total cholesterol is the amount of all of the fats in your blood. These fats are called lipids. There are different types of lipid that make up your total cholesterol. The two most important types are: low density lipoprotein (LDL)—"bad" cholesterol and high density lipoprotein (HDL)—"good" cholesterol. High cholesterol, especially "bad" cholesterol (LDL), can clog your arteries. This may reduce blood flow to your heart. It can lead to heart disease, stroke, or heart attack. Cholesterol is measured in milligrams per deciliter (mg/dL). In conditions such as heart disease or diabetes, LDL cholesterol should stay below 100 mg/dL. If there is a risk for heart disease, LDL cholesterol should be lower than 130 mg/dL. In general, LDL cholesterol should be lower than 160-190 mg/dL. Alternative, HDL "good" cholesterol should be high. For example, HDL levels in men should be above 40 mg/dL, while HDL levels should be above 50 mg/dL for women.

One symptom of hypercholesterolemia comprises a long-standing elevation of serum cholesterol that can lead to atherosclerosis. Bhatnagar et al., (2008) "Hypercholesterolaemia and its management" *BMJ* 337: a993. Over a period of decades, chronically elevated serum cholesterol contributes to formation of atheromatous plaques in the arteries. This can lead to progressive stenosis (narrowing) or even complete occlusion (blockage) of the involved arteries. Alternatively smaller plaques may rupture and cause a clot to form and obstruct blood flow. Finn A V, Nakano M, Narula J, Kolodgie F D, Virmani R (July 2010). "Concept of vulnerable/unstable plaque" *Arterioscler. Thromb. Vasc. Biol.* 30(7): 1282-1292. A sudden occlusion of a coronary artery results in a myocardial infarction or heart attack. An occlusion of an artery supplying the brain can cause a stroke. If the development of the stenosis or occlusion is gradual blood supply to the tissues and organs slowly diminishes until organ function becomes impaired. At this point that tissue ischemia (restriction in blood supply) may manifest as specific symptoms including, but not limited to, temporary ischemia of the brain (commonly referred to as a transient ischemic attack) may manifest as temporary loss of vision, dizziness and impairment of balance, aphasia (difficulty speaking), paresis (weakness) and paresthesia (numbness or tingling), usually on one side of the body. Insufficient blood supply to the heart may manifest as chest pain, and ischemia of the eye may manifest as transient visual loss in one eye. Insufficient blood supply to the legs may manifest as calf pain when walking, while in the intestines it may present as abdominal pain after eating a meal. Grundy et al., (1998) "Primary prevention of coronary heart disease: guidance from Framingham: a statement for healthcare professionals from the AHA Task Force on Risk Reduction. American Heart Association" *Circulation* 97(18):1876-1887.

B. Hypocholesterolemia

Hypocholesterolemia is the presence of abnormally low (hypo-) levels of cholesterol in the blood (-emia). Although the presence of high total cholesterol (hyper-cholesterolemia) correlates with cardiovascular disease, a defect in the body's production of cholesterol can lead to adverse consequences as well. Cholesterol is an essential component of mammalian cell membranes and is required to establish proper membrane permeability and fluidity. It is not clear if a lower than average cholesterol level is directly harmful; it is often encountered in particular illnesses.

Possible causes of low cholesterol include, but are not limited to, statins, hyperthyroidism, or an overactive thyroid gland, adrenal insufficiency, liver disease, malabsorption (inadequate absorption of nutrients from the intestines), such as in celiac disease, malnutrition, abetalipoproteinemia (a genetic disease that causes cholesterol readings below 50 mg/dl), hypobetalipoproteinemia (a genetic disease that causes cholesterol readings below 50 mg/dl, manganese deficiency, Smith-Lemli-Opitz syndrome, Marfan syndrome, leukemias and other hematological diseases.

Demographic studies suggest that low cholesterol is associated with increased mortality, mainly due to depression, cancer, hemorrhagic stroke, aortic dissection and respiratory diseases. Jacobs et al., (1992). "Report of the Conference on Low Blood Cholesterol: Mortality Associations" *Circulation* 86 (3): 1046-1060; and Suarez E. C., (1999) "Relations of trait depression and anxiety to low lipid and lipoprotein concentrations in healthy young adult women". *Psychosom Med* 61(3): 273-279. It is also possible that whatever causes the low cholesterol level also causes mortality, and that the low cholesterol is simply a marker of poor health.

C. Diabetes

Diabetes affects more than 20 million Americans. Over 40 million Americans have pre-diabetes (which often develops before type 2 diabetes). Diabetes is usually a lifelong (chronic) disease in which there is a high level of sugar in the blood. Insulin is a hormone produced by the pancreas to control blood sugar. Diabetes can be caused by too little insulin, resistance to insulin, or both. To understand diabetes, it is important to first understand the normal process by which food is broken down and used by the body for energy.

Several things happen when food is digested. A sugar called glucose enters the bloodstream. Glucose is a source of fuel for the body. An organ called the pancreas makes insulin. The role of insulin is to move glucose from the bloodstream into muscle, fat, and liver cells, where it can be used as fuel.

People with diabetes have high blood sugar because their body cannot move sugar into fat, liver, and muscle cells to be stored for energy. This is because either their pancreas does not make enough insulin or their cells do not respond to insulin normally.

There are two major types of diabetes. The causes and risk factors are different for each type. Type 1 diabetes can occur at any age, but it is most often diagnosed in children, teens, or young adults. In this disease, the body makes little or no insulin. Daily injections of insulin are needed. The exact cause is unknown. Type 2 diabetes makes up most diabetes cases. It most often occurs in adulthood. But because of high obesity rates, teens and young adults are now being diagnosed with it. Many people with type 2 diabetes do not know they have it.

Gestational diabetes is high blood sugar that develops at any time during pregnancy in a woman who does not have diabetes.

Diabetes symptoms may result from high blood sugar level and include, but are not limited to, blurry vision, excess thirst, fatigue, hunger, urinating often and weight loss.

IV. Pharmaceutical Compositions

The present invention further provides pharmaceutical compositions (e.g., comprising the peptides described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, (e.g., intrathecal or intraventricular), administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral, sublingual or buccal administration include powders or granules, suspensions or solutions in water or non-aqueous media, capsules, gels, drops, strips, gums, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

In some embodiment, the pharmaceutical compositions may further comprise other drugs, hormones, and/or peptides. For example, the pharmaceutical composition may further comprise a statin drug. Statins (or HMG-CoA reductase inhibitors) are a class of drugs used to lower cholesterol levels by inhibiting the enzyme HMG-CoA reductase, which plays a role in the production of cholesterol in the liver. Increased cholesterol levels have been associated with cardiovascular diseases, and statins are therefore used in the prevention of these diseases. Lewington et al., "Blood cholesterol and vascular mortality by age, sex, and blood pressure: a meta-analysis of individual data from 61 prospective studies with 55,000 vascular deaths" *Lancet* 370 (9602): 1829-1839 (2007). Research has found that statins are most effective for treating cardiovascular disease (CVD) as a secondary prevention strategy, with questionable benefit in those with elevated cholesterol levels but without previous CVD. Taylor et al. "Statins for the primary prevention of cardiovascular disease". In: Taylor, Fiona. Cochrane Database Syst Rev (1) (2011). Statins have rare but severe adverse effects, particularly muscle damage.

Specific examples of statins include, but are not limited to, atorvastatin (Lipitor® and Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®). Several combination preparations of a statin and another agent, such as ezetimibe/simvastatin, are also available.

Specific examples of cardiovascular drugs include, but are not limited to, propranolol, digitalis, amlodipine besylate, and nifedipine.

Specific examples of other pharmaceutical compositions may further include, but are not limited to, exetimibe (Zetia®), amlodipine besylate (Norvasc®), niacin, sitagliptin (Januvia®), metformin or orlistat (Alli®/Xenical®).

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active pharmaceutical ingredient(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the peptides described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the peptide is administered in maintenance doses, ranging from 0.01 µg to 100 g per kg of body weight, once or more daily, to once every 20 years.

EXPERIMENTAL

Example I

Cell Culture and Transfections

HepG2/shPCSK9 or HuH7/shPCSK9 cells (1) lacking endogenous PCSK9 were seeded at $1 \times 10^5$ cells/well in a 12 well microplate (Greiner Bio-One). These cells were then incubated for 4 h or overnight with 0.7 µg/ml of either V5-tagged PCSK9 or its gain-of-function PCSK9-D374Y pre-incubated, or not, for 4 h with each peptide at 50 µM (or less if needed for the most active peptides). The cells were then lysed in 1×RIPA buffer (150 mM NaCl, 50 mM Tris-HCl, pH 8.0), containing 1% Nonidet P-40, 0.5% sodium deoxycholate, 0.1% SDS supplemented with 1× complete protease inhibitor mixture (Roche Applied Science), and analyzed by Western blot.

Example II

Western Blot Analyses

Proteins in the cell lysates were resolved by 10% Tris-Glycine SDS-PAGE. The gels were blotted onto polyvinylidene difluoride (PVDF, Perkin Elmer Life Sciences) membranes (GE Healthcare), blocked for 1 h in TBS-T (50 mM Tris-HCl, pH 7.5, 150 mM NaCl, 0.1% Tween 20) containing 5% nonfat milk and immunoblotted with a home-made polyclonal human PCSK9 antibody (1:1000) (13), human LDLR antibody (1:1000, R&D Systems), beta-Actin (1:5000; Sigma) and monoclonal antibody (mAb) V5-HRP (1:5000; Sigma). Appropriate horseradish peroxidase-conjugated secondary antibodies (1:10000, Sigma) were used for detection with enhanced chemiluminescence using the ECL Plus kit (GE Healthcare). Quantitation of protein bands was obtained using Image J software.

Example III

FACS Analysis

HuH7/shPCSK9 cells were incubated at 37° C. for 4 h as above with PCSK9 pre-incubated, or not, with each of the exemplified peptides used at 50 µM (or less if needed for the most active peptides). Benjannet et al., "Effects of the prosegment and pH on the activity of PCSK9: evidence for additional processing events" *J Biol Chem.* 285(52): 40965-40978 (2010). The cells were then washed 3× with solution A (calcium/magnesium-free Dulbecco's PBS (Invitrogen) containing 0.5% bovine serum albumin (Sigma) and 1 g/liter glucose)). The cells were then incubated for 10 min at room temperature with 1× Versene solution (Invitrogen) followed by the addition of 5 ml of solution A. The cells were then incubated for 40 min in solution A containing a human LDLR mAb-C7 (1:100; Santa Cruz Biotechnology). Following washes, the cells were then incubated for 20 min in solution A containing a secondary antibody (Alexa Fluor 647 donkey anti-mouse antibody; 1:250; Molecular Probes).

Following suspension in PBS containing 0.2% of propidium iodide, the cells were analyzed by FACS for both propidium iodide (dead cells) and LDLR in live cells with Alexa Fluor 647 using the FACS BD LSR (BD Biosciences).

Cell Activity of Exemplified Peptides

Compound 1 +
Compound 2 +
Compound 3 +
Compound 4 +
Compound 5 +
Compound 6 –
Compound 7 –
Compound 8 +
Compound 9 +
Compound 10 –
Compound 11 –
Compound 12 (+)
Compound 13 –
Compound 14 (+)
Compound 15 –
Compound 16 (+)
+ implies >30% inhibition above control at 100 uM
– implies inhibition within error range
(+) implies inhibition >30% below control at 100 uM (this can also be described as an "enhancer" of PCSK9 activity),

Example IV

Cellular diI-LDL Uptake Assay

Cells, such as HepG2, HuH7, FL83B or a cell line transfected with a short-hairpin PCSK9 knockdown sequence such as HepG2/shPCSK9, HuH7/shPCSK9, FL83B/shPCSK9, were seeded at $2 \times 10^4$ cells/well in a 96-well plate and cultured at 37 degC in RPMI+10% FBS. After approximately 24 hours, the cell media was aspirated off and replaced with RPMI+3-5 mg/mL LPDS (Lipoprotein Deficient Serum, Millipore) media for further experimentation. Benjannet et al., "Effects of the prosegment and pH on the activity of PCSK9: evidence for additional processing events" *J Biol Chem.* 285(52): 40965-40978 (2010).

Peptide activity was assessed by culturing cells with: i) no SRX peptide/PCSK9 protein complex (control, Cnt); ii) PCSK9 protein; and iii) SRX peptide/PCSK9 complex. Various permutations of these experimental conditions were also used, including: i) the addition of wild type PCSK9 (WT); ii) a mutant PCSK9 (e.g., D374Y mutant PCSK9, DY); iii) various SRX peptides and/or PCSK9 at the same concentration and/or combinations; iv) various SRX peptides and/or PCSK9 at different concentrations and/or combinations; v) the use of different cells, as mentioned above, with or without a transfected short-hairpin sequence; vi) a pre-incubation of the PCSK9 and SRX peptide (e.g., 1, hour, 2 hours, 3 hours, 4 hours etc.); vii) various temperatures including, but not limited to, body temperature (e.g., 37° C.), supraphysiologic temperature (e.g., 39° C.); and viii) with/without agitation (e.g., shaker or gentle periodic vortexing).

Cells were cultured using one of the combinations of conditions described in the preceding paragraph for 16 hours. After 16 hours, a quantity of diI-LDL (Low density lipoprotein coupled with 1,1'-dioctadecyl-3,3,3',3'-tetramethylindocarbocyanine perchlorate) needed to bring the media concentration to 5 ug/mL of diI-LDL was added to the culture well and cells continued to be cultured under these new conditions for 4 additional hours. At the end of the 4-hour incubation period (20 total hours of cell culture), the cellular uptake was halted with the addition of 4% formaldehyde in 10 uM Hoechst 33342 in a solvent such as deionized autoclaved water or PBS, and specimens were incubated at 20° C. for 20 minutes. Cell specimens were rinsed twice with PBS and then fluorescence measured with excitation at 360 nm and emission detected at 460 nm to measure DNA content. Cell specimens were then be incubated with a 0.1% SDS in a 0.1 N NaOH solution while being shaken for 10 minutes. Fluorescence of the diI-LDL in the specimens were quantified using excitation at 530 nm and resulting emission at 580 nm.

Fluorescence measurements of diI-LDLR were normalized to estimated cell numbers, determined from the Hoechst fluorescence. Data was analyzed for the different experimental conditions and reported as percentage relative fluorescence units (RFU) of the Cnt specimen. Percent inhibition was calculated as the difference in RFU of a peptide exposed specimen to the RFU of PCSK9-no peptide, divided by the RFU difference in PCSK9-no peptide to RFU of Cnt specimen, also expressed as [(SRX:RFU)−(PCSK9-no peptide:RFU)]/[(PCSK9-no peptide:RFU)−(Cnt:RFU)]×100.

Example V

Methods of Making PCSK9 Allosteric Inhibitor Peptides

This example presents several methods of identifying and synthesizing peptides of the present invention. R. B. Merrifield (1963). "Solid Phase Peptide Synthesis. I. The Synthesis of a Tetrapeptide". J. Am. Chem. Soc. 85 (14): 2149-2154; Albericio, F. (2000). Solid-Phase Synthesis: A Practical Guide (1 ed.). Boca Raton: CRC Press. p. 848. ISBN 0-8247-0359-6; and Albericio F, Carpino L A., "Coupling reagents and activation" Methods Enzymol. 1997; 289:104-126.

All peptides were manufactured using Fmoc (9-fluorenylmethyloxycarbonyl) chemistry (21st Century Biochemicals, 260 Cedar Hill St., Marlboro, Mass. 01752). In brief, the peptides are made using a polystyrene resin, functionalized with an appropriate linker, and the peptides are then manufactured using an Intavis RS Peptide Synthesizer (Germany) or manufactured by hand using glass peptide synthesis vessels fitted with coarse glass frits for removing reactants by vacuum (Chemglass).

In either case, the amino acids are added sequentially as follows: the amino acids are dissolved in either NMP (N-Methyl-2-pyrrolidone) or DMF (Dimethylformamide); these solvents are also used for washing the resin following each step. The Fmoc-protected amino acid to be added is activated using either HATU (O-(7-azabenzotriazol-1-yl)-N,N,N',N'-tetramethyluronium hexafluorophosphate) or HCTU (2-(6-Chloro-1H-benzotriazole-1-yl)-1,1,3,3-tetramethylaminium hexafluorophosphate); for a 4-fold stochiometric to be added (relative to the resin), a 3.95-fold excess of HATU or HCTU is used to create the active ester. Along with an 8-fold excess of DIPEA (N,N-Diisopropylethylamine) as the base, these reagents catalyze the addition of the next amino acid. Once the amino acid is coupled (each cycle includes a double coupling cycle to insure efficient coupling) the resin is exposed to 20% acetic anhydride to terminate ("cap-off") any peptide chains that have no added the next amino acid. The resin is then washed using DMF (3×), Methanol (MeOH, 2×) and DMF again, 2×. Piperidine is used to remove the Fmoc group at the end of each coupling cycle which exposes the N-terminal amine and allows the next amino acid to be added.

Once synthesis of each step is completed, the peptides (on resin) were dried using MeOH (3×) and DCM (3×), cleaved and deprotected using 92% TFA, 2% water, 2% triisopropylsilane, 2% thioanisole and 2% ethanedithiol for 3-4 h at room temperature. Peptides were precipitated in cold diethyl ether, centrifuged (2,000 RPM) and the pellets washed 2× with cold ether. After drying the peptides were solubilized in water containing 0.1% TFA (buffer A) and subjected to RP-HPLC using C18 columns (buffer B=95% acetonitrile/0.1% TFA).

Some PCSK9 allosteric synthetic peptides, and their physical characteristics, are listed below:

Compound 1 (SRX-55) [SEQ ID NO: 2]: Val-Tyr-Val-Arg-Phe-Trp, Calc'd m/z: 868.46; Obs.: 869.00

Compound 2: (SRX-56) [SEQ ID NO: 5] β-Ala-Phe(3-CH2NH2)-Val-D-Ser(p)-Phe-Trp, Calc'd m/z: 864.36; Obs.: 864.80

Compound 3 (SRX-60) [SEQ ID NO: 6]: Thr-Leu-Cys(CH2-Ph)-Thr-Trp-Ser-Ser-Ser(p), Calc'd m/z: 1053.39; Obs.: 1053.80

Compound 4 (SRX-61) [SEQ ID NO: 7]: Thr-Leu-Asp(NHCH2Ph)-Thr-Trp-Ser-Ser-Ser(p), Calc'd m/z: 1064.42; Obs.: 1064.90

Compound 5: (SRX-62) [SEQ ID NO: 8] Thr-Leu-Gly(CH2CH2cyclohexyl)-Thr-Trp-Ser-Ser-Ser(p), Calc'd m/z: 1027.46; Obs.:

Compound 6: (SRX-63) [SEQ ID NO: 9] Thr-Leu-Hph-Thr-Trp-Ser-Ser-Ser(p), Calc'd m/z: 1021.42; Obs.: 1022.30

Compound 7: (SRX-64) [SEQ ID NO: 10] Thr-Leu-Cys(CH2-Ph)-Thr-Trp(3-Me)-Ser-Ser-Ser(p), Calc'd m/z: 1067.40; Obs.: 1067.80

Compound 8: (SRX-65) [SEQ ID NO: 3] Val-Leu-Glu-Leu-Tyr-Trp, Calc'd m/z: 821.43; Obs.: 821.90

Compound 9: (SRX-66) [SEQ ID NO: 11] Leu-Asp-Leu-Phe-Phe-Ser, Calc'd m/z: 740.37; Obs.: 740.80

Compound 10: (SRX-67) [SEQ ID NO: 12] Ile-Leu-Asp-Leu-Ser-Tyr, Calc'd m/z: 722.39; Obs.: 722.80

Compound 11: (SRX-68) [SEQ ID NO: 13] Ac-Trp-Ser-Ser(p), Calc'd m/z: 500.13; Obs.: 500.15

Compound 12: (SRX-69) [SEQ ID NO: 14] Ac-Trp-Ala-Ser(p), Calc'd m/z: 484.14; Obs.: 484.40

Compound 13: (SRX-70) [SEQ ID NO: 15] Ac-Trp(5-F)-Ala-Ser(p)-morpholine, Calc'd m/z: 571.18; Obs.: 571.00

Compound 14: (SRX-72) [SEQ ID NO: 17] Ac-Tyr-Trp-Gly, Calc'd m/z: 466.19; Obs.: 466.47

Compound 15: (SRX-36) [SEQ ID NO: 16] Thr-Leu-Thr-Trp-Ser-Ser-Ser(p), Calc'd m/z: 860.33; Obs.: 860.00

Compound 16: (SRX-73) [SEQ ID NO: 18] Phe(4-Ph)-Ala-Ser(p)-morpholine, Calc'd m/z: 548.20; Obs.: 548.00

Examples of some additional PCSK9 allosteric synthetic peptide sequences are listed below:

Compound 17 (SRX77) [SEQ ID NO: 163]: D-Val-D-Tyr-D-Val-D-Arg-D-Phe-D-Trp

Compound 18 (SRX78): [SEQ ID NO: 164] D-Trp-D-Phe-D-Arg-D-Val-D-Tyr-D-Val

Compound 19 (SRX79): [SEQ ID NO: 165] D-Arg-D-Phe-D-Trp

Compound 20 (SRX80): [SEQ ID NO: 166] Ac-D-Arg-D-Phe-D-Trp

Compound 21 (SRX81) [SEQ ID NO: 167]: Ac-D-Arg-D-Phe-D-Trp-NH2

Compound 22 (SRX82) [SEQ ID NO: 168]: D-Trp-D-Phe-D-Arg

Compound 23 (SRX310) [SEQ ID NO: 169]: Val-Tyr-Val-Cit-Phe-Trp-NH2

Compound 24 (SRX314): Val-Tyr-Val-Cit-Phe-Trp-NHEt [SEQ ID NO: 209]

Compound 25 [SEQ ID NO: 175]: Val-Tyr-His-Arg-Phe-Trp

Compound 26 [SEQ ID NO: 178]: Val-Tyr-Hse-Arg-Phe-Trp

Compound 27: Val-Tyr-Gly(Et)-Arg-Phe-Trp [SEQ ID NO: 179]

Compound 28: Val-Tyr-Val-Orn-Phe-Trp [SEQ ID NO: 180]

Compound 29: Val-Tyr-Val-Glu-Phe-Trp [SEQ ID NO: 182]

Compound 30: Val-Tyr-Val-Gln(N-propyl)-Phe-Trp [SEQ ID NO: 183]

Compound 31: Val-Tyr-Val-Gln(N-2-hydroxylpropyl)-Phe-Trp [SEQ ID NO: 184]

Compound 32: Val-Tyr-Val-(nor)Arg-Phe-Trp [SEQ ID NO: 185]

Compound 33: D-Ala-Tyr-Val-Arg-Phe-Trp [SEQ ID NO: 188]

Compound 34: (CH3)2CHCO-Tyr-Val-Glu-Phe-Trp [SEQ ID NO: 189]

Compound 35: (CH3)3CCO-Tyr-Val-Glu-Phe-NH(cyclopentyl) [SEQ ID NO: 191]

Compound 36: Val-Phe(4-OMe)-Val-Arg-Phe(4-F)-Trp-NH2 [SEQ ID NO: 192]

Compound 37: Phe(4-Ph)-Gly(Et)-Ser(p)-morpholine [SEQ ID NO: 193]

Compound 38: Phe(4-Ph)-Ala-Ser(p)-(4-Me-piperazine) [SEQ ID NO: 195]

Compound 39: Phe[4-(3-OH)-Ph]-Ala-Ser(p)-morpholine [SEQ ID NO: 196]

We claim:

1. A method, comprising:
   a) providing;
      i) a PCSK9 protein, wherein said protein comprises a binding site that induces allosteric modulation and a low density lipoprotein receptor binding site;
      ii) an isolated synthetic ligand consisting of a sequence ranging between 3 to 8 amino acids, capable of binding to said binding site;
      iii) a plurality of hepatocyte cells comprising a low density lipoprotein receptor and low density lipoproteins;
   b) binding said synthetic ligand to said binding site, wherein said synthetic ligand induces a conformation shift of said protein; and
   c) modulating the affinity of said low density lipoprotein receptor binding site for said low density lipoprotein receptor by said conformational shift.

2. The method of claim 1, wherein said isolated synthetic ligand is an allosteric inhibitor ligand wherein said modulating decreases the affinity of said low density lipoprotein receptor binding site for said low density lipoprotein receptor such that internalization of said low density lipoprotein by said plurality of hepatocytes is increased.

3. The method of claim 1, wherein said isolated synthetic peptide is an allosteric enhancer ligand said modulating increases the affinity of said low density lipoprotein receptor binding site for said low density lipoprotein receptor such that internalization of said low density lipoprotein by said plurality of hepatocytes is decreased.

4. The method of claim 1, wherein said conformational shift of said protein is selected from the group consisting of an induced fit shift and a biomechanical shift.

5. The method of claim 1, wherein said isolated synthetic ligand is a synthetic peptide selected from the group consisting of VYVRFW (SEQ ID NO:2), VLELYW (SEQ ID NO:3) and ISDLSY (SEQ ID NO:4).

6. The method of claim 2, wherein said allosteric inhibitor is a peptide is selected from the group consisting of SRX55 (SEQ ID NO:2), SRX56 (SEQ ID NO:5), SRX60 (SEQ ID NO:6), SRX61 (SEQ ID NO:7), SRX62 (SEQ ID NO:8), SRX63 (SEQ ID NO:9), SRX64 (SEQ ID NO:10), SRX65 (SEQ ID NO:3) and SRX66 (SEQ ID NO:11).

7. The method of claim 3, wherein said allosteric enhancer peptide is selected from the group consisting of SRX64 (SEQ ID NO:10), SRX67 (SEQ ID NO:12), SRX68 (SEQ ID NO:13), SRX69 (SEQ ID NO:14), SRX72 (SEQ ID NO:17) and SRX73 (SEQ ID NO:18).

8. The method of claim 1, wherein said isolated synthetic ligand is a synthetic peptide selected from the group consisting of Ibutyryl-Tyr-Val-Arg-Phe-Trp (SEQ ID NO:197), Pivaloyl-Tyr-Val-Arg-Phe-Trp (SEQ ID NO:198), Gly-Val-Tyr-Val-Cit-Phe-Trp (SEQ ID NO: 199), Val-Tyr-Val-Cit_-Phe-Trp-Gly (SEQ ID NO:200), Val-Tyr-Val-Cit-Phe-Trp (NMe) (SEQ ID NO:201), Val-Tyr-Val-Arg-D-Phe-Trp (SEQ ID NO:202), Ac-D-Trp-D-Ala-D-Arg-NH2 (SEQ ID NO:203), Boc-D-Trp-DPhe-D-Arg-NH2 (SEQ ID NO:204), MeOCO-D-Trp-D-Phe-D-Arg-NH2 (SEQ ID NO:205), Succ-Tyr-Val-Cit-Phe-Trp (SEQ ID NO:206), Val-Tyr-Val-Orn-Phe-Trp-NH2 (SEQ ID NO:207), Ac-Arg-Phe-Trp (SEQ ID NO:208), Val-Tyr-Val-Cit-Phe-Trp-NH2 (SEQ ID NO: 169), Val-Tyr-Val-Cit-Phe-Trp-NHMe (SEQ ID NO: 173), Val-Tyr-Val-Cit-Phe-Trp-NHEt (SEQ ID NO:209), Val-Tyr-Val-Cit-Phe-Trp-NH(propyl) (SEQ ID NO:231), Val-Tyr-Val-Cit-Phe-Trp-NH(isopropyl) (SEQ ID NO:232), Val-Tyr-Val-Arg-Phe-D-Trp (SEQ ID NO:210), Val-Tyr-Val-Cit-Phe-D-Trp-NH2 (SEQ ID NO:211), Val-D-Tyr-Val-Cit-Phe-Trp-NH2 (SEQ ID NO:212), Val-Tyr-Val-Cit-Phe-NH2 (SEQ ID NO:213), Val-Tyr-Val-Cit-NH2 (SEQ ID NO:214), Val-Tyr-Val-Cit-NH(isopropyl) (SEQ ID NO:215), and Val-D-Tyr-Val-Cit-NHEt (SEQ ID NO:216).

9. The method of claim 1, where said isolated synthetic ligand is a compound of the formula:

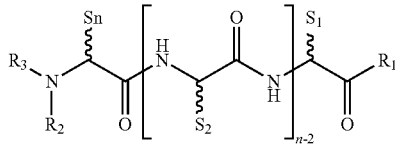

wherein: i) n, the number of amino acid residues, is an integer in the range 3-8; ii) the constituent amino acids are single enantiomers of independently selected natural or unnatural amino acids; iii) $R_2$ and $R_3$, are independently selected from the group consisting of hydrogen, a lower alkyl, a branched alkyl, a hydroxyalkyl, a cycloalkyl, a heterocycle, aryl, heteroaryl, acyl, substituted or unsubstituted benzoyl, alkyl or aryl sulfonyl, methanesulfonyl or toluenesulfonyl, and carbamoyl; iv) $R_1$ is selected from the group consisting of —OH and —$NR_4$-$R_5$; v) $R_4$ and $R_5$, independently, are selected from the group consisting of hydrogen; a lower alkyl, an aryl, a cycloalkyl, an aromatic heterocycle, pyridine, tetrazole, alkoxy; alternatively, $R_4$ and $R_5$ are joined as a heterocyle, such as piperidine; pyrrolidine; morpholine; piperazine; a substituted heterocycle, such as 4-methylpiperazine; or a fused heterocycle, such as dihydroquinoline or indoline and $S_1$, $S_2$ and $S_n$ are side chains, wherein at least one side chain is selected from the group consisting of a polar group, a negatively-charged group, and a positively charged group.

10. The method of claim 9, wherein said compound comprises an amino acid sequence of X1-X2-X3 or X3-X2-X1, wherein: X1 is an amino acid with an acidic group, an amide group, or a basic group; X2 is an amino acid with an aromatic ring; and X3 is Trp or D-Trp.

11. The method of claim 10, wherein X1 is an amino acid selected from the group consisting of Arg, Glu, Gln, Lys, Cit, Orn, Gln(N-propyl), Gln(N-2-hydroxylpropyl).

12. The method of claim 9, wherein said compound comprises an amino acid sequence of X4-X5-X6-X1-X2-X3 or X3-X2-X1-X6-X5-X4, wherein: X4 and X6 each are independently selected from the group consisting of hydrophobic amino acids; and X5 is an amino acid with an aromatic ring.

13. The method of claim 9, wherein said compound comprises an amino acid sequence of X1-X2-X3 or X3-X2-X1, wherein: X1 is an amino acid with an aromatic ring; X2 and X3 are independently selected from the group comprising of Ala, Val, Gly, Ser, Thr, Phe, and Tyr.

14. The method of claim 1, wherein three sequential amino acids of said synthetic ligand are selected from the group comprising of: Val-Tyr-Val, Arg-Phe-Trp, Cit-Phe-Trp, Val-(DTyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val.

15. A method, comprising:
 a) providing;
  i) a PCSK9 protein, wherein said protein comprises a binding site that induces allosteric modulation and a low density lipoprotein receptor binding site;
  ii) an isolated synthetic ligand consisting of a sequence of 3 to 8 amino acids, capable of binding said binding site;
  iii) a plurality of hepatocyte cells comprising a population of low density lipoprotein receptors;
 b) binding said synthetic ligand to said binding site, wherein said synthetic ligand induces a conformation shift of said protein;
 c) modulating said population of said low density lipoprotein receptors by said conformational shift.

16. The method of claim 15, wherein said isolated synthetic ligand is an allosteric inhibitor ligand wherein said modulating increases said population of said low density lipoprotein receptors measurable on the cell surface of hepatocytes.

17. The method of claim 15, wherein said isolated synthetic ligand is an allosteric enhancer ligand wherein said modulating decreases said population of said low density lipoprotein receptors measurable on the cell surface of hepatocytes.

18. The method of claim 15, wherein said conformational shift of said protein is selected from the group consisting of an induced fit shift and a biomechanical shift.

19. The method of claim 15, wherein said ligand is a synthetic peptide is selected from the group consisting of VYVRFW (SEQ ID NO:2), VLELYW (SEQ ID NO:3) and ISDLSY (SEQ ID NO:4).

20. The method of claim 16, wherein said allosteric inhibitor is a peptide is selected from the group consisting of SRX55 (SEQ ID NO:2), SRX56 (SEQ ID NO:5), SRX60 (SEQ ID NO:6), SRX61 (SEQ ID NO:7), SRX62 (SEQ ID NO:8), SRX63 (SEQ ID NO:9), SRX64 (SEQ ID NO:10), SRX65 (SEQ ID NO:3) and SRX66 (SEQ ID NO:11).

21. The method of claim 17, wherein said allosteric enhancer is a peptide is selected from the group consisting of SRX64 (SEQ ID NO: 10), SRX67 (SEQ ID NO: 12), SRX68 (SEQ ID NO:13), SRX69 (SEQ ID NO:14), SRX72 (SEQ ID NO:17) and SRX73 (SEQ ID NO:18).

22. The method of claim 15, wherein said isolated synthetic ligand is a synthetic peptide selected from the group consisting of Ibutyryl-Tyr-Val-Arg-Phe-Trp (SEQ ID NO:197), Pivaloyl-Tyr-Val-Arg-Phe-Trp (SEQ ID NO: 198), Gly-Val-Tyr-Val-Cit-Phe-Trp (SEQ ID NO: 199), Val-Tyr-Val-Cit-Phe-Trp-Gly (SEQ ID NO:200), Val-Tyr-Val-Cit-Phe-Trp(NMe) (SEQ ID NO:201), Val-Tyr-Val-Arg-D-Phe-Trp (SEQ ID NO:202), Ac-D-Trp-D-Ala-D-Arg-NH2 (SEQ ID NO:203), Boc-D-Trp-DPhe-D-Arg-NH2 (SEQ ID NO:204), MeOCO-D-Trp-D-Phe-D-Arg-NH2 (SEQ ID NO:205), Succ-Tyr-Val-Cit-Phe-Trp (SEQ ID NO:206), Val-Tyr-Val-Orn-Phe-Trp-NH2 (SEQ ID NO:207), Ac-Arg-Phe-Trp (SEQ ID NO:208), Val-Tyr-Val-Cit-Phe-Trp-NH2 (SEQ ID NO: 169), Val-Tyr-Val-Cit-Phe-Trp-NHMe (SEQ ID NO: 173), Val-Tyr-Val-Cit-Phe-Trp-NHEt (SEQ ID NO:209), Val-Tyr-Val-Cit-Phe-Trp-NH(propyl) (SEQ ID NO:231), Val-Tyr-Val-Cit-Phe-Trp-NH(isopropyl) (SEQ ID NO:232), Val-Tyr-Val-Arg-Phe-D-Trp (SEQ ID NO:210), Val-Tyr-Val-Cit-Phe-D-Trp-NH2 (SEQ ID NO:211), Val-D-Tyr-Val-Cit-Phe-Trp-NH2 (SEQ ID NO:212), Val-Tyr-Val-Cit-Phe-NH2 (SEQ ID NO:213), Val-Tyr-Val-Cit-NH2 (SEQ ID NO:214), Val-Tyr-Val-Cit-NH(isopropyl) (SEQ ID NO:215), and Val-D-Tyr-Val-Cit-NHEt (SEQ ID NO:216).

23. The method of claim 15, wherein three sequential amino acids of said isolated synthetic ligand are selected from the group comprising of: Val-Tyr-Val, Arg-Phe-Trp, Cit-Phe-Trp, Val-(DTyr)-Val, Trp-Phe-Cit, Trp-Phe-Arg, Trp-Ser-Ser, Ser-Ser-Trp, Arg-Phe-(D-Trp), Cit-Phe-(D-Trp), Val-Phe-Val.

24. The method of claim 15, where said isolated synthetic ligand is a compound of the formula:

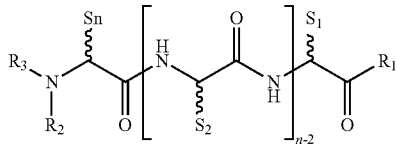

wherein: i) n, the number of amino acid residues, is an integer in the range 3-8; ii) the constituent amino acids are single enantiomers of independently selected natural or unnatural amino acids; iii) $R_2$ and $R_3$, are independently selected from the group consisting of hydrogen, a lower alkyl, a branched alkyl, a hydroxyalkyl, a cycloalkyl, a heterocycle, aryl, heteroaryl, acyl, substituted or unsubstituted benzoyl, alkyl or aryl sulfonyl, methanesulfonyl or toluenesulfonyl, and carbamoyl; iv) $R_1$ is selected from the group consisting of —OH and —$NR_4$-$R_5$; v) $R_4$ and $R_5$, independently, are selected from the group consisting of hydrogen; a lower alkyl, an aryl, a cycloalkyl, an aromatic heterocycle, pyridine, tetrazole, alkoxy; alternatively, $R_4$ and $R_5$ are joined as a heterocycle, such as piperidine; pyrrolidine; morpholine; piperazine; a substituted heterocycle, such as 4-methylpiperazine; or a fused heterocycle, such as dihydroquinoline or indoline and $S_1$, $S_2$ and $S_n$ are side chains, wherein at least one side chain is selected from the group consisting of a polar group, a negatively-charged group, and a positively charged group.

25. The method of claim 24, wherein said compound comprises an amino acid sequence of X1-X2-X3 or X3-X2-X1, wherein: X1 is an amino acid with an acidic group, an amide group, or a basic group; X2 is an amino acid with an aromatic ring; and X3 is Trp or D-Trp.

26. The method of claim 25, wherein X1 is an amino acid selected from the group consisting of Arg, Glu, Gln, Lys, Cit, Orn, Gln(N-propyl), Gln(N-2-hydroxylpropyl).

27. The method of claim 24, wherein said compound comprises an amino acid sequence of X4-X5-X6-X1-X2-X3 or X3-X2-X1-X6-X5-X4, wherein: X4 and X6 each are independently selected from the group consisting of hydrophobic amino acids; and X5 is an amino acid with an aromatic ring.

28. The method of claim 24, wherein said compound comprises an amino acid sequence of X1-X2-X3 or X3-X2-X1, wherein: X1 is an amino acid with an aromatic ring; X2 and X3 are independently selected from the group comprising of Ala, Val, Gly, Ser, Thr, Phe, and Tyr.

* * * * *

SEQUENCE LISTING

```
<160> NUMBER OF SEQ ID NOS: 248

<210> SEQ ID NO 1
<211> LENGTH: 692
<212> TYPE: PRT
<213> ORGANISM: Homo sapiens

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270
```

-continued

```
Lys Ser Gln Leu Val Gln Pro Val Gly Pro Leu Val Leu Leu Pro
            275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
```

690

<210> SEQ ID NO 2
<211> LENGTH: 6
<212> TYPE: PRT
<213> ORGANISM: Artificial sequence
<220> FEATURE:
<223> OTHER INFORMATION: Synthetic

<400> SEQUENCE: 2

Val Tyr Val Arg Phe Trp
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic

<400> SEQUENCE: 3

Val Leu Glu Leu Tyr Trp
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic

<400> SEQUENCE: 4

Ile Ser Asp Leu Ser Tyr
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: beta-Alanine
<220> FEATURE:
<221> NAME/KEY: MISC_FEATURE
<222> LOCATION: (2)..(2)
<223> OTHER INFORMATION: L-Phenylalanine-3-CH2NH2
<220> FEATURE:
<221> NAME/KEY: MISC_FEATURE
<222> LOCATION: (4)..(4)
<223> OTHER INFORMATION: D-Serine-O-phosphate

<400> SEQUENCE: 5

Xaa Xaa Val Xaa Phe Trp
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE

```
<222> LOCATION: (8)..(8)
<223> OTHER INFORMATION: L-Serine-O-phosphate

<400> SEQUENCE: 6

Thr Leu Xaa Thr Trp Ser Ser Xaa
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 7

Thr Leu Xaa Thr Trp Ser Ser Xaa
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate

<400> SEQUENCE: 8

Thr Leu Xaa Thr Trp Ser Ser Xaa
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate

<400> SEQUENCE: 9

Thr Leu Xaa Thr Trp Ser Ser Xaa
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-Tryptophan-3-methyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 10

Thr Leu Xaa Thr Xaa Ser Ser Xaa
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic

<400> SEQUENCE: 11

Leu Asp Leu Phe Phe Ser
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic

<400> SEQUENCE: 12

Ile Leu Asp Leu Ser Tyr
1               5

<210> SEQ ID NO 13
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate

<400> SEQUENCE: 13

Trp Ser Xaa
1

<210> SEQ ID NO 14
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated
<220> FEATURE:
<221> NAME/KEY: MISC_FEATURE
<222> LOCATION: (3)..(3)
<223> OTHER INFORMATION: L-Serine-O-phosphate
```

```
<400> SEQUENCE: 14

Trp Ala Xaa
1

<210> SEQ ID NO 15
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 5-fluoro-L-Tryptophan
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-Terminal morpholine

<400> SEQUENCE: 15

Xaa Ala Xaa
1

<210> SEQ ID NO 16
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: L-Serine-O-phosphate

<400> SEQUENCE: 16

Thr Leu Thr Trp Ser Ser Xaa
1               5

<210> SEQ ID NO 17
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue

<400> SEQUENCE: 17

Tyr Trp Gly
1

<210> SEQ ID NO 18
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: 4-phenyl-phenylalanine
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal morpholine

<400> SEQUENCE: 18

Xaa Ala Xaa
1

<210> SEQ ID NO 19
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: C-terminal NH2

<400> SEQUENCE: 19

Val Tyr Val Arg Phe Trp
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: L-Phenylalanine-3-CH2NH2
<220> FEATURE:
<221> NAME/KEY: MISC_FEATURE
<222> LOCATION: (4)..(4)
<223> OTHER INFORMATION: D-Serine-O-phosphate
<220> FEATURE:
<221> NAME/KEY: MISC_FEATURE
<222> LOCATION: (6)..(6)
<223> OTHER INFORMATION: terminal NH2

<400> SEQUENCE: 20

Ala Xaa Val Xaa Phe Trp
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 21
```

```
Thr Leu Xaa Thr Trp Ser Ser Xaa
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 22

Thr Leu Xaa Thr Trp Ser Ser Xaa
1               5

<210> SEQ ID NO 23
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 23

Thr Leu Xaa Thr Trp Ser Ser Xaa
1               5

<210> SEQ ID NO 24
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 24

Thr Leu Xaa Thr Trp Ser Ser Xaa
1               5
```

```
<210> SEQ ID NO 25
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-cysteine-S-benzyl
<220> FEATURE:
<221> NAME/KEY: MISC_FEATURE
<222> LOCATION: (5)..(5)
<223> OTHER INFORMATION: L-tryptophan-3-methyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 25

Thr Leu Xaa Thr Xaa Ser Ser Xaa
1               5

<210> SEQ ID NO 26
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: C-terminal NH2

<400> SEQUENCE: 26

Val Leu Glu Leu Tyr Trp
1               5

<210> SEQ ID NO 27
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: C-terminal NH2

<400> SEQUENCE: 27

Leu Asp Leu Phe Phe Ser
1               5

<210> SEQ ID NO 28
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: C-terminal NH2

<400> SEQUENCE: 28

Ile Leu Asp Leu Ser Tyr
1               5
```

```
<210> SEQ ID NO 29
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal NH2

<400> SEQUENCE: 29

Trp Ser Xaa
1

<210> SEQ ID NO 30
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal NH2

<400> SEQUENCE: 30

Trp Ala Xaa
1

<210> SEQ ID NO 31
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 5-fluoro-L-Tryptophan
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal NH2

<400> SEQUENCE: 31

Xaa Ala Xaa
1
```

```
<210> SEQ ID NO 32
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 32

Thr Leu Thr Trp Ser Ser Xaa
1               5

<210> SEQ ID NO 33
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal NHMe

<400> SEQUENCE: 33

Trp Ser Xaa
1

<210> SEQ ID NO 34
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal NHMe

<400> SEQUENCE: 34

Trp Ala Xaa
1

<210> SEQ ID NO 35
<211> LENGTH: 3
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-Terminal morpholine

<400> SEQUENCE: 35

Trp Ala Xaa
1

<210> SEQ ID NO 36
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal 4-methylpiperazine

<400> SEQUENCE: 36

Trp Ala Xaa
1

<210> SEQ ID NO 37
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal piperidine

<400> SEQUENCE: 37

Trp Ala Xaa
1

<210> SEQ ID NO 38
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
```

```
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal pyrrolidine

<400> SEQUENCE: 38

Trp Ala Xaa
1

<210> SEQ ID NO 39
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 39

Thr Leu Xaa Thr Trp Ser Ser Xaa
1               5

<210> SEQ ID NO 40
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 40

Thr Leu Xaa Thr Trp Ser Ser Xaa
1               5

<210> SEQ ID NO 41
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
```

```
<221> NAME/KEY: MISC_FEATURE
<222> LOCATION: (6)..(6)
<223> OTHER INFORMATION: Homophenylalanine
<220> FEATURE:
<221> NAME/KEY: MISC_FEATURE
<222> LOCATION: (11)..(11)
<223> OTHER INFORMATION: L-Serine-O-phosphate
<220> FEATURE:
<221> NAME/KEY: MISC_FEATURE
<222> LOCATION: (16)..(16)
<223> OTHER INFORMATION: L-Serine-O-phosphate

<400> SEQUENCE: 41

Thr Leu Xaa Thr Leu Xaa Thr Trp Ser Ser Xaa Thr Trp Ser Ser Xaa
1               5                   10                  15

<210> SEQ ID NO 42
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate

<400> SEQUENCE: 42

Thr Leu Xaa Thr Trp Ser Ser Xaa
1               5

<210> SEQ ID NO 43
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-cysteine-S-benzyl
<220> FEATURE:
<221> NAME/KEY: MISC_FEATURE
<222> LOCATION: (5)..(5)
<223> OTHER INFORMATION: L-tryptophan-3-methyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 43

Thr Leu Xaa Thr Xaa Ser Ser Xaa
1               5

<210> SEQ ID NO 44
<211> LENGTH: 6
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: N-Terminal aceylated residue

<400> SEQUENCE: 44

Val Leu Glu Leu Tyr Trp
1               5

<210> SEQ ID NO 45
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue

<400> SEQUENCE: 45

Leu Asp Leu Phe Phe Ser
1               5

<210> SEQ ID NO 46
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue

<400> SEQUENCE: 46

Ile Ser Asp Leu Ser Tyr
1               5

<210> SEQ ID NO 47
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (7)..(7)
<223> OTHER INFORMATION: L-Serine-O-phosphate

<400> SEQUENCE: 47

Thr Leu Thr Trp Ser Ser Xaa
1               5

<210> SEQ ID NO 48
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate
```

```
<400> SEQUENCE: 48

Thr Leu Xaa Thr Trp Ser Ala Xaa
1               5

<210> SEQ ID NO 49
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 49

Thr Leu Xaa Thr Trp Ser Ala Xaa
1               5

<210> SEQ ID NO 50
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate

<400> SEQUENCE: 50

Thr Leu Xaa Thr Trp Ser Ala Xaa
1               5

<210> SEQ ID NO 51
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate

<400> SEQUENCE: 51

Thr Leu Xaa Thr Trp Ser Ala Xaa
1               5

<210> SEQ ID NO 52
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
```

<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-tryptophan-3-methyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 52

Thr Leu Xaa Thr Xaa Ser Ala Xaa
1               5

<210> SEQ ID NO 53
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: L-Serine-O-phosphate

<400> SEQUENCE: 53

Thr Leu Thr Trp Ser Ala Xaa
1               5

<210> SEQ ID NO 54
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 54

Thr Leu Xaa Thr Trp Ser Ala Xaa
1               5

<210> SEQ ID NO 55
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 55

Thr Leu Xaa Thr Trp Ser Ala Xaa
1               5

<210> SEQ ID NO 56
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 56

Thr Leu Xaa Thr Trp Ser Ala Xaa
1               5

<210> SEQ ID NO 57
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 57

Thr Leu Xaa Thr Trp Ser Ala Xaa
1               5

<210> SEQ ID NO 58
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-tryptophan-3-methyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 58

```
Thr Leu Xaa Thr Xaa Ser Ala Xaa
1               5
```

<210> SEQ ID NO 59
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 59

```
Thr Leu Thr Trp Ser Ala Xaa
1               5
```

<210> SEQ ID NO 60
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 60

```
Thr Leu Xaa Thr Trp Ser Ala Xaa
1               5
```

<210> SEQ ID NO 61
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 61

```
Thr Leu Xaa Thr Trp Ser Ala Xaa
1               5
```

<210> SEQ ID NO 62
<211> LENGTH: 8
<212> TYPE: PRT
<213> ORGANISM: Artificial sequence

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate

<400> SEQUENCE: 62

Thr Leu Xaa Thr Trp Ser Ala Xaa
1               5

<210> SEQ ID NO 63
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate

<400> SEQUENCE: 63

Thr Leu Xaa Thr Trp Ser Ala Xaa
1               5

<210> SEQ ID NO 64
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-tryptophan-3-methyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 64

Thr Leu Xaa Thr Xaa Ser Ala Xaa
1               5

<210> SEQ ID NO 65
<211> LENGTH: 7
<212> TYPE: PRT
<213> ORGANISM: Artificial sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (7)..(7)
<223> OTHER INFORMATION: L-Serine-O-phosphate

<400> SEQUENCE: 65

Thr Leu Thr Trp Ser Ala Xaa
1               5

<210> SEQ ID NO 66
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 66

Thr Leu Xaa Thr Trp Ser Ala Xaa
1               5

<210> SEQ ID NO 67
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 67

Thr Leu Xaa Thr Trp Ser Ala Xaa
1               5

<210> SEQ ID NO 68
<211> LENGTH: 8
<212> TYPE: PRT
<213> ORGANISM: Artificial sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 68

Thr Leu Xaa Thr Trp Ser Ala Xaa
1               5

<210> SEQ ID NO 69
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 69

Thr Leu Xaa Thr Trp Ser Ala Xaa
1               5

<210> SEQ ID NO 70
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-Tryptophan-3-methyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
```

```
<223> OTHER INFORMATION: C-terminal NH2

<400> SEQUENCE: 70

Thr Leu Xaa Thr Xaa Ser Ala Xaa
1               5

<210> SEQ ID NO 71
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 71

Thr Leu Thr Trp Ser Ala Xaa
1               5

<210> SEQ ID NO 72
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (7)..(7)
<223> OTHER INFORMATION: L-Serine-O-phosphate

<400> SEQUENCE: 72

Thr Leu Xaa Thr Trp Ser Xaa
1               5

<210> SEQ ID NO 73
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (7)..(7)
<223> OTHER INFORMATION: L-Serine-O-phosphate

<400> SEQUENCE: 73

Thr Leu Xaa Thr Trp Ser Xaa
1               5

<210> SEQ ID NO 74
<211> LENGTH: 7
<212> TYPE: PRT
<213> ORGANISM: Artificial sequence
```

```
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (7)..(7)
<223> OTHER INFORMATION: L-Serine-O-phosphate

<400> SEQUENCE: 74

Thr Leu Xaa Thr Trp Ser Xaa
1               5

<210> SEQ ID NO 75
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (7)..(7)
<223> OTHER INFORMATION: L-Serine-O-phosphate

<400> SEQUENCE: 75

Thr Leu Xaa Thr Trp Ser Xaa
1               5

<210> SEQ ID NO 76
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-Tryptophan-3-methyl
<220> FEATURE:
<221> NAME/KEY: MISC_FEATURE
<222> LOCATION: (7)..(7)
<223> OTHER INFORMATION: L-Serine-O-phosphate

<400> SEQUENCE: 76

Thr Leu Xaa Thr Xaa Ser Xaa
1               5

<210> SEQ ID NO 77
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: L-Serine-O-phosphate

<400> SEQUENCE: 77

Thr Leu Thr Trp Ser Xaa
1               5
```

```
<210> SEQ ID NO 78
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (7)..(7)
<223> OTHER INFORMATION: L-Serine-O-phosphate

<400> SEQUENCE: 78

Thr Leu Xaa Thr Trp Ser Xaa
1               5

<210> SEQ ID NO 79
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 79

Thr Leu Xaa Thr Trp Ser Xaa
1               5

<210> SEQ ID NO 80
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 80
```

```
Thr Leu Xaa Thr Trp Ser Xaa
1               5
```

<210> SEQ ID NO 81
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (7)..(7)
<223> OTHER INFORMATION: C-terminal NH2
<220> FEATURE:
<221> NAME/KEY: MISC_FEATURE
<222> LOCATION: (7)..(7)
<223> OTHER INFORMATION: L-Serine-O-phosphate

<400> SEQUENCE: 81

```
Thr Leu Xaa Thr Trp Ser Xaa
1               5
```

<210> SEQ ID NO 82
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-Tryptophan-3-methyl
<220> FEATURE:
<221> NAME/KEY: MISC_FEATURE
<222> LOCATION: (7)..(7)
<223> OTHER INFORMATION: L-Serine-O-phosphate

<400> SEQUENCE: 82

```
Thr Leu Xaa Thr Xaa Ser Xaa
1               5
```

<210> SEQ ID NO 83
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (6)..(6)
<223> OTHER INFORMATION: L-Serine-O-phosphate
<220> FEATURE:
<221> NAME/KEY: MISC_FEATURE

```
<222> LOCATION: (6)..(6)
<223> OTHER INFORMATION: C-terminal NH2

<400> SEQUENCE: 83

Thr Leu Thr Trp Ser Xaa
1               5

<210> SEQ ID NO 84
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (7)..(7)
<223> OTHER INFORMATION: L-Serine-O-phosphate

<400> SEQUENCE: 84

Thr Leu Xaa Thr Trp Ala Xaa
1               5

<210> SEQ ID NO 85
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (7)..(7)
<223> OTHER INFORMATION: L-Serine-O-phosphate

<400> SEQUENCE: 85

Thr Leu Xaa Thr Trp Ala Xaa
1               5

<210> SEQ ID NO 86
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (7)..(7)
<223> OTHER INFORMATION: L-Serine-O-phosphate

<400> SEQUENCE: 86

Thr Leu Xaa Thr Trp Ala Xaa
1               5

<210> SEQ ID NO 87
<211> LENGTH: 7
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (7)..(7)
<223> OTHER INFORMATION: L-Serine-O-phosphate

<400> SEQUENCE: 87

Thr Leu Xaa Thr Trp Ala Xaa
1               5

<210> SEQ ID NO 88
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-Tryptophan-3-methyl
<220> FEATURE:
<221> NAME/KEY: MISC_FEATURE
<222> LOCATION: (7)..(7)
<223> OTHER INFORMATION: L-Serine-O-phosphate

<400> SEQUENCE: 88

Thr Leu Xaa Thr Xaa Ala Xaa
1               5

<210> SEQ ID NO 89
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: L-Serine-O-phosphate

<400> SEQUENCE: 89

Thr Leu Thr Trp Ala Xaa
1               5

<210> SEQ ID NO 90
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2
```

```
<400> SEQUENCE: 90

Thr Leu Xaa Thr Trp Ala Xaa
1               5

<210> SEQ ID NO 91
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 91

Thr Leu Xaa Thr Trp Ala Xaa
1               5

<210> SEQ ID NO 92
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 92

Thr Leu Xaa Thr Trp Ala Xaa
1               5

<210> SEQ ID NO 93
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
```

```
<221> NAME/KEY: MISC_FEATURE
<222> LOCATION: (7)..(7)
<223> OTHER INFORMATION: C-terminal NH2
<220> FEATURE:
<221> NAME/KEY: MISC_FEATURE
<222> LOCATION: (7)..(7)
<223> OTHER INFORMATION: L-Serine-O-phosphate

<400> SEQUENCE: 93

Thr Leu Xaa Thr Trp Ala Xaa
1               5

<210> SEQ ID NO 94
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (5)..(5)
<223> OTHER INFORMATION: L-Tryptophan-3-methyl
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 94

Thr Leu Xaa Thr Xaa Ala Xaa
1               5

<210> SEQ ID NO 95
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated
<220> FEATURE:
<221> NAME/KEY: MISC_FEATURE
<222> LOCATION: (6)..(6)
<223> OTHER INFORMATION: L-Serine-O-phosphate
<220> FEATURE:
<221> NAME/KEY: MISC_FEATURE
<222> LOCATION: (6)..(6)
<223> OTHER INFORMATION: C-terminal NH2

<400> SEQUENCE: 95

Thr Leu Thr Trp Ala Xaa
1               5

<210> SEQ ID NO 96
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
```

```
<221> NAME/KEY: MISC_FEATURE
<222> LOCATION: (8)..(8)
<223> OTHER INFORMATION: L-Serine-O-phosphate

<400> SEQUENCE: 96

Thr Leu Xaa Ala Trp Ser Ser Xaa
1               5

<210> SEQ ID NO 97
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 97

Thr Leu Xaa Ala Trp Ser Ser Xaa
1               5

<210> SEQ ID NO 98
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate

<400> SEQUENCE: 98

Thr Leu Xaa Ala Trp Ser Ser Xaa
1               5

<210> SEQ ID NO 99
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate

<400> SEQUENCE: 99

Thr Leu Xaa Ala Trp Ser Ser Xaa
1               5

<210> SEQ ID NO 100
<211> LENGTH: 8
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 100

Thr Leu Xaa Ala Trp Ser Ser Xaa
1               5

<210> SEQ ID NO 101
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 101

Thr Leu Xaa Ala Trp Ser Ser Xaa
1               5

<210> SEQ ID NO 102
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine-(CH2CH2cyclohexyl)
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate

<400> SEQUENCE: 102

Thr Leu Xaa Ala Trp Ser Ser Xaa
1               5

<210> SEQ ID NO 103
<211> LENGTH: 8
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate

<400> SEQUENCE: 103

Thr Leu Xaa Ala Trp Ser Ser Xaa
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 104

Thr Leu Xaa Ala Trp Ser Ser Xaa
1               5

<210> SEQ ID NO 105
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 105

Thr Leu Xaa Ala Trp Ser Ser Xaa
1               5
```

```
<210> SEQ ID NO 106
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 106

Thr Leu Xaa Ala Trp Ser Ser Xaa
 1               5

<210> SEQ ID NO 107
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: C-terminal NH2
<220> FEATURE:
<221> NAME/KEY: MISC_FEATURE
<222> LOCATION: (8)..(8)
<223> OTHER INFORMATION: L-Serine-O-phosphate

<400> SEQUENCE: 107

Thr Leu Xaa Ala Trp Ser Ser Xaa
 1               5

<210> SEQ ID NO 108
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 108

Thr Leu Xaa Ser Trp Ser Ser Xaa
 1               5
```

```
<210> SEQ ID NO 109
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 109

Thr Leu Xaa Ser Trp Ser Ser Xaa
1               5

<210> SEQ ID NO 110
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate

<400> SEQUENCE: 110

Thr Leu Xaa Ser Trp Ser Ser Xaa
1               5

<210> SEQ ID NO 111
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate

<400> SEQUENCE: 111

Thr Leu Xaa Ser Trp Ser Ser Xaa
1               5

<210> SEQ ID NO 112
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
```

```
<220> FEATURE:
<221> NAME/KEY: MISC_FEATURE
<222> LOCATION: (8)..(8)
<223> OTHER INFORMATION: L-Serine-O-phosphate

<400> SEQUENCE: 112

Thr Leu Xaa Ser Trp Ser Ser Xaa
1               5

<210> SEQ ID NO 113
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 113

Thr Leu Xaa Ser Trp Ser Ser Xaa
1               5

<210> SEQ ID NO 114
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate

<400> SEQUENCE: 114

Thr Leu Xaa Ser Trp Ser Ser Xaa
1               5

<210> SEQ ID NO 115
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: L-Serine-O-phosphate
```

```
<400> SEQUENCE: 115

Thr Leu Xaa Ser Trp Ser Ser Xaa
1               5

<210> SEQ ID NO 116
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Cysteine-S-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 116

Thr Leu Xaa Ser Trp Ser Ser Xaa
1               5

<210> SEQ ID NO 117
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Asparagine-N-benzyl
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 117

Thr Leu Xaa Ser Trp Ser Ser Xaa
1               5

<210> SEQ ID NO 118
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine(CH2CH2cyclohexyl)
```

```
<220> FEATURE:
<221> NAME/KEY: MISC_FEATURE
<222> LOCATION: (8)..(8)
<223> OTHER INFORMATION: L-Serine-O-phosphate
<220> FEATURE:
<221> NAME/KEY: MISC_FEATURE
<222> LOCATION: (8)..(8)
<223> OTHER INFORMATION: C-terminal NH2

<400> SEQUENCE: 118

Thr Leu Xaa Ser Trp Ser Ser Xaa
1               5

<210> SEQ ID NO 119
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: Homophenylalanine
<220> FEATURE:
<221> NAME/KEY: MISC_FEATURE
<222> LOCATION: (8)..(8)
<223> OTHER INFORMATION: C-terminal NH2
<220> FEATURE:
<221> NAME/KEY: MISC_FEATURE
<222> LOCATION: (8)..(8)
<223> OTHER INFORMATION: L-Serine-O-phosphate

<400> SEQUENCE: 119

Thr Leu Xaa Ser Trp Ser Ser Xaa
1               5

<210> SEQ ID NO 120
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: L-Cysteine-S-benzyl
<220> FEATURE:
<221> NAME/KEY: MISC_FEATURE
<222> LOCATION: (6)..(6)
<223> OTHER INFORMATION: L-Serine-O-phosphate

<400> SEQUENCE: 120

Xaa Thr Trp Ser Ser Xaa
1               5

<210> SEQ ID NO 121
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
```

```
<220> FEATURE:
<221> NAME/KEY: MISC_FEATURE
<222> LOCATION: (1)..(1)
<223> OTHER INFORMATION: L-Asparagine-N-benzyl
<220> FEATURE:
<221> NAME/KEY: MISC_FEATURE
<222> LOCATION: (6)..(6)
<223> OTHER INFORMATION: L-Serine-O-phosphate

<400> SEQUENCE: 121

Xaa Thr Trp Ser Ser Xaa
1               5

<210> SEQ ID NO 122
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: L-Glycine-(CH2CH2cyclohexyl)
<220> FEATURE:
<221> NAME/KEY: MISC_FEATURE
<222> LOCATION: (1)..(1)
<223> OTHER INFORMATION: L-Glycine(CH2CH2cyclohexyl)
<220> FEATURE:
<221> NAME/KEY: MISC_FEATURE
<222> LOCATION: (6)..(6)
<223> OTHER INFORMATION: L-Serine-O-phosphate

<400> SEQUENCE: 122

Xaa Thr Trp Ser Ser Xaa
1               5

<210> SEQ ID NO 123
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: Homophenylalanine
<220> FEATURE:
<221> NAME/KEY: MISC_FEATURE
<222> LOCATION: (6)..(6)
<223> OTHER INFORMATION: L-Serine-O-phosphate

<400> SEQUENCE: 123

Xaa Thr Trp Ser Ser Xaa
1               5

<210> SEQ ID NO 124
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
```

```
<220> FEATURE:
<221> NAME/KEY: MISC_FEATURE
<222> LOCATION: (1)..(1)
<223> OTHER INFORMATION: L-Cysteine-S-benzyl
<220> FEATURE:
<221> NAME/KEY: MISC_FEATURE
<222> LOCATION: (6)..(6)
<223> OTHER INFORMATION: C-terminal NH2
<220> FEATURE:
<221> NAME/KEY: MISC_FEATURE
<222> LOCATION: (6)..(6)
<223> OTHER INFORMATION: L-Serine-O-phosphate

<400> SEQUENCE: 124

Xaa Thr Trp Ser Ser Xaa
1               5

<210> SEQ ID NO 125
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: L-Asparagine-N-benzyl
<220> FEATURE:
<221> NAME/KEY: MISC_FEATURE
<222> LOCATION: (6)..(6)
<223> OTHER INFORMATION: C-terminal NH2
<220> FEATURE:
<221> NAME/KEY: MISC_FEATURE
<222> LOCATION: (6)..(6)
<223> OTHER INFORMATION: L-Serine-O-phosphate

<400> SEQUENCE: 125

Xaa Thr Trp Ser Ser Xaa
1               5

<210> SEQ ID NO 126
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: L-Glycine(CH2CH2cyclohexyl)
<220> FEATURE:
<221> NAME/KEY: MISC_FEATURE
<222> LOCATION: (6)..(6)
<223> OTHER INFORMATION: C-terminal NH2
<220> FEATURE:
<221> NAME/KEY: MISC_FEATURE
<222> LOCATION: (6)..(6)
<223> OTHER INFORMATION: L-Serine-O-phosphate

<400> SEQUENCE: 126

Xaa Thr Trp Ser Ser Xaa
1               5

<210> SEQ ID NO 127
<211> LENGTH: 6
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: Homophenylalanine
<220> FEATURE:
<221> NAME/KEY: MISC_FEATURE
<222> LOCATION: (6)..(6)
<223> OTHER INFORMATION: L-Serine-O-phosphate
<220> FEATURE:
<221> NAME/KEY: MISC_FEATURE
<222> LOCATION: (6)..(6)
<223> OTHER INFORMATION: C-terminal NH2

<400> SEQUENCE: 127

Xaa Thr Trp Ser Ser Xaa
1               5

<210> SEQ ID NO 128
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC
<220> FEATURE:
<221> NAME/KEY: MISC_FEATURE
<222> LOCATION: (1)..(1)
<223> OTHER INFORMATION: L-Cysteine-S-benzyl
<220> FEATURE:
<221> NAME/KEY: MISC_FEATURE
<222> LOCATION: (6)..(6)
<223> OTHER INFORMATION: L-Serine-O-phosphate

<400> SEQUENCE: 128

Xaa Thr Trp Ser Ser Xaa
1               5

<210> SEQ ID NO 129
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC
<220> FEATURE:
<221> NAME/KEY: MISC_FEATURE
<222> LOCATION: (1)..(1)
<223> OTHER INFORMATION: L-Asparagine-N-benzyl
<220> FEATURE:
<221> NAME/KEY: MISC_FEATURE
<222> LOCATION: (6)..(6)
<223> OTHER INFORMATION: L-Serine-O-phosphate

<400> SEQUENCE: 129

Xaa Thr Trp Ser Ser Xaa
1               5

<210> SEQ ID NO 130
<211> LENGTH: 6
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC
<220> FEATURE:
<221> NAME/KEY: MISC_FEATURE
<222> LOCATION: (1)..(1)
<223> OTHER INFORMATION: L-Glycine(CH2CH2cyclohexyl)
<220> FEATURE:
<221> NAME/KEY: MISC_FEATURE
<222> LOCATION: (6)..(6)
<223> OTHER INFORMATION: L-Serine-O-phosphate

<400> SEQUENCE: 130

Xaa Thr Trp Ser Ser Xaa
1               5

<210> SEQ ID NO 131
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC
<220> FEATURE:
<221> NAME/KEY: MISC_FEATURE
<222> LOCATION: (1)..(1)
<223> OTHER INFORMATION: Homophenylalanine
<220> FEATURE:
<221> NAME/KEY: MISC_FEATURE
<222> LOCATION: (6)..(6)
<223> OTHER INFORMATION: L-Serine-O-phosphate

<400> SEQUENCE: 131

Xaa Thr Trp Ser Ser Xaa
1               5

<210> SEQ ID NO 132
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC
<220> FEATURE:
<221> NAME/KEY: MISC_FEATURE
<222> LOCATION: (1)..(1)
<223> OTHER INFORMATION: L-Cysteine-S-benzyl
<220> FEATURE:
<221> NAME/KEY: MISC_FEATURE
<222> LOCATION: (6)..(6)
<223> OTHER INFORMATION: C-terminal NH2
<220> FEATURE:
<221> NAME/KEY: MISC_FEATURE
<222> LOCATION: (6)..(6)
<223> OTHER INFORMATION: L-Serine-O-phosphate

<400> SEQUENCE: 132

Xaa Thr Trp Ser Ser Xaa
1               5

<210> SEQ ID NO 133
<211> LENGTH: 6
```

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC
<220> FEATURE:
<221> NAME/KEY: MISC_FEATURE
<222> LOCATION: (1)..(1)
<223> OTHER INFORMATION: L-Asparagine-N-benzyl
<220> FEATURE:
<221> NAME/KEY: MISC_FEATURE
<222> LOCATION: (6)..(6)
<223> OTHER INFORMATION: C-terminal NH2
<220> FEATURE:
<221> NAME/KEY: MISC_FEATURE
<222> LOCATION: (6)..(6)
<223> OTHER INFORMATION: L-Serine-O-phosphate

<400> SEQUENCE: 133

Xaa Thr Trp Ser Ser Xaa
1               5

<210> SEQ ID NO 134
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC
<220> FEATURE:
<221> NAME/KEY: MISC_FEATURE
<222> LOCATION: (1)..(1)
<223> OTHER INFORMATION: L-Glycine(CH2CH2cyclohexyl)l)
<220> FEATURE:
<221> NAME/KEY: MISC_FEATURE
<222> LOCATION: (6)..(6)
<223> OTHER INFORMATION: C-terminal NH2
<220> FEATURE:
<221> NAME/KEY: MISC_FEATURE
<222> LOCATION: (6)..(6)
<223> OTHER INFORMATION: L-Serine-O-phosphate

<400> SEQUENCE: 134

Xaa Thr Trp Ser Ser Xaa
1               5

<210> SEQ ID NO 135
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC
<220> FEATURE:
<221> NAME/KEY: MISC_FEATURE
<222> LOCATION: (1)..(1)
<223> OTHER INFORMATION: Homophenylalanine
<220> FEATURE:
<221> NAME/KEY: MISC_FEATURE
<222> LOCATION: (6)..(6)
<223> OTHER INFORMATION: L-Serine-O-phosphate
<220> FEATURE:
<221> NAME/KEY: MISC_FEATURE
<222> LOCATION: (6)..(6)
<223> OTHER INFORMATION: C-terminal NH2
```

```
<400> SEQUENCE: 135

Xaa Thr Trp Ser Ser Xaa
1               5

<210> SEQ ID NO 136
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-cysteine-S-methyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 136

Thr Leu Xaa Thr Trp Ser Ser Xaa
1               5

<210> SEQ ID NO 137
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-cysteine-S-2-propyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 137

Thr Leu Xaa Thr Trp Ser Ser Xaa
1               5

<210> SEQ ID NO 138
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-cysteine -S-CH2-3-hydroxyphenyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 138

Thr Leu Xaa Thr Trp Ser Ser Xaa
1               5

<210> SEQ ID NO 139
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-cysteine-S-CH2-3-hydroxyphenyl
```

```
<220> FEATURE:
<221> NAME/KEY: MISC_FEATURE
<222> LOCATION: (8)..(8)
<223> OTHER INFORMATION: L-Serine-O-phosphate

<400> SEQUENCE: 139

Thr Leu Xaa Thr Trp Ser Ser Xaa
1               5

<210> SEQ ID NO 140
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: L-cysteine-S-CH2-3-methyphenyl
<220> FEATURE:
<221> NAME/KEY: MISC_FEATURE
<222> LOCATION: (8)..(8)
<223> OTHER INFORMATION: L-Serine-O-phosphate

<400> SEQUENCE: 140

Thr Leu Xaa Thr Trp Ser Ser Xaa
1               5

<210> SEQ ID NO 141
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (2)..(2)
<223> OTHER INFORMATION: L-cysteine-S-benzyl
<220> FEATURE:
<221> NAME/KEY: MISC_FEATURE
<222> LOCATION: (7)..(7)
<223> OTHER INFORMATION: L-Serine-O-phosphate
<220> FEATURE:
<221> NAME/KEY: MISC_FEATURE
<222> LOCATION: (7)..(7)
<223> OTHER INFORMATION: C-terminal NH2

<400> SEQUENCE: 141

Leu Xaa Thr Trp Ser Ser Xaa
1               5

<210> SEQ ID NO 142
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 4-phenyl-phenylalanine
<220> FEATURE:
<221> NAME/KEY: MISC_FEATURE
<222> LOCATION: (2)..(2)
<223> OTHER INFORMATION: Gly(Et)
<220> FEATURE:
<221> NAME/KEY: MISC_FEATURE
<222> LOCATION: (3)..(3)
<223> OTHER INFORMATION: L-Serine-O-phosphate
```

```
<220> FEATURE:
<221> NAME/KEY: MISC_FEATURE
<222> LOCATION: (3)..(3)
<223> OTHER INFORMATION: C-terminal morpholine

<400> SEQUENCE: 142

Xaa Xaa Xaa
1

<210> SEQ ID NO 143
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (2)..(2)
<223> OTHER INFORMATION: 6-O-Methyl-Tryptophan

<400> SEQUENCE: 143

Tyr Xaa Gly
1

<210> SEQ ID NO 144
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: 3-fluoro-Tyrosine

<400> SEQUENCE: 144

Xaa Trp Gly
1

<210> SEQ ID NO 145
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal pivaloyl

<400> SEQUENCE: 145

Tyr Trp Gly
1

<210> SEQ ID NO 146
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: N-Terminal mesyl

<400> SEQUENCE: 146

Tyr Trp Gly
1

<210> SEQ ID NO 147
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal BOC

<400> SEQUENCE: 147

Tyr Trp Gly
1

<210> SEQ ID NO 148
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: D-tryptophan
<220> FEATURE:
<221> NAME/KEY: MISC_FEATURE
<222> LOCATION: (2)..(2)
<223> OTHER INFORMATION: 3-trifluromethyl-D-phenylalanine
<220> FEATURE:
<221> NAME/KEY: MISC_FEATURE
<222> LOCATION: (3)..(3)
<223> OTHER INFORMATION: D-Arginine
<220> FEATURE:
<221> NAME/KEY: MISC_FEATURE
<222> LOCATION: (3)..(3)
<223> OTHER INFORMATION: C-terminal NH2

<400> SEQUENCE: 148

Xaa Xaa Xaa
1

<210> SEQ ID NO 149
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: D-tryptophan
<220> FEATURE:
<221> NAME/KEY: MISC_FEATURE
<222> LOCATION: (2)..(2)
<223> OTHER INFORMATION: 3-chloro-D-phenylalanine
<220> FEATURE:
<221> NAME/KEY: MISC_FEATURE
<222> LOCATION: (3)..(3)
```

```
<223> OTHER INFORMATION: D-Arginine
<220> FEATURE:
<221> NAME/KEY: MISC_FEATURE
<222> LOCATION: (3)..(3)
<223> OTHER INFORMATION: C-terminal NH2

<400> SEQUENCE: 149

Xaa Xaa Xaa
1

<210> SEQ ID NO 150
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: D-tryptophan
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-Arginine
<220> FEATURE:
<221> NAME/KEY: MISC_FEATURE
<222> LOCATION: (3)..(3)
<223> OTHER INFORMATION: C-terminal NH2

<400> SEQUENCE: 150

Xaa Xaa Xaa
1

<210> SEQ ID NO 151
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: D-tryptophan
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-Arginine

<400> SEQUENCE: 151

Xaa Xaa Xaa
1

<210> SEQ ID NO 152
<211> LENGTH: 3
<212> TYPE: PRT
<213> ORGANISM: Artificial sequence
<220> FEATURE:
```

<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: N-Methyl-D-arginine
<220> FEATURE:
<221> NAME/KEY: MISC_FEATURE
<222> LOCATION: (2)..(2)
<223> OTHER INFORMATION: 3-hydroxy-D-phenylalanine
<220> FEATURE:
<221> NAME/KEY: MISC_FEATURE
<222> LOCATION: (3)..(3)
<223> OTHER INFORMATION: D-tryptophan
<220> FEATURE:
<221> NAME/KEY: MISC_FEATURE
<222> LOCATION: (3)..(3)
<223> OTHER INFORMATION: C-terminal NH2

<400> SEQUENCE: 152

Xaa Xaa Xaa
1

<210> SEQ ID NO 153
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (2)..(2)
<223> OTHER INFORMATION: 3-Trifluoromethyl-L-phenylalanine

<400> SEQUENCE: 153

Arg Xaa Gly
1

<210> SEQ ID NO 154
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: C-Terminal N-methyl-3-trifluoromethylaniline

<400> SEQUENCE: 154

Ala Val Arg
1

<210> SEQ ID NO 155
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)

```
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: D-arginine
<220> FEATURE:
<221> NAME/KEY: MISC_FEATURE
<222> LOCATION: (2)..(2)
<223> OTHER INFORMATION: 3-hydroxy-D-phenylalanine
<220> FEATURE:
<221> NAME/KEY: MISC_FEATURE
<222> LOCATION: (3)..(3)
<223> OTHER INFORMATION: D-tryptophan

<400> SEQUENCE: 155

Xaa Xaa Xaa
1

<210> SEQ ID NO 156
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (1)..(1)
<223> OTHER INFORMATION: D-arginine
<220> FEATURE:
<221> NAME/KEY: MISC_FEATURE
<222> LOCATION: (2)..(2)
<223> OTHER INFORMATION: 3-hydroxy-D-phenylalanine
<220> FEATURE:
<221> NAME/KEY: MISC_FEATURE
<222> LOCATION: (3)..(3)
<223> OTHER INFORMATION: D-tryptophan
<220> FEATURE:
<221> NAME/KEY: MISC_FEATURE
<222> LOCATION: (3)..(3)
<223> OTHER INFORMATION: C-terminal NH2

<400> SEQUENCE: 156

Xaa Xaa Xaa
1

<210> SEQ ID NO 157
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal Propionyl
<220> FEATURE:
<221> NAME/KEY: MISC_FEATURE
<222> LOCATION: (1)..(1)
<223> OTHER INFORMATION: D-arginine
<220> FEATURE:
<221> NAME/KEY: MISC_FEATURE
<222> LOCATION: (2)..(2)
<223> OTHER INFORMATION: 3-hydroxy-D-phenylalanine
<220> FEATURE:
<221> NAME/KEY: MISC_FEATURE
<222> LOCATION: (3)..(3)
<223> OTHER INFORMATION: D-tryptophan

<400> SEQUENCE: 157

Xaa Xaa Xaa
```

```
<210> SEQ ID NO 158
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue

<400> SEQUENCE: 158

Val Arg Phe Trp
1

<210> SEQ ID NO 159
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue

<400> SEQUENCE: 159

Tyr Val Arg Phe Trp
1               5

<210> SEQ ID NO 160
<211> LENGTH: 6
<212> TYPE: PRT
<213> ORGANISM: Artificial sequence
<220> FEATURE:
<223> OTHER INFORMATION: Synthetic

<400> SEQUENCE: 160

Val Tyr Asp Arg Phe Trp
1               5

<210> SEQ ID NO 161
<211> LENGTH: 6
<212> TYPE: PRT
<213> ORGANISM: Artificial sequence
<220> FEATURE:
<223> OTHER INFORMATION: Synthetic

<400> SEQUENCE: 161

Val Tyr Glu Arg Phe Trp
1               5

<210> SEQ ID NO 162
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Citrulline

<400> SEQUENCE: 162

Val Tyr Val Xaa Phe Trp
1               5
```

```
<210> SEQ ID NO 163
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-valine
<220> FEATURE:
<221> NAME/KEY: MISC_FEATURE
<222> LOCATION: (2)..(2)
<223> OTHER INFORMATION: D-tyrosine
<220> FEATURE:
<221> NAME/KEY: MISC_FEATURE
<222> LOCATION: (3)..(3)
<223> OTHER INFORMATION: D-valine
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (5)..(5)
<223> OTHER INFORMATION: D-phenylalanine
<220> FEATURE:
<221> NAME/KEY: MISC_FEATURE
<222> LOCATION: (6)..(6)
<223> OTHER INFORMATION: D-tryptophan

<400> SEQUENCE: 163

Xaa Xaa Xaa Xaa Xaa Xaa
1               5

<210> SEQ ID NO 164
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-tryptophan
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-arginine
<220> FEATURE:
<221> NAME/KEY: MISC_FEATURE
<222> LOCATION: (4)..(4)
<223> OTHER INFORMATION: D-valine
<220> FEATURE:
<221> NAME/KEY: MISC_FEATURE
<222> LOCATION: (5)..(5)
<223> OTHER INFORMATION: D-tyrosine
<220> FEATURE:
<221> NAME/KEY: MISC_FEATURE
<222> LOCATION: (6)..(6)
<223> OTHER INFORMATION: D-valine

<400> SEQUENCE: 164

Xaa Xaa Xaa Xaa Xaa Xaa
1               5

<210> SEQ ID NO 165
<211> LENGTH: 3
<212> TYPE: PRT
<213> ORGANISM: Artificial sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-arginine
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-tryptophan

<400> SEQUENCE: 165

Xaa Xaa Xaa
1

<210> SEQ ID NO 166
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-acetyl-D-arginine
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-tryptophan

<400> SEQUENCE: 166

Xaa Xaa Xaa
1

<210> SEQ ID NO 167
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-acetyl-D-arginine
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-Tryptophan-NH2

<400> SEQUENCE: 167

Xaa Xaa Xaa
1

<210> SEQ ID NO 168
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: D-tryptophan
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-arginine

<400> SEQUENCE: 168

Xaa Xaa Xaa
1

<210> SEQ ID NO 169
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NH2

<400> SEQUENCE: 169

Val Tyr Val Xaa Phe Xaa
1               5

<210> SEQ ID NO 170
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: L-citrulline

<400> SEQUENCE: 170

Val Tyr Val Xaa Phe His
1               5

<210> SEQ ID NO 171
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: 2-methyl-L-histidine

<400> SEQUENCE: 171

Val Tyr Val Xaa Phe Xaa
1               5

<210> SEQ ID NO 172
<211> LENGTH: 5
<212> TYPE: PRT
```

```
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (5)..(5)
<223> OTHER INFORMATION: L-phenylalanine-NH(cyclopentyl)

<400> SEQUENCE: 172

Val Tyr Val Xaa Xaa
1               5

<210> SEQ ID NO 173
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NHMe

<400> SEQUENCE: 173

Val Tyr Val Xaa Phe Xaa
1               5

<210> SEQ ID NO 174
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NHMe

<400> SEQUENCE: 174

Val Tyr Val Xaa Phe Xaa
1               5

<210> SEQ ID NO 175
<211> LENGTH: 6
<212> TYPE: PRT
<213> ORGANISM: Artificial sequence
<220> FEATURE:
<223> OTHER INFORMATION: synthetic

<400> SEQUENCE: 175

Val Tyr His Arg Phe Trp
1               5

<210> SEQ ID NO 176
<211> LENGTH: 6
<212> TYPE: PRT
<213> ORGANISM: Artificial sequence
<220> FEATURE:
<223> OTHER INFORMATION: synthetic
```

```
<400> SEQUENCE: 176

Val Tyr Ala Arg Phe Trp
1               5

<210> SEQ ID NO 177
<211> LENGTH: 6
<212> TYPE: PRT
<213> ORGANISM: Artificial sequence
<220> FEATURE:
<223> OTHER INFORMATION: synthetic

<400> SEQUENCE: 177

Val Tyr Ser Arg Phe Trp
1               5

<210> SEQ ID NO 178
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: L-homoserine

<400> SEQUENCE: 178

Val Tyr Xaa Arg Phe Trp
1               5

<210> SEQ ID NO 179
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Gly(Et)

<400> SEQUENCE: 179

Val Tyr Xaa Arg Phe Trp
1               5

<210> SEQ ID NO 180
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-ornithine

<400> SEQUENCE: 180

Val Tyr Val Xaa Phe Trp
1               5

<210> SEQ ID NO 181
<211> LENGTH: 6
<212> TYPE: PRT
<213> ORGANISM: Artificial sequence
<220> FEATURE:
<223> OTHER INFORMATION: synthetic

<400> SEQUENCE: 181
```

```
Val Tyr Val Gln Phe Trp
1               5

<210> SEQ ID NO 182
<211> LENGTH: 6
<212> TYPE: PRT
<213> ORGANISM: Artificial sequence
<220> FEATURE:
<223> OTHER INFORMATION: synthetic

<400> SEQUENCE: 182

Val Tyr Val Glu Phe Trp
1               5

<210> SEQ ID NO 183
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: N-propyl-L-glutamine

<400> SEQUENCE: 183

Val Tyr Val Xaa Phe Trp
1               5

<210> SEQ ID NO 184
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: N-2-hydroxylpropyl-L-glutamine

<400> SEQUENCE: 184

Val Tyr Val Xaa Phe Trp
1               5

<210> SEQ ID NO 185
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-Norarginine

<400> SEQUENCE: 185

Val Tyr Val Xaa Phe Trp
1               5

<210> SEQ ID NO 186
<211> LENGTH: 6
<212> TYPE: PRT
<213> ORGANISM: Artificial sequence
<220> FEATURE:
<223> OTHER INFORMATION: synthetic

<400> SEQUENCE: 186

Val Tyr Val Lys Phe Trp
```

```
1               5

<210> SEQ ID NO 187
<211> LENGTH: 6
<212> TYPE: PRT
<213> ORGANISM: Artificial sequence
<220> FEATURE:
<223> OTHER INFORMATION: synthetic

<400> SEQUENCE: 187

Val Tyr Val Arg Phe Val
1               5

<210> SEQ ID NO 188
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-alanine

<400> SEQUENCE: 188

Xaa Tyr Val Arg Phe Trp
1               5

<210> SEQ ID NO 189
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: (CH3)2CHCO-L-tyrosine

<400> SEQUENCE: 189

Xaa Val Glu Phe Trp
1               5

<210> SEQ ID NO 190
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: (CH3)3CCO-L-tyrosine

<400> SEQUENCE: 190

Xaa Val Glu Phe Trp
1               5

<210> SEQ ID NO 191
<211> LENGTH: 4
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: (CH3)3CCO-L-tyrosine
<220> FEATURE:
<221> NAME/KEY: MISC_FEATURE
```

```
<222> LOCATION: (4)..(4)
<223> OTHER INFORMATION: L-phenylalanine-NH(cyclopentyl)

<400> SEQUENCE: 191

Xaa Val Glu Xaa
1

<210> SEQ ID NO 192
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: 4-OMe-L-phenylalanine
<220> FEATURE:
<221> NAME/KEY: MISC_FEATURE
<222> LOCATION: (5)..(5)
<223> OTHER INFORMATION: 4-fluoro-L-phenylalanine
<220> FEATURE:
<221> NAME/KEY: MISC_FEATURE
<222> LOCATION: (6)..(6)
<223> OTHER INFORMATION: L-tryptophan-NH2

<400> SEQUENCE: 192

Val Xaa Val Arg Xaa Xaa
1               5

<210> SEQ ID NO 193
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: 4-phenyl-L-phenylalanine
<220> FEATURE:
<221> NAME/KEY: MISC_FEATURE
<222> LOCATION: (2)..(2)
<223> OTHER INFORMATION: Gly(Et)
<220> FEATURE:
<221> NAME/KEY: MISC_FEATURE
<222> LOCATION: (3)..(3)
<223> OTHER INFORMATION: L-Serine-O-phosphate
<220> FEATURE:
<221> NAME/KEY: MISC_FEATURE
<222> LOCATION: (3)..(3)
<223> OTHER INFORMATION: C-terminal morpholine

<400> SEQUENCE: 193

Xaa Xaa Xaa
1

<210> SEQ ID NO 194
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: 4-phenyl-L-phenylalanine
<220> FEATURE:
<221> NAME/KEY: MISC_FEATURE
<222> LOCATION: (3)..(3)
<223> OTHER INFORMATION: L-serine( p)-morpholine

<400> SEQUENCE: 194
```

Xaa Leu Xaa
1

<210> SEQ ID NO 195
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: 4-phenyl-L-phenylalanine
<220> FEATURE:
<221> NAME/KEY: MISC_FEATURE
<222> LOCATION: (3)..(3)
<223> OTHER INFORMATION: L-serine( p)-(4-Me-piperazine)

<400> SEQUENCE: 195

Xaa Ala Xaa
1

<210> SEQ ID NO 196
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: 4-(3-OH)-phenyl-L-phenylalanine
<220> FEATURE:
<221> NAME/KEY: MISC_FEATURE
<222> LOCATION: (3)..(3)
<223> OTHER INFORMATION: L-serine( p)-morpholine

<400> SEQUENCE: 196

Xaa Ala Xaa
1

<210> SEQ ID NO 197
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Ibutyryl-L-tyrosine

<400> SEQUENCE: 197

Xaa Val Arg Phe Trp
1               5

<210> SEQ ID NO 198
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Pivaloyl-L-tyrosine

<400> SEQUENCE: 198

Xaa Val Arg Phe Trp
1               5

```
<210> SEQ ID NO 199
<211> LENGTH: 7
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: L-citrulline

<400> SEQUENCE: 199

Gly Val Tyr Val Xaa Phe Trp
1               5

<210> SEQ ID NO 200
<211> LENGTH: 7
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline

<400> SEQUENCE: 200

Val Tyr Val Xaa Phe Trp Gly
1               5

<210> SEQ ID NO 201
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NHMe

<400> SEQUENCE: 201

Val Tyr Val Xaa Phe Xaa
1               5

<210> SEQ ID NO 202
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: D-phenylalanine

<400> SEQUENCE: 202

Val Tyr Val Arg Xaa Trp
1               5

<210> SEQ ID NO 203
<211> LENGTH: 3
<212> TYPE: PRT
<213> ORGANISM: Artificial sequence
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: N-acetyl-D-tryptophan
<220> FEATURE:
<221> NAME/KEY: MISC_FEATURE
<222> LOCATION: (2)..(2)
<223> OTHER INFORMATION: D-alanine
<220> FEATURE:
<221> NAME/KEY: MISC_FEATURE
<222> LOCATION: (3)..(3)
<223> OTHER INFORMATION: D-arginine-NH2

<400> SEQUENCE: 203

Xaa Xaa Xaa
1

<210> SEQ ID NO 204
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-Boc-D-tryptophan
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-arginine-NH2

<400> SEQUENCE: 204

Xaa Xaa Xaa
1

<210> SEQ ID NO 205
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-MeOCO-D-tryptophan
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: D-arginine-NH2

<400> SEQUENCE: 205

Xaa Xaa Xaa
1

<210> SEQ ID NO 206
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
```

```
<223> OTHER INFORMATION: N-Succinyl-L-tyrosine
<220> FEATURE:
<221> NAME/KEY: MISC_FEATURE
<222> LOCATION: (3)..(3)
<223> OTHER INFORMATION: L-citrulline

<400> SEQUENCE: 206

Xaa Val Xaa Phe Trp
1               5

<210> SEQ ID NO 207
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-ornithine
<220> FEATURE:
<221> NAME/KEY: MISC_FEATURE
<222> LOCATION: (6)..(6)
<223> OTHER INFORMATION: L-tryptophan-NH2

<400> SEQUENCE: 207

Val Tyr Val Xaa Phe Xaa
1               5

<210> SEQ ID NO 208
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-acetyl-L-arginine

<400> SEQUENCE: 208

Xaa Phe Trp
1

<210> SEQ ID NO 209
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NHEt

<400> SEQUENCE: 209

Val Tyr Val Xaa Phe Xaa
1               5

<210> SEQ ID NO 210
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
```

```
<222> LOCATION: (6)..(6)
<223> OTHER INFORMATION: D-tryptophan

<400> SEQUENCE: 210

Val Tyr Val Arg Phe Xaa
1               5

<210> SEQ ID NO 211
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: D-tryptophan-NH2

<400> SEQUENCE: 211

Val Tyr Val Xaa Phe Xaa
1               5

<210> SEQ ID NO 212
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NH2

<400> SEQUENCE: 212

Val Tyr Val Xaa Phe Xaa
1               5

<210> SEQ ID NO 213
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (5)..(5)
<223> OTHER INFORMATION: L-phenylalanine-NH2

<400> SEQUENCE: 213

Val Tyr Val Xaa Xaa
1               5

<210> SEQ ID NO 214
<211> LENGTH: 4
<212> TYPE: PRT
<213> ORGANISM: Artificial sequence
<220> FEATURE:
<223> OTHER INFORMATION: synthetic
<220> FEATURE:
```

```
<221> NAME/KEY: MISC_FEATURE
<222> LOCATION: (4)..(4)
<223> OTHER INFORMATION: L-citrulline-NH2

<400> SEQUENCE: 214

Val Tyr Val Xaa
1

<210> SEQ ID NO 215
<211> LENGTH: 4
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline-NH(isopropyl)

<400> SEQUENCE: 215

Val Tyr Val Xaa
1

<210> SEQ ID NO 216
<211> LENGTH: 4
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: D-tyrosine
<220> FEATURE:
<221> NAME/KEY: MISC_FEATURE
<222> LOCATION: (4)..(4)
<223> OTHER INFORMATION: L-citrulline-NHEt

<400> SEQUENCE: 216

Val Xaa Val Xaa
1

<210> SEQ ID NO 217
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: L-tryptophan-NHMe

<400> SEQUENCE: 217

Val Tyr Val Arg Phe Xaa
1               5

<210> SEQ ID NO 218
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: L-tryptophan-NHEt

<400> SEQUENCE: 218

Val Tyr Val Arg Phe Xaa
```

```
1               5

<210> SEQ ID NO 219
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: D-tryptophan-NH2

<400> SEQUENCE: 219

Val Tyr Val Arg Phe Xaa
1               5

<210> SEQ ID NO 220
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: D-tyrosine
<220> FEATURE:
<221> NAME/KEY: MISC_FEATURE
<222> LOCATION: (6)..(6)
<223> OTHER INFORMATION: L-tryptophan-NH2

<400> SEQUENCE: 220

Val Xaa Val Arg Phe Xaa
1               5

<210> SEQ ID NO 221
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: L-phenylalanine-NH2

<400> SEQUENCE: 221

Val Tyr Val Arg Xaa
1               5

<210> SEQ ID NO 222
<211> LENGTH: 4
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-arginine-NH2

<400> SEQUENCE: 222

Val Tyr Val Xaa
1

<210> SEQ ID NO 223
<211> LENGTH: 4
<212> TYPE: PRT
<213> ORGANISM: Artificial sequence
```

```
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-arginine-NH(isopropyl)

<400> SEQUENCE: 223

Val Tyr Val Xaa
1

<210> SEQ ID NO 224
<211> LENGTH: 4
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: D-tyrosine
<220> FEATURE:
<221> NAME/KEY: MISC_FEATURE
<222> LOCATION: (4)..(4)
<223> OTHER INFORMATION: L-arginine-NHEt

<400> SEQUENCE: 224

Val Xaa Val Xaa
1

<210> SEQ ID NO 225
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: L-tryptophan-NH2

<400> SEQUENCE: 225

Val Phe Val Arg Phe Xaa
1               5

<210> SEQ ID NO 226
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NH2

<400> SEQUENCE: 226

Val Phe Val Xaa Phe Xaa
1               5

<210> SEQ ID NO 227
<211> LENGTH: 6
<212> TYPE: PRT
<213> ORGANISM: Artificial sequence
<220> FEATURE:
<223> OTHER INFORMATION: synthetic
<220> FEATURE:
```

```
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NHMe

<400> SEQUENCE: 227

Val Phe Val Xaa Phe Xaa
1               5

<210> SEQ ID NO 228
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NHEt

<400> SEQUENCE: 228

Val Phe Val Xaa Phe Xaa
1               5

<210> SEQ ID NO 229
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: L-phenylalanine-NH(cyclopentyl)

<400> SEQUENCE: 229

Val Phe Val Arg Xaa
1               5

<210> SEQ ID NO 230
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (5)..(5)
<223> OTHER INFORMATION: L-phenylalanine-NH(cyclopentyl)

<400> SEQUENCE: 230

Val Phe Val Xaa Xaa
1               5

<210> SEQ ID NO 231
<211> LENGTH: 6
<212> TYPE: PRT
<213> ORGANISM: Artificial sequence
<220> FEATURE:
<223> OTHER INFORMATION: synthetic
```

```
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NH(propyl)

<400> SEQUENCE: 231

Val Tyr Val Xaa Phe Xaa
1               5

<210> SEQ ID NO 232
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: L-citrulline
<220> FEATURE:
<221> NAME/KEY: MISC_FEATURE
<222> LOCATION: (6)..(6)
<223> OTHER INFORMATION: L-tryptophan-NH(isopropyl)

<400> SEQUENCE: 232

Val Tyr Val Xaa Phe Xaa
1               5

<210> SEQ ID NO 233
<211> LENGTH: 6
<212> TYPE: PRT
<213> ORGANISM: Artificial sequence
<220> FEATURE:
<223> OTHER INFORMATION: synthetic

<400> SEQUENCE: 233

Val Phe Val Arg Phe Trp
1               5

<210> SEQ ID NO 234
<211> LENGTH: 6
<212> TYPE: PRT
<213> ORGANISM: Artificial sequence
<220> FEATURE:
<223> OTHER INFORMATION: synthetic

<400> SEQUENCE: 234

Ala Phe Val Ser Phe Trp
1               5

<210> SEQ ID NO 235
<211> LENGTH: 8
<212> TYPE: PRT
<213> ORGANISM: Artificial sequence
<220> FEATURE:
<223> OTHER INFORMATION: synthetic

<400> SEQUENCE: 235

Thr Leu Cys Thr Trp Ser Ser Ser
1               5

<210> SEQ ID NO 236
<211> LENGTH: 8
<212> TYPE: PRT
<213> ORGANISM: Artificial sequence
```

```
<220> FEATURE:
<223> OTHER INFORMATION: synthetic

<400> SEQUENCE: 236

Thr Leu Asp Thr Trp Ser Ser Ser
1               5

<210> SEQ ID NO 237
<211> LENGTH: 8
<212> TYPE: PRT
<213> ORGANISM: Artificial sequence
<220> FEATURE:
<223> OTHER INFORMATION: synthetic

<400> SEQUENCE: 237

Thr Leu Gly Thr Trp Ser Ser Ser
1               5

<210> SEQ ID NO 238
<211> LENGTH: 8
<212> TYPE: PRT
<213> ORGANISM: Artificial sequence
<220> FEATURE:
<223> OTHER INFORMATION: synthetic

<400> SEQUENCE: 238

Thr Leu Phe Thr Trp Ser Ser Ser
1               5

<210> SEQ ID NO 239
<211> LENGTH: 7
<212> TYPE: PRT
<213> ORGANISM: Artificial sequence
<220> FEATURE:
<223> OTHER INFORMATION: synthetic

<400> SEQUENCE: 239

Thr Leu Thr Trp Ser Ser Ser
1               5

<210> SEQ ID NO 240
<211> LENGTH: 6
<212> TYPE: PRT
<213> ORGANISM: Artificial sequence
<220> FEATURE:
<223> OTHER INFORMATION: synthetic

<400> SEQUENCE: 240

Thr Phe Arg Val Tyr Val
1               5

<210> SEQ ID NO 241
<211> LENGTH: 6
<212> TYPE: PRT
<213> ORGANISM: Artificial sequence
<220> FEATURE:
<223> OTHER INFORMATION: synthetic

<400> SEQUENCE: 241

Ala Tyr Val Arg Phe Trp
1               5

<210> SEQ ID NO 242
<211> LENGTH: 5
<212> TYPE: PRT
<213> ORGANISM: Artificial sequence
<220> FEATURE:
```

```
<223> OTHER INFORMATION: synthetic

<400> SEQUENCE: 242

Tyr Val Glu Phe Trp
1               5

<210> SEQ ID NO 243
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: 4-Phenyl-L-phenylalanine
<220> FEATURE:
<221> NAME/KEY: MISC_FEATURE
<222> LOCATION: (2)..(2)
<223> OTHER INFORMATION: Gly(Et)
<220> FEATURE:
<221> NAME/KEY: MISC_FEATURE
<222> LOCATION: (3)..(3)
<223> OTHER INFORMATION: L-serine-(p)-morpholine

<400> SEQUENCE: 243

Xaa Xaa Xaa
1

<210> SEQ ID NO 244
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: L-phenylalanine-4-phenyl
<220> FEATURE:
<221> NAME/KEY: MISC_FEATURE
<222> LOCATION: (3)..(3)
<223> OTHER INFORMATION: L-serine-(p)-(4-Me-piperazine)

<400> SEQUENCE: 244

Xaa Ala Xaa
1

<210> SEQ ID NO 245
<211> LENGTH: 3
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: [4-(3-OH)-Phenyl]-L-phenylalanine
<220> FEATURE:
<221> NAME/KEY: MISC_FEATURE
<222> LOCATION: (3)..(3)
<223> OTHER INFORMATION: L-serine-(p)-morpholine

<400> SEQUENCE: 245

Xaa Ala Xaa
1

<210> SEQ ID NO 246
<211> LENGTH: 6
<212> TYPE: PRT
<213> ORGANISM: Artificial sequence
```

```
<220> FEATURE:
<223> OTHER INFORMATION: synthetic

<400> SEQUENCE: 246

Val Tyr Gly Arg Phe Trp
1               5

<210> SEQ ID NO 247
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: L-phenylalanine-NH(cyclopentyl)

<400> SEQUENCE: 247

Val Tyr Val Arg Xaa
1               5

<210> SEQ ID NO 248
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal aceylated residue
<220> FEATURE:
<221> NAME/KEY: MISC_FEATURE
<222> LOCATION: (3)..(3)
<223> OTHER INFORMATION: L-Glycine-(CH2CH2cyclohexyl)
<220> FEATURE:
<221> NAME/KEY: MISC_FEATURE
<222> LOCATION: (8)..(8)
<223> OTHER INFORMATION: L-Serine-O-phosphate

<400> SEQUENCE: 248

Thr Leu Xaa Thr Trp Ser Ser Xaa
1               5
```